(12) United States Patent
Pantaleo et al.

(10) Patent No.: US 10,730,933 B2
(45) Date of Patent: Aug. 4, 2020

(54) HIV BINDING AGENTS

(71) Applicants: Centre Hospitalier Universitaire Vaudois, Lausanne (CH); Institute for Research in Biomedicine, Bellinzona (CH)

(72) Inventors: Giuseppe Pantaleo, Lausanne (CH); Antonio Lanzavecchia, Bellinzona (CH)

(73) Assignees: Centre Hospitalier Universitaire Vaudois, Lausanne (CH); Institute For Research In Biomedicine, Bellinoza (CH)

( * ) Notice: Subject to any disclaimer, the term of this patent is extended or adjusted under 35 U.S.C. 154(b) by 91 days.

(21) Appl. No.: 15/780,821

(22) PCT Filed: Dec. 5, 2016

(86) PCT No.: PCT/IB2016/057367
§ 371 (c)(1),
(2) Date: Jun. 1, 2018

(87) PCT Pub. No.: WO2017/093985
PCT Pub. Date: Jun. 8, 2017

(65) Prior Publication Data
US 2019/0345234 A1 Nov. 14, 2019

Related U.S. Application Data

(60) Provisional application No. 62/263,618, filed on Dec. 5, 2015.

(51) Int. Cl.
*C07K 16/10* (2006.01)
*C07K 16/12* (2006.01)

(52) U.S. Cl.
CPC ...... *C07K 16/1063* (2013.01); *C07K 2317/21* (2013.01); *C07K 2317/52* (2013.01); *C07K 2317/565* (2013.01); *C07K 2317/76* (2013.01); *C07K 2317/92* (2013.01)

(58) Field of Classification Search
CPC ............ C07K 16/1063; C07K 2317/21; C07K 2317/565; C07K 2317/54; C07K 2317/55; C07K 2317/32; A61K 2039/505; A61K 38/00
See application file for complete search history.

(56) References Cited

U.S. PATENT DOCUMENTS

| | | | |
|---|---|---|---|
| 4,816,567 A | 3/1989 | Cabilly et al. | |
| 5,087,557 A | 2/1992 | McClure | |
| 5,298,419 A | 3/1994 | Masuho et al. | |
| 5,459,060 A | 10/1995 | Cotropia | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,693,752 A | 12/1997 | Katinger et al. | |
| 5,731,189 A | 3/1998 | Zolla-Pazner et al. | |
| 5,753,503 A | 5/1998 | Katinger et al. | |
| 5,804,440 A | 9/1998 | Burton et al. | |
| 5,911,989 A | 6/1999 | Katinger et al. | |
| 6,057,421 A | 5/2000 | Muller et al. | |
| 7,744,887 B2 | 6/2010 | Shiver et al. | |
| 2003/0118985 A1 | 6/2003 | Hunt et al. | |
| 2007/0292390 A1 | 12/2007 | Dimitrov et al. | |
| 2012/0269821 A1 | 10/2012 | Haynes et al. | |
| 2014/0205612 A1 | 7/2014 | Chan-Hui et al. | |
| 2014/0342407 A1 | 11/2014 | Connors et al. | |

FOREIGN PATENT DOCUMENTS

| | | |
|---|---|---|
| AU | 680836 B2 | 8/1997 |
| DE | 3932461 A1 | 4/1990 |
| EP | 0251612 B1 | 3/1994 |
| EP | 0335134 B1 | 3/1995 |
| WO | 9009805 A1 | 9/1990 |
| WO | 9110742 A1 | 7/1991 |
| WO | 0124810 A1 | 4/2001 |
| WO | 2002032452 A1 | 4/2002 |
| WO | 2015103549 A1 | 7/2015 |
| WO | 2017093985 A1 | 6/2017 |

OTHER PUBLICATIONS

Pascallis et al. J Immunol Sep. 15, 2002, 169 (6) 3076-3084.*
MacCallum et al. J Mol Biol. Oct. 11, 1996;262(5):732-45.*
Casset et al. vol. 307, Issue 1, Jul. 18, 2003, pp. 198-205.*
M Brown et al. J Immunol May 1, 1996, 156 (9) 3285-3291.*
J Mol Biol. Jul. 5, 2002;320(2):415-28.*
EP Application No. 2016057367, dated Mar. 28, 2017, International Search Report.
EP Application No. 2016057367, Written Opinion.
EP Application No. 2016057367, dated Jun. 5, 2018, Int. Pr. Exam. Report.
Boerner, et al. Production of Antigen-Specific Human Monoclonal Antibodies from In Vitro-Primed Human Splenocytes. J. Immunol., 147(1):86-95 (1991).
Bryson, et al. Crystallographic definition of the epitope promiscuity of the broadly neutralizing anti-human immunodeficiency virus type 1 antibody 2F5: vaccine design implications. J. Virol. 83(22): 11862-11875 (2009).
Cohen, et al. Atypical HIV serological profile of novel HIV-1 variant distinct from subtype O. Lancet, 345(8953): 856 (1995).
Cohen, et al. GP41, partial [Human immunodeficiency virus 1], GenBank Accession No. CAA58216.1 (1994).
Cole, et al. Monoclonal Antibodies and Cancer Therapy, Alan R. Liss, p. 77 (1985).
Cole, et al. Monoclonal Antibodies. Can. Fam. Phys. 33: 369-372 (1987).

(Continued)

*Primary Examiner* — Bao Q Li
(74) *Attorney, Agent, or Firm* — Patrick j. Halloran

(57) ABSTRACT

This disclosure relates to binding agents with specificity for HIV and to methods for using the same to treat, prevent and/or ameliorate HIV infection and/or AIDS.

20 Claims, 24 Drawing Sheets
Specification includes a Sequence Listing.

(56) References Cited

OTHER PUBLICATIONS

Decamp, A., et al., Global Panel of HIV-1 Env Reference Strains for Standardized Assessments of Vaccine-Elicited Neutralizing Antibodies, J Virol., 2014; 88(5): 2489-2507.
Earl, et al. Epitope map of human immunodeficiency virus type 1 gp41 derived from 47 monoclonal antibodies produced by immunization with oligomeric envelope protein. J. Virol. 71(4): 2674-84 (1997).
Ebersbach, et al. Affilin-novel binding molecules based on human gamma-B-crystallin, an all beta-sheet protein. J. Mol. Biol. 372 (1): 172-85 (2007).
Eckert, et al. Design of potent inhibitors of HIV-1 entry from the gp41 N-peptide region. PNAS USA, 98(2): 11187-92 (2001) (WO 2005/118887A2).
Edmonds, et al. Replication competent molecular clones of HIV-1 expressing Renilla luciferase facilitate the analysis of antibody inhibition in PBMC. Virol. 408(1): 1-13 (2010).
Evans et al. Human monoclonal antibody directed against gag gene products of the human immunodeficiency virus. J. Immunol. 140(3): 941-3 (1988) (Abstract).
Falkowska, E., et al., Broadly Neutralizing HIV Antibodies Define a Glycan-Dependent Epitope on the Prefusion Conformation of gp41 on Cleaved Envelope Trimers, Immunity, 2014; 40: 657-668.
Fishwild et al. High-avidity human IgGK monoclonal antibodies from a novel strain of minlocus transgenic mice. Nature Biotechnology 14, 845-51 (1996).
GenBank Accession No. 1103299B (Meusing, et al. Nature 313 (6002), 450-458 (1985).
GenBank Accession No. K03455 (NCBI GenPept Accession No. AAB50262).
Gorney, et al. Generation of human monoclonal antibodies to human immunodeficiency virus. PNAS USA 86: 1624-1628 (1989).
Grabulovski, et al. A Novel, Non-immunogenic Fyn SH3-derived Binding Protein with Tumor Vasculature Targeting Properties. J. Biol. Chem. 282 (5): 3196-3204 (2007).
Hoogenboom, et al. By-passing Immunisation. Human Antibodies from Synthetic Repertoires of Germline VH Gene Segments Rearranged in Vitro. J. Mol. Biol., 227:381 (1991).
Huang, et al. Broad and potent neutralization of HIV-1 by a gp41-specific human antibody. Nature 491, 406-412 (2012).
Huang, J., et al., Broad and potent HIV-1 neutralization by a human antibody that binds the gp41-gp120 interface, Nature, 2014; 515:138-142.
Jiang, et al. A Conformation-Specific Monoclonal Antibody Reacting with Fusion-Active gp41 from the Human Immunodeficiency Virus Type 1 Envelope Glycoprotein. J. Virol. 72(12): 10213-17 (1998).
Jones, et al. Replacing the complementarity-determining regions in a human antibody with those from a mouse. Nature, 321:522-525 (1986.
Kohler, et al. Continuous culture of fused cells secreting antibody of predefined specificity. Nature, 256:495 (1975).
Koide et al. Monobodies: antibody mimics based on the scaffold of the fibronectin type III domain. Methods Mol. Biol. 352: 95-109 (2007).
Krejembrink, et al. Artificial Binding Proteins (Affitins) as Probes for Conformational Changes in Secretin PulD. J. Mol. Biol. 383 (5): 1058-68 (2008).
Lai, et al. A fusion intermediate gp41 immunogen elicits neutralizing antibodies to HIV-1. J Biol Chem. 289, 29912-29926 (2014).
Lee, JH., et al, Antibodies to a conformational epitope on gp41 neutralize HIV-1 by destabilizing the Env spike, Nat Commun, 2015, 6: 8167.
Lenz, et al. Trimeric Membrane-anchored gp41 Inhibits HIV Membrane Fusion. J. Biol. Chem., 280(6): 4095-4101 (2005).
Lonberg, et al. Antigen-specific human antibodies from mice comprising four distinct genetic modifications. Nature 368 856-859 (1994).
Lonberg, et al. Human antibodies from transgenic mice. Intern. Rev. Immunol. 13 65-93 (1995).
Louis, et al. Covalent Trimers of the Internal N-terminal Trimeric Coiled-coil of gp41 and Antibodies Directed against Them Are Potent Inhibitors of HIV Envelope-mediated Cell Fusion. J. Biol. Chem., 278(22): 20278-85 (2003) (=WO2005/118887A2).
Macallum et al. Antibody-antigen interactions: contact analysis and binding site topography. J. Mol. Biol., 262:732-745 (1996).
Makabe, et al. Thermodynamic Consequences of Mutations in Vernier Zone Residues of a Humanized Anti-human Epidermal Growth Factor Receptor Murine Antibody, 528. J. Biol. Chem. 283: 1156-66.
Marks, et al. By-passing Immunisation. Human Antibodies from V-gene Libraries Displayed on Phage. J. Mol. Biol., 222:581-597 (1991).
Marks, et al. By-passing immunization: building high affinity human antibodies by chain shuffling. Bio/Technology 10, 779-783 (1992).
Modrow, et al. Computer-assisted analysis of envelope protein sequences of seven human immunodeficiency virus Isolates: prediction of antigenic epitopes in conserved and variable regions. J. Virol. 61(2): 570-8 (1987).
Montefiori, D.C. Evaluating Neutralizing Antibodies Against HIV, SIV, and SHIV in Luciferase Reporter Gene Assays. Curr. Protocol. Immunol. Chapter 12, Unit 12.11 (2005).
Montefiori, et al. Magnitude and Breadth of the Neutralizing Antibody Response in the RV144 and Vax003 HIV-1 Vaccine Efficacy Trials. J. Inf. Dis. 206: 431-441 (2012).
Morrison et al., Immunology. Success in specification. Nature, 368, 812-13 (1994).
Nelson, et al. Antibody Elicited Against the gp41 N-Heptad Repeat (NHR) Coiled-Coil Can Neutralize HIV-1 with Modest Potency but Nonneutralizing Antibodies Also Bind to NHR Mimetics. Virol. 377(1): 170-83 (2008).
Neuberger, M., Generating high-avidity human Mabs in mice. Nature Biotechnology 14, 826 (1996).
NIH AIDS Reagent Program, TZM-b1 Cells, Cat. No. 8129 (2015).
Nixon, et al. Engineered protein inhibitors of proteases. Curr. Opin. Drug Discov. Devel. 9 (2): 261-8 (2006).
Nygren, et al. Alternative binding proteins: Affibody binding proteins developed from a small three-helix bundle scaffold. FEBS J. 275 (11): 2668-76 (2008).
Pace, et al. Bispecific antibodies directed to CD4 domain 2 and HIVenvelope exhibit exceptional breadth and picomolar potency against HIV-1. PNAS USA, 110(33): 13540-45 (2013).
PCT/IB2016/057367 International Search Report dated Mar. 28, 2017.
PCT/IB2016/057367 International Preliminary Examination Report.
PCT/IB2016/057367 Written Opinion.
Pietzsch, et al. Anti-gp41 Antibodies Cloned from HIV-Infected Patients with Broadly Neutralizing Serologic Activity. J. Virol. 84(10): 5032-5042 (2010).
Presta, L. Antibody engineering. Curr. Op. Stud. Biol., 2:593-596 (1992).
Riechmann, et al. Reshaping human antibodies for therapy. Nature, 332:323-329 (1988).
Rudikoff, S., et al., Single amino acid substitution altering antigen-biding specificity, PNAS USA, 1982; 79: 1979-1983.
Sanders, et al. A next-generation cleaved, soluble HIV-1 Env trimer, BG505 SOSIP.664 gp140, expresses multiple epitopes for broadly neutralizing but not non-neutralizing antibodies. PLoS Pathog. 9, e1003618 (2013).
Scharf, L., et al., Antibody 8ANC195 Reveals a Site of Broad Vulnerability on the HIV-1 Envelope Spike, Cell Reports, 2014, 7(3), 785-795.
Scharf, L., et al., Broadly Neutralizing Antibody 8ANC195 Recognizes Closed and Open States of HIV-1 Env, Cell, 2015; 162(6):1379-1390.
Scheid, J., Broad diversity of neutralizing antibodies isolated from memory B cells in HIV-infected individuals, Nature, 2009; 458: 636-640.
Seaman, et al. Tiered Categorization of a Diverse Panel of HIV-1 Env Pseudoviruses for Assessment of Neutralizing Antibodies. J. Virol. 84(3): 1439-52 (2010).

(56) References Cited

OTHER PUBLICATIONS

Silverman, et al. Multivalent avimer proteins evolved by exon shuffling of a family of human receptor domains. Nat. Eliotechnol. 23 (12): 1556-61 (2005).

Skerra, A. Alternative binding proteins: anticalins—harnessing the structural plasticity of the lipocalin ligand pocket to engineer novel binding activities. FEBS J. 275 (11): 2677-83 (2008).

Stumpp, et al. DARPins: A new generation of protein therapeutics. Drug Discov. Today 13 (15-16): 695-701 (2008).

Teeuwsen, et al. Production and characterization of a human monoclonal antibody reactive with a conserved epitope on gp41 of human immunodeficiency virus type I. AIDS Res. Hum. Retroviruses 6: 381-392 (1990).

Tomaras, et al. Polyclonal B cell responses to conserved neutralization epitopes in a subset of HIV-1-infected individuals. J Virol 85, 11502-11519 (2011).

Verhoeyen, et al. Reshaping Human Antibodies: Grafting an Antilysozyme Activity. Science, 239:1534-1536 (1988).

Wibmer, CK., et al., Structure and Recognition of a Novel HIV-1 gp120-gp41 Interface Antibody that Caused MPER Exposure through Viral Escape, PLoS Pathog, 2017; 13(1):e1006074.

Zhang MY. et al., Identification and Characterization of a Broadly Cross-Reactive HIV-1 Human Monoclonal Antibody That Binds to Both gp120 and gp41, PLoS One, 2012; 7(9), e44241.

Zwick, et al. Broadly Neutralization Antibodies Targeted to the Membrane-Proximal External Region of Human Immunodeficiency Virus Type I Glycoprotein gp41. J. Virol. 75(22): 10892-10905 (2001).

Zhu, et al. Cross-Reactive HIV-1-Neutralizing Human Monoclonal Antibodies Identified from a Patient with 2F5-Like Antibodies. Journal of Virology, Nov. 2011, p. 11401-11408.

Zhu, et al. Author's Correction. Cross-Reactive HIV-1-Neutralizing Human Monoclonal Antibodies Identified from a Patient with 2F5-Like Antibodies. Journal of Virology, Nov. 2013, p. 13936.

\* cited by examiner

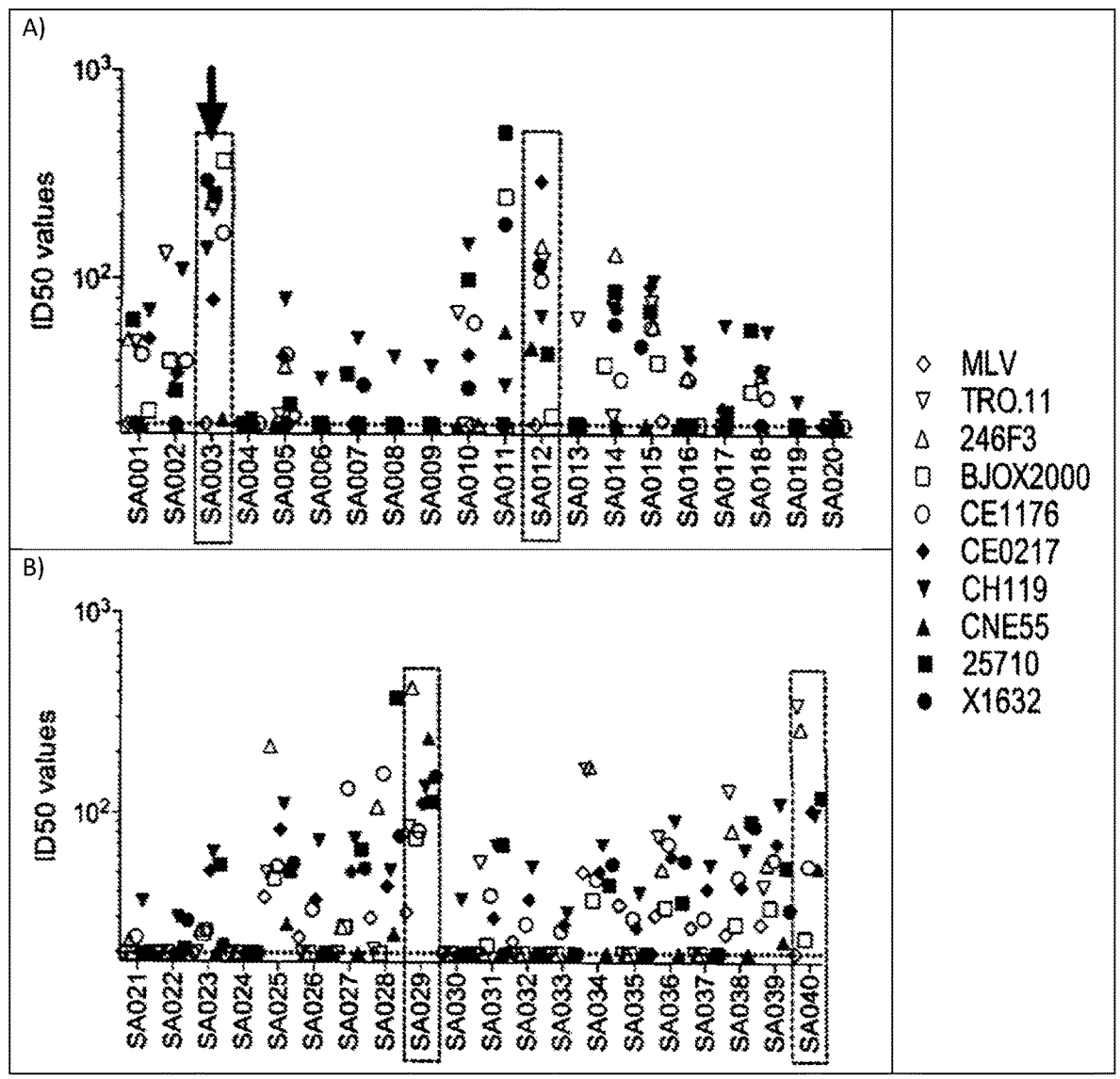
FIGURE 1A-B

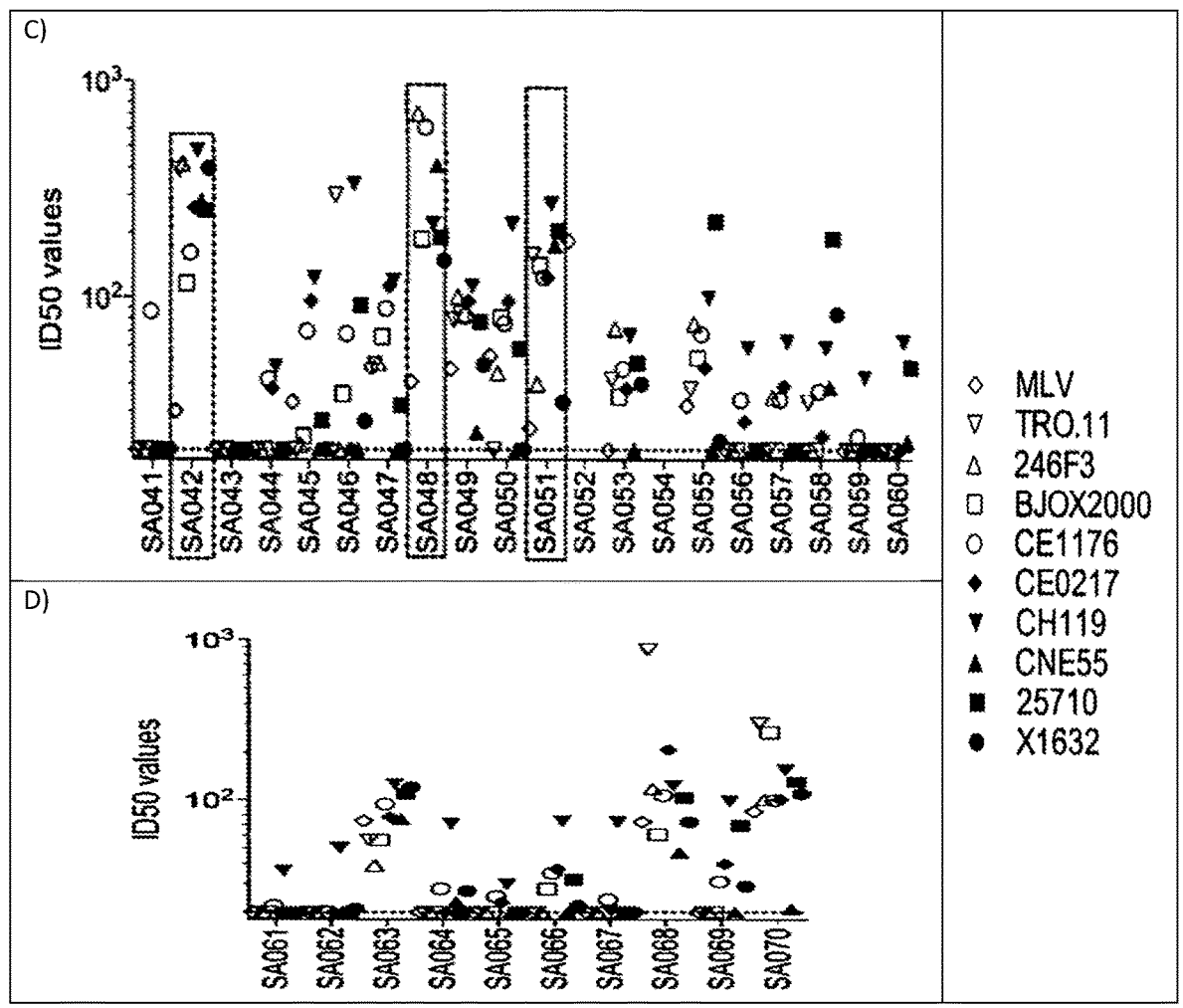

FIGURE 4

| Virus ID | Clade* | IC50 LN01 |
|---|---|---|
| 6535.3 | B | 1.031 |
| QH0692.42 | B | 0.515 |
| SC422661.8 | B | 0.292 |
| PVO.4 | B | 0.403 |
| TRO.11 | B | 0.185 |
| AC10.0.29 | B | 1.694 |
| RHPA4259.7 | B | 10.306 |
| THRO4156.18 | B | 9.831 |
| REJO4541.67 | B | 0.291 |
| TRJO4551.58 | B | 8.416 |
| WITO4160.33 | B | 0.224 |
| CAAN5342.A2 | B | 2.242 |
| WEAU_d15_410_5017 | B (T/F) | 2.471 |
| 1006_11_C3_1601 | B (T/F) | 0.548 |
| 1054_07_TC4_1499 | B (T/F) | 0.092 |
| 1056_10_TA11_1826 | B (T/F) | 0.060 |
| 1012_11_TC21_3257 | B (T/F) | 0.641 |
| 6240_08_TA5_4622 | B (T/F) | 1.978 |
| 6244_13_B5_4576 | B (T/F) | 0.088 |
| 62357_14_D3_4589 | B (T/F) | 5.043 |
| SC05_8C11_2344 | B (T/F) | 0.710 |
| Du156.12 | C | 0.146 |
| Du172.17 | C | 0.059 |
| Du422.1 | C | 0.929 |
| ZM197M.PB7 | C | 0.127 |
| ZM214M.PL15 | C | 0.840 |
| ZM233M.PB6 | C | 0.673 |
| ZM249M.PL1 | C | 0.944 |
| ZM53M.PB12 | C | 11.114 |
| ZM109F.PB4 | C | 0.618 |
| ZM135M.PL10a | C | 0.710 |
| CAP45.2.00.G3 | C | 1.878 |
| CAP210.2.00.E8 | C | >25 |
| HIV-001428-2.42 | C | 24.689 |
| HIV-0013095-2.11 | C | 0.028 |
| HIV-16055-2.3 | C | 0.174 |
| HIV-16845-2.22 | C | 0.040 |
| Ce1086_B2 | C (T/F) | 0.328 |
| Ce0393_C3 | C (T/F) | >25 |
| Ce1176_A3 | C (T/F) | 1.092 |
| Ce2010_F5 | C (T/F) | 11.611 |
| Ce0682_E4 | C (T/F) | 0.626 |
| Ce1172_H1 | C (T/F) | 0.070 |
| Ce2060_G9 | C (T/F) | 4.050 |
| Ce703010054_2A2 | C (T/F) | 1.703 |
| BF1266.431a | C (T/F) | >25 |
| 246F_C1G | C (T/F) | 4.894 |
| 249M_B10 | C (T/F) | 2.769 |
| ZM247v1(Rev-) | C (T/F) | 0.501 |
| 7030102001E5(Rev-) | C (T/F) | 4.385 |
| 1394C9G1(Rev-) | C (T/F) | 5.964 |
| Ce704809221_1B3 | C (T/F) | 3.078 |
| 3016.v5.c45 | D | 0.250 |
| A07412M1.vrc12 | D | 0.326 |
| 231965.c01 | D | 9.503 |
| 231966.c02 | D | 0.948 |
| 191821_E6_1 | D (T/F) | 1.239 |

| Virus ID | Clade* | IC50 LN01 |
|---|---|---|
| CNE19 | BC | 1.206 |
| CNE20 | BC | 0.018 |
| CNE21 | BC | 0.053 |
| CNE17 | BC | 1.112 |
| CNE30 | BC | 0.597 |
| CNE52 | BC | >25 |
| CNE53 | BC | 0.321 |
| CNE58 | BC | 0.297 |
| MS208.A1 | A | >25 |
| Q23.17 | A | 5.513 |
| Q461.e2 | A | 2.829 |
| Q769.d22 | A | 6.420 |
| Q259.d2.17 | A | 8.498 |
| Q842.d12 | A | 7.934 |
| 0330.v4.c3 | A | 8.243 |
| 0260.v5.c36 | A | >25 |
| 191955_A11 | A (T/F) | 1.668 |
| 191084_B7-19 | A (T/F) | 2.814 |
| 9004SS_A3_4 | A (T/F) | 0.409 |
| T257-31 | CRF02_AG | 21.964 |
| 928-28 | CRF02_AG | 0.086 |
| 263-8 | CRF02_AG | 0.355 |
| T250-4 | CRF02_AG | 2.202 |
| T251-18 | CRF02_AG | >25 |
| T278-50 | CRF02_AG | 5.102 |
| T255-34 | CRF02_AG | 0.277 |
| 211-9 | CRF02_AG | 0.583 |
| 235-47 | CRF02_AG | 0.874 |
| 620345.c01 | CRF01_AE | 1.547 |
| CNE8 | CRF01_AE | 0.028 |
| C1080.c03 | CRF01_AE | 0.124 |
| R2184.c04 | CRF01_AE | 0.890 |
| R1166.c01 | CRF01_AE | 0.603 |
| R3265.c06 | CRF01_AE | 3.139 |
| C2101.c01 | CRF01_AE | 0.739 |
| C3347.c11 | CRF01_AE | 0.901 |
| C4118.c09 | CRF01_AE | 2.022 |
| CNE5 | CRF01_AE | 4.345 |
| BJOX009000.02.4 | CRF01_AE | 1.212 |
| BJOX015000.11.5 | CRF01_AE (T/F) | 0.529 |
| BJOX010000.06.2 | CRF01_AE (T/F) | 0.353 |
| BJOX025000.01.1 | CRF01_AE (T/F) | 0.186 |
| BJOX028000.10.3 | CRF01_AE (T/F) | 1.097 |
| X1193_c1 | G | 0.851 |
| P0402_c2_11 | G | 3.836 |
| X1254_c3 | G | 3.005 |
| X2088_c9 | G | >25 |
| X2131_C1_B5 | G | 0.229 |
| P1981_C5_3 | G | 0.115 |
| X1632_S2_B10 | G | 1.846 |
| 3817.v2.c59 | CD | 14.639 |
| 6480.v4.c25 | CD | 6.271 |
| 6952.v1.c20 | CD | 0.168 |
| 6811.v7.c18 | CD | 5.092 |
| 89-F1_2_25 | CD | 3.043 |
| 3301.v1.c24 | AC | 7.543 |
| 6041.v3.c23 | AC | 1.720 |
| 6540.v4.c1 | AC | 3.885 |
| 6545.v4.c1 | AC | 2.977 |
| 0815.v3.c3 | ACD | 0.384 |
| 3103.v3.c10 | ACD | >25 |

| IC50 (ug/ml) in TZM-bl cells | | 656- | 661- | 666- | 671- | 676- | 681- | 686- |
|---|---|---|---|---|---|---|---|---|
| virus | LN01 | | | | | | | |
| Clade B HIV-1 | | NEQELLALDKWASLWNWFDITKWLWYIKIFIMIV | | | | | | |
| HIV-2/7312A | >25 | NMYELQKLNSWDVFGNWFDLASWVKYIQYGVYIV | | | | | | |
| HIV-2/7312A.C1C | <0.011 | -----LA-D---KNLW----ITK-LW---K------ | | | | | | |
| HIV-2/7312A.C3 | >25 | -----LA-DK-ASLW------------------- | | | | | | |
| HIV-2/7312A.C4 | <0.011 | -------------------ITK-LW---K------ | | | | | | |
| HIV-2/7312A.C6 | >25 | ---------------------IT---I-------- | | | | | | |
| HIV-2/7312A.C7 | >25 | ------A-DKWA---------------------- | | | | | | |
| HIV-2/7312A.C8 | <0.011 | -----------SLW----ITK-LW---K------ | | | | | | |

FIGURE 8A-B
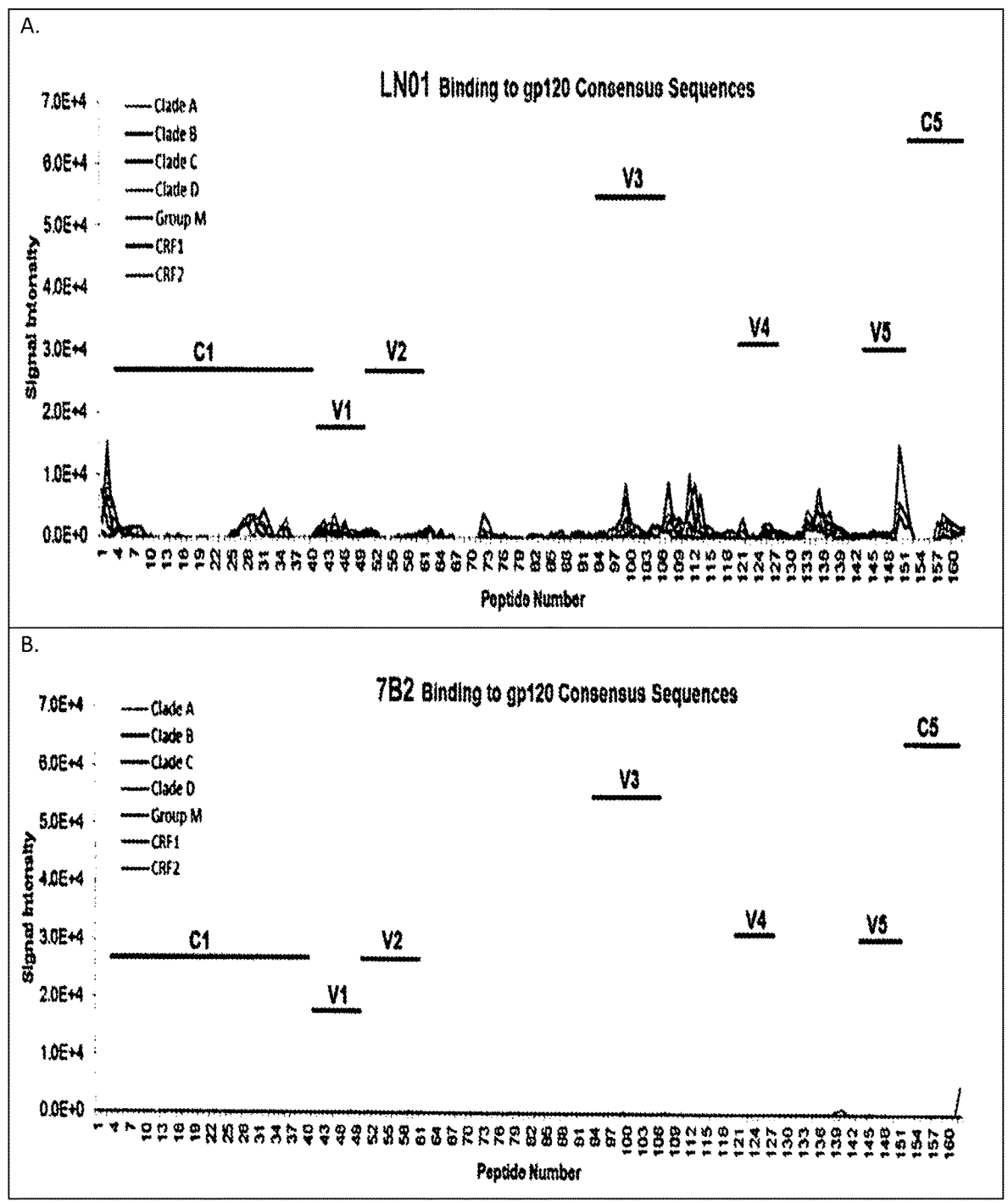

FIGURE 8C-D
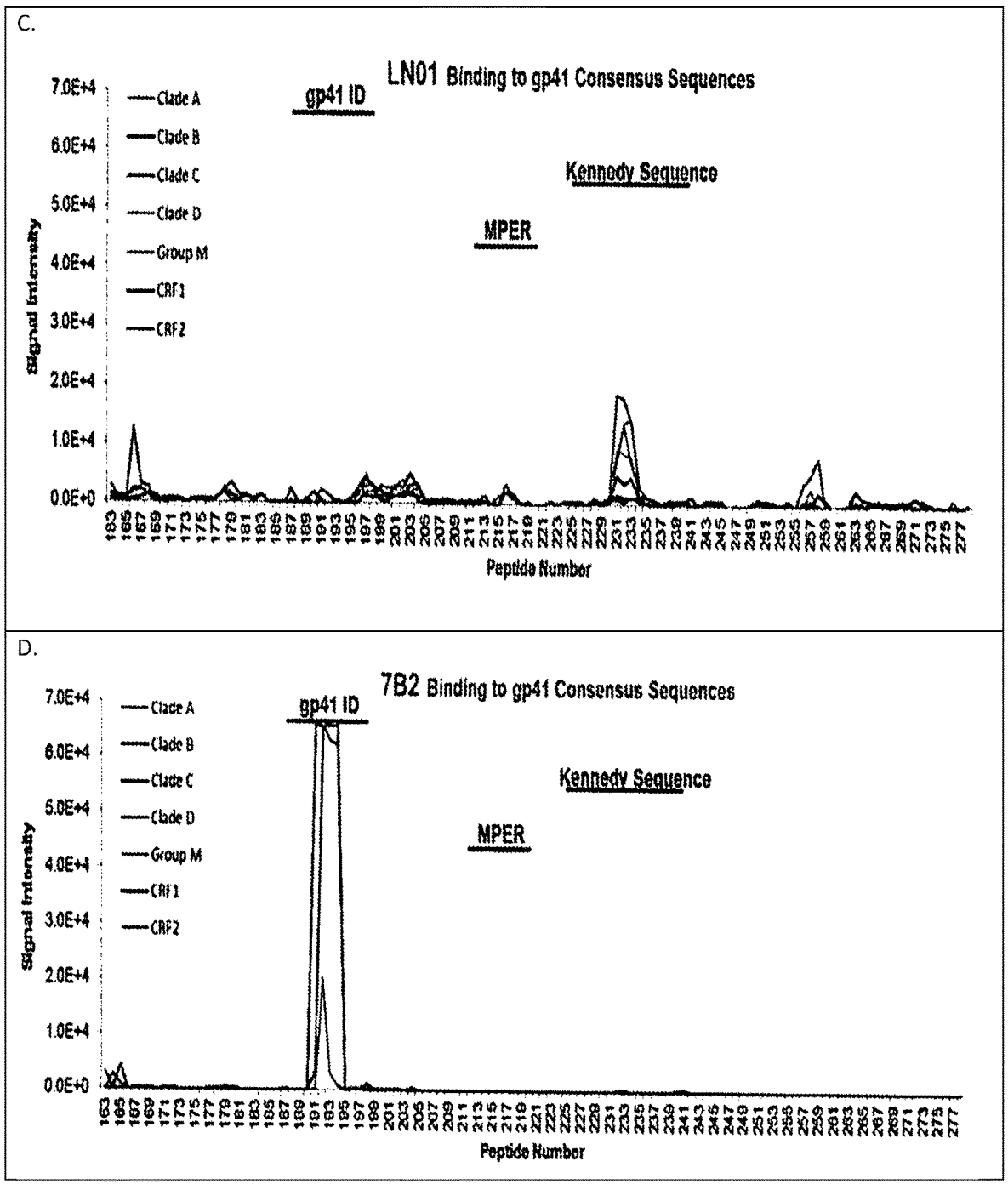

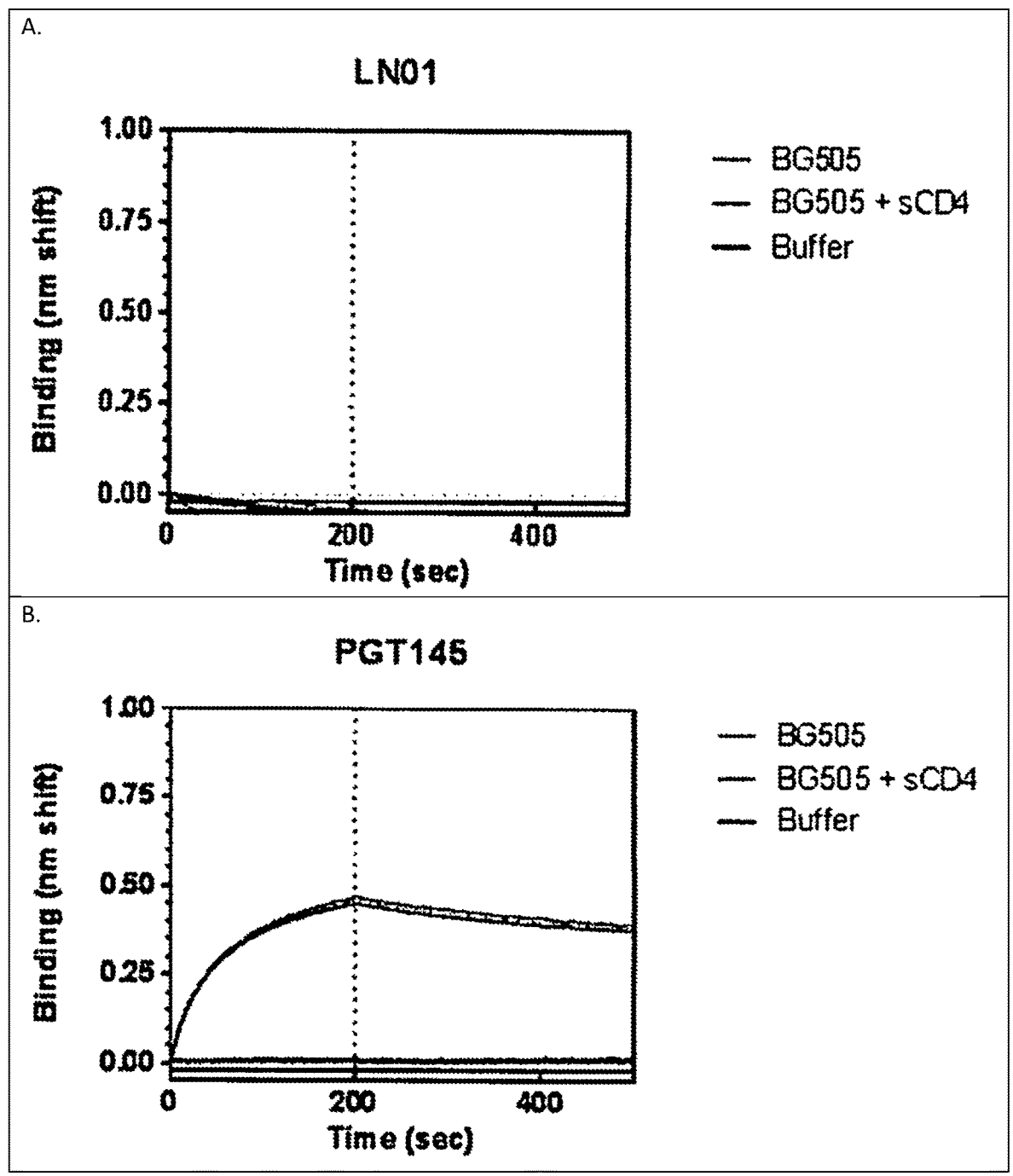
FIGURE 9A-B

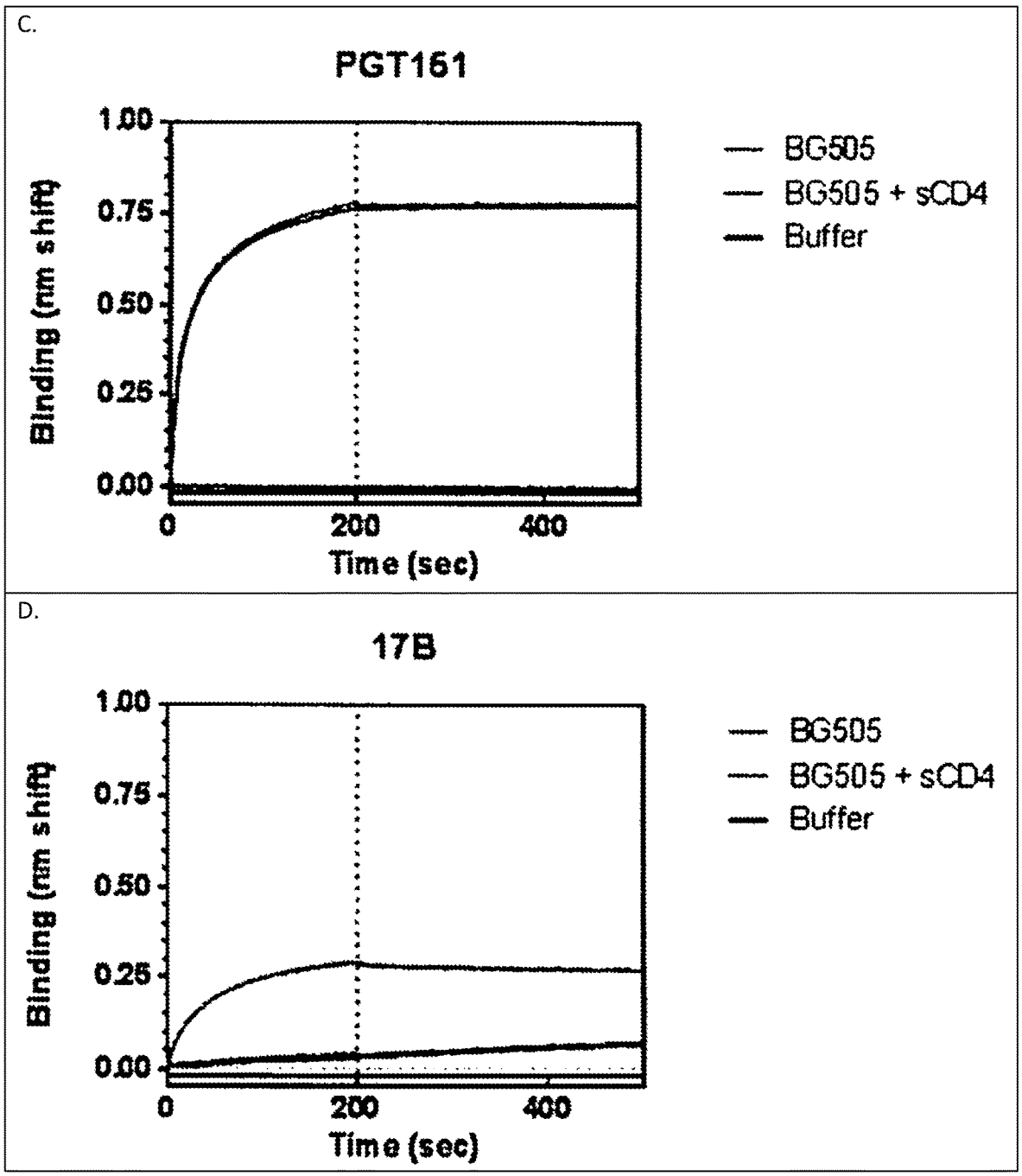

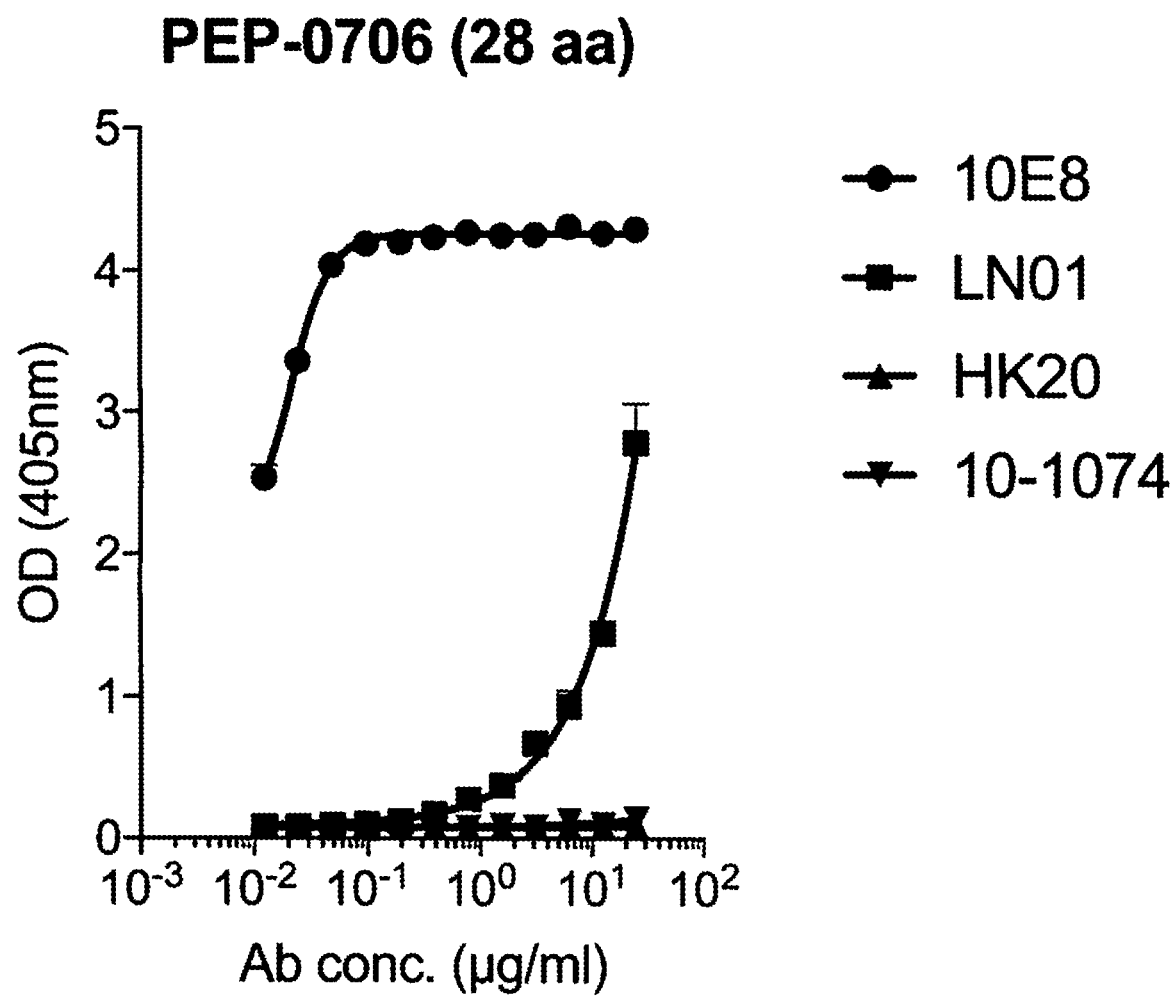

FIGURE 13A

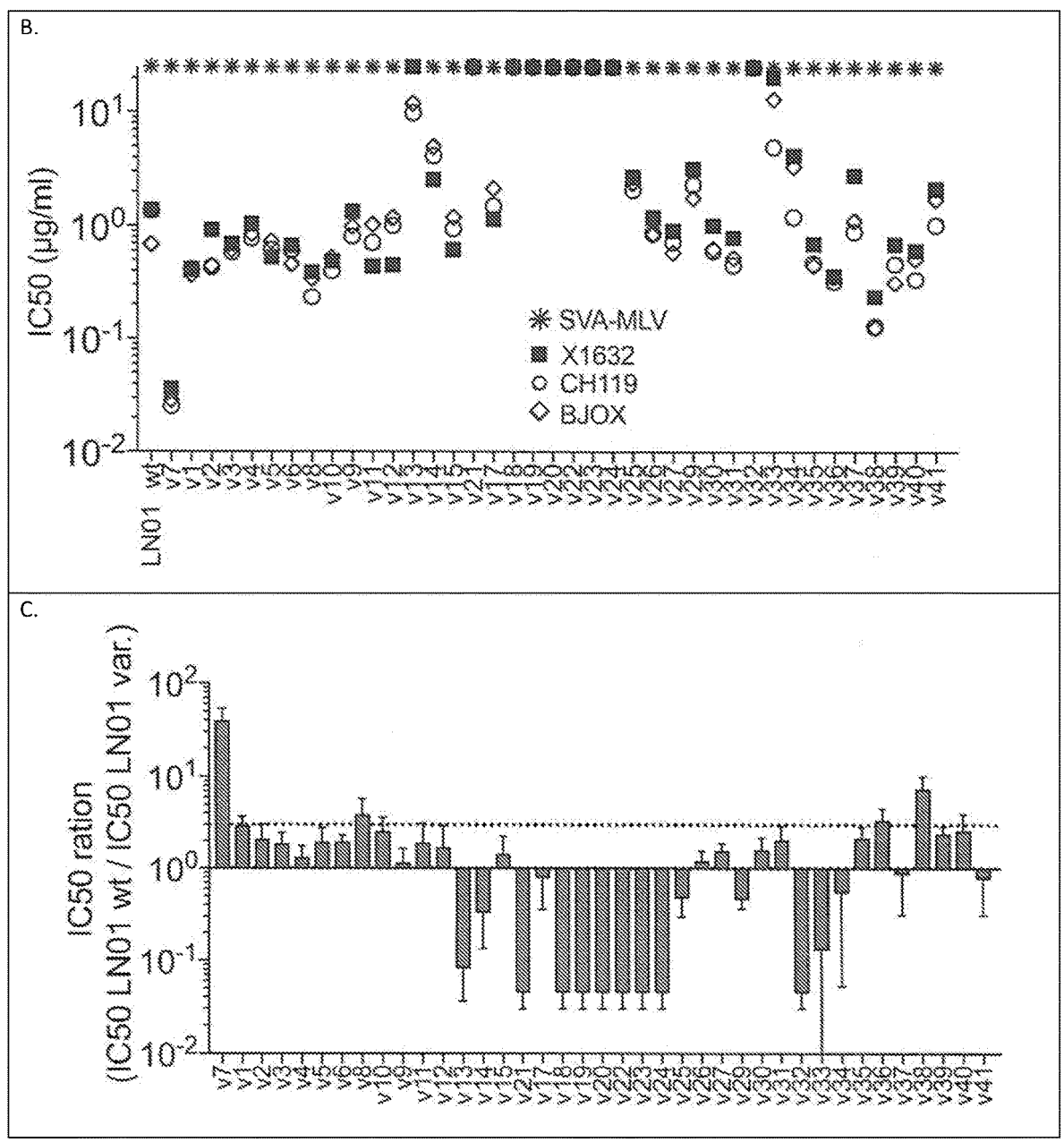
FIGURE 13B-C

FIGURE 14A-D
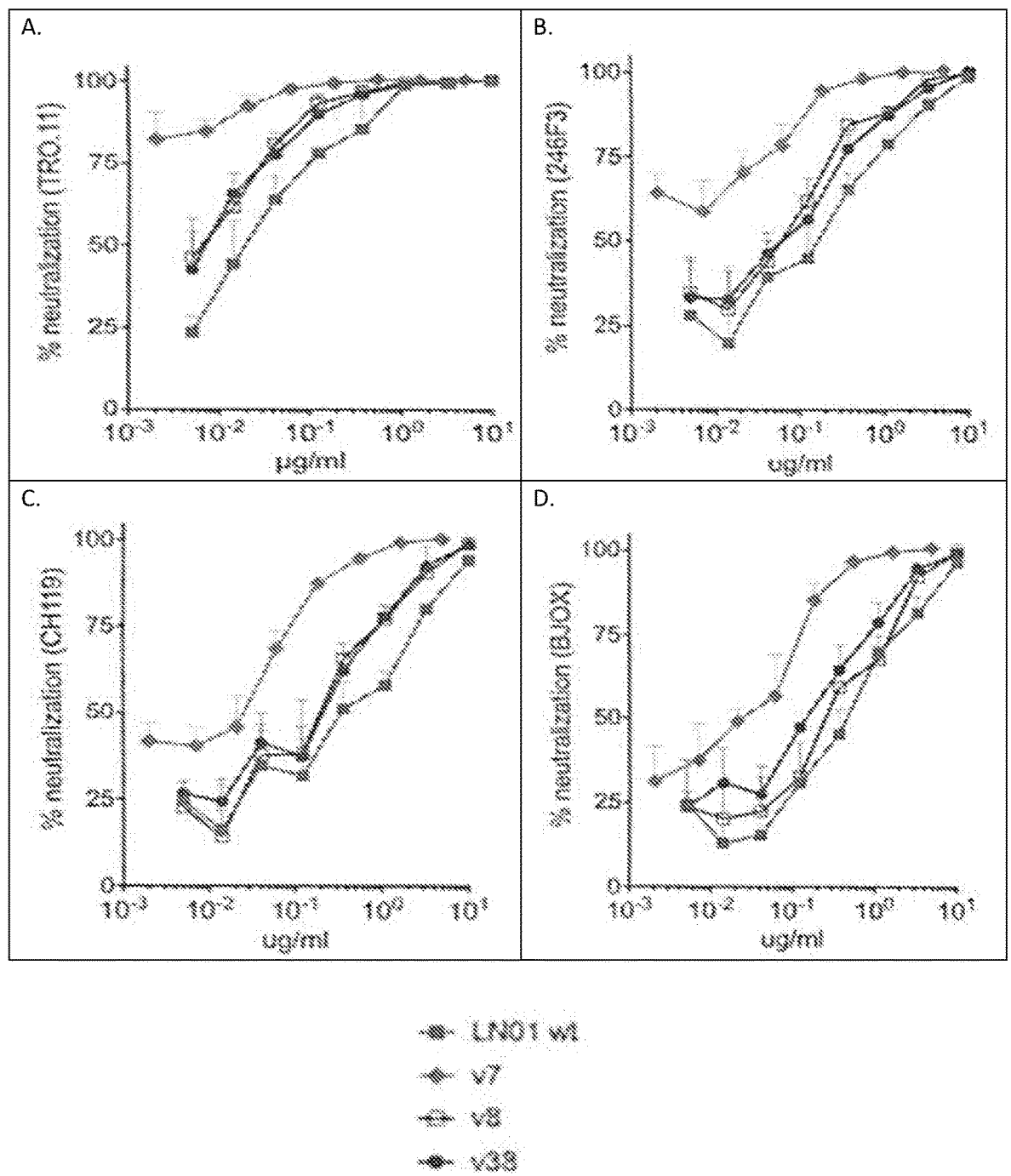

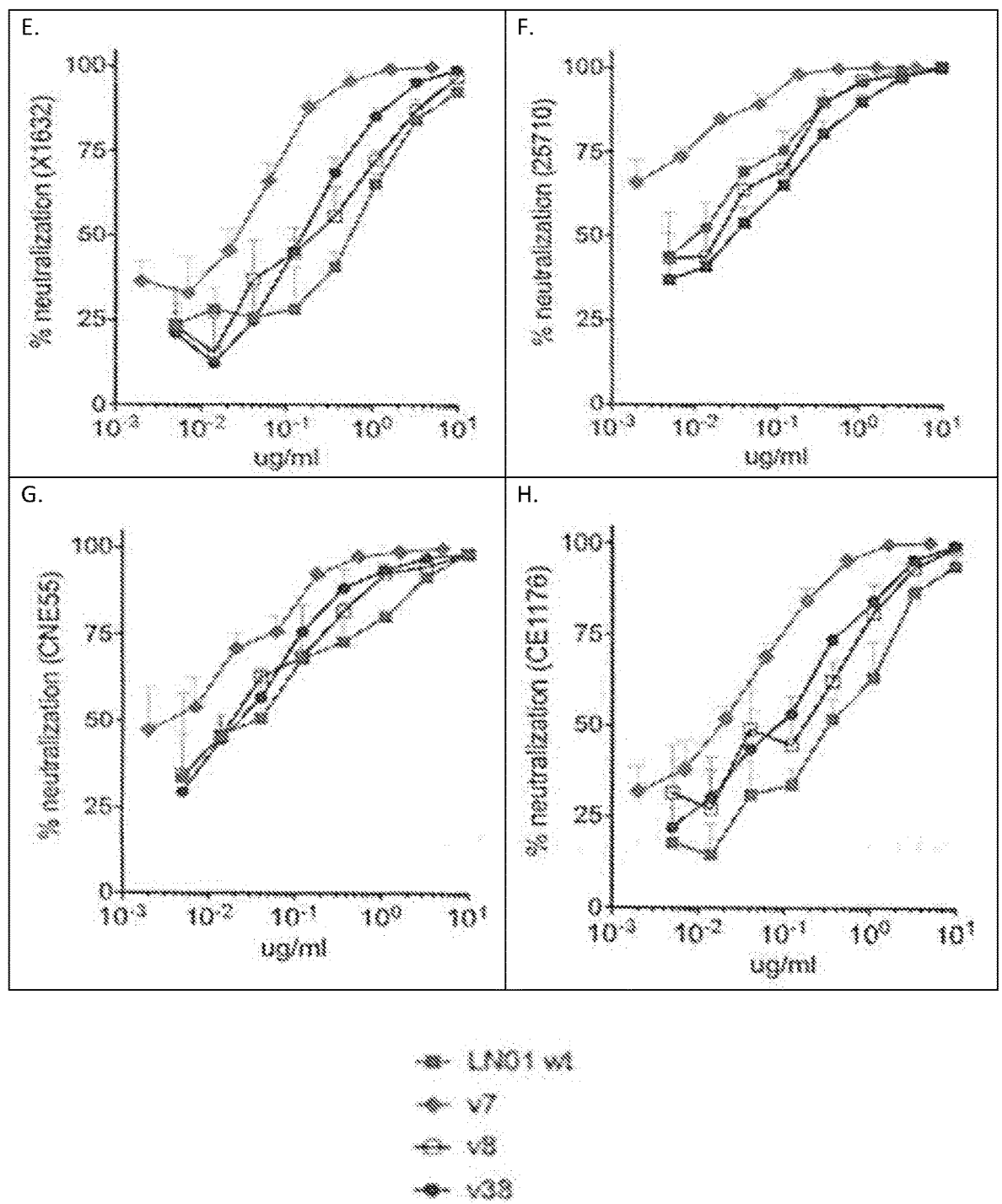
FIGURE 14E-H

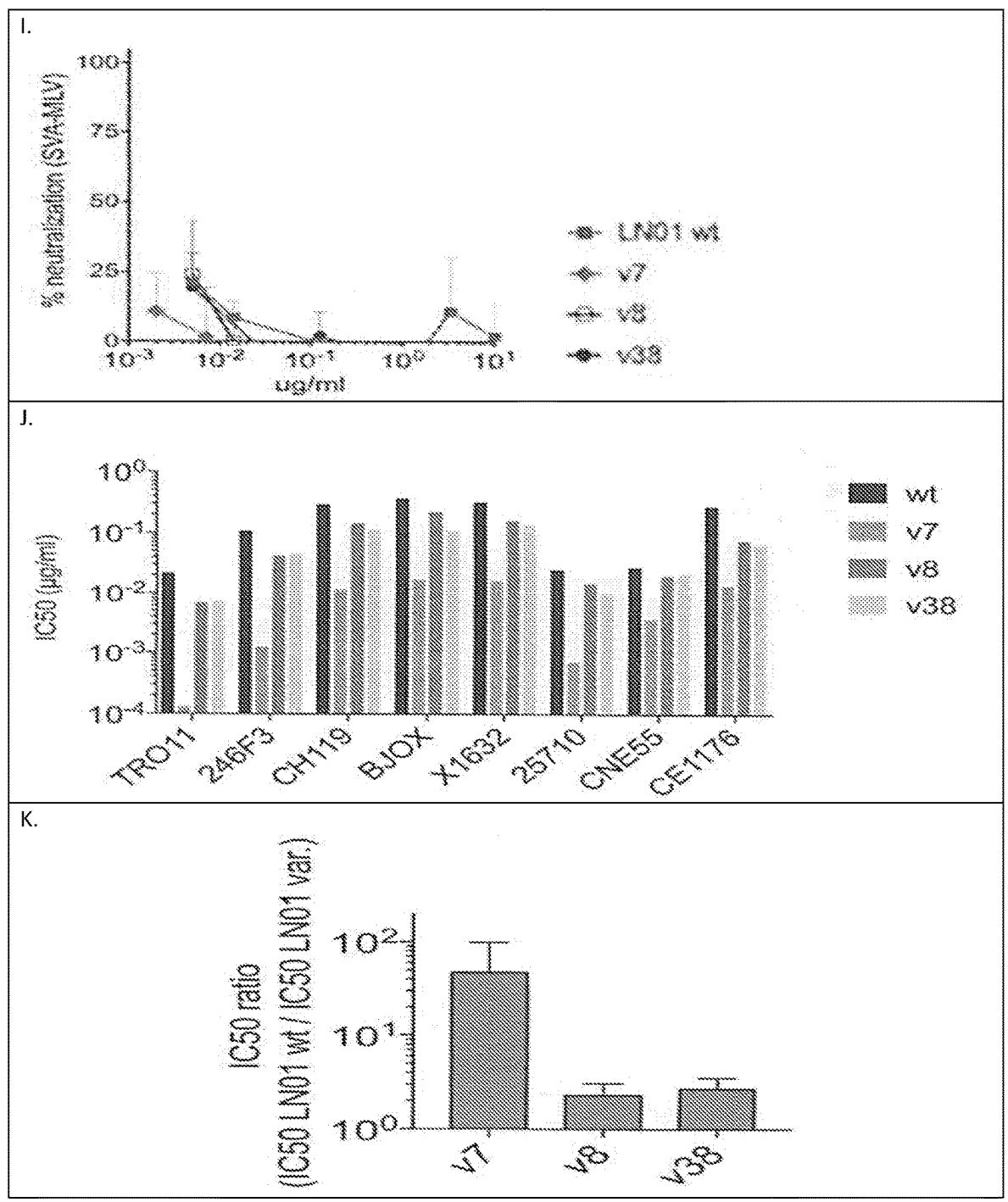
FIGURE 14I-K

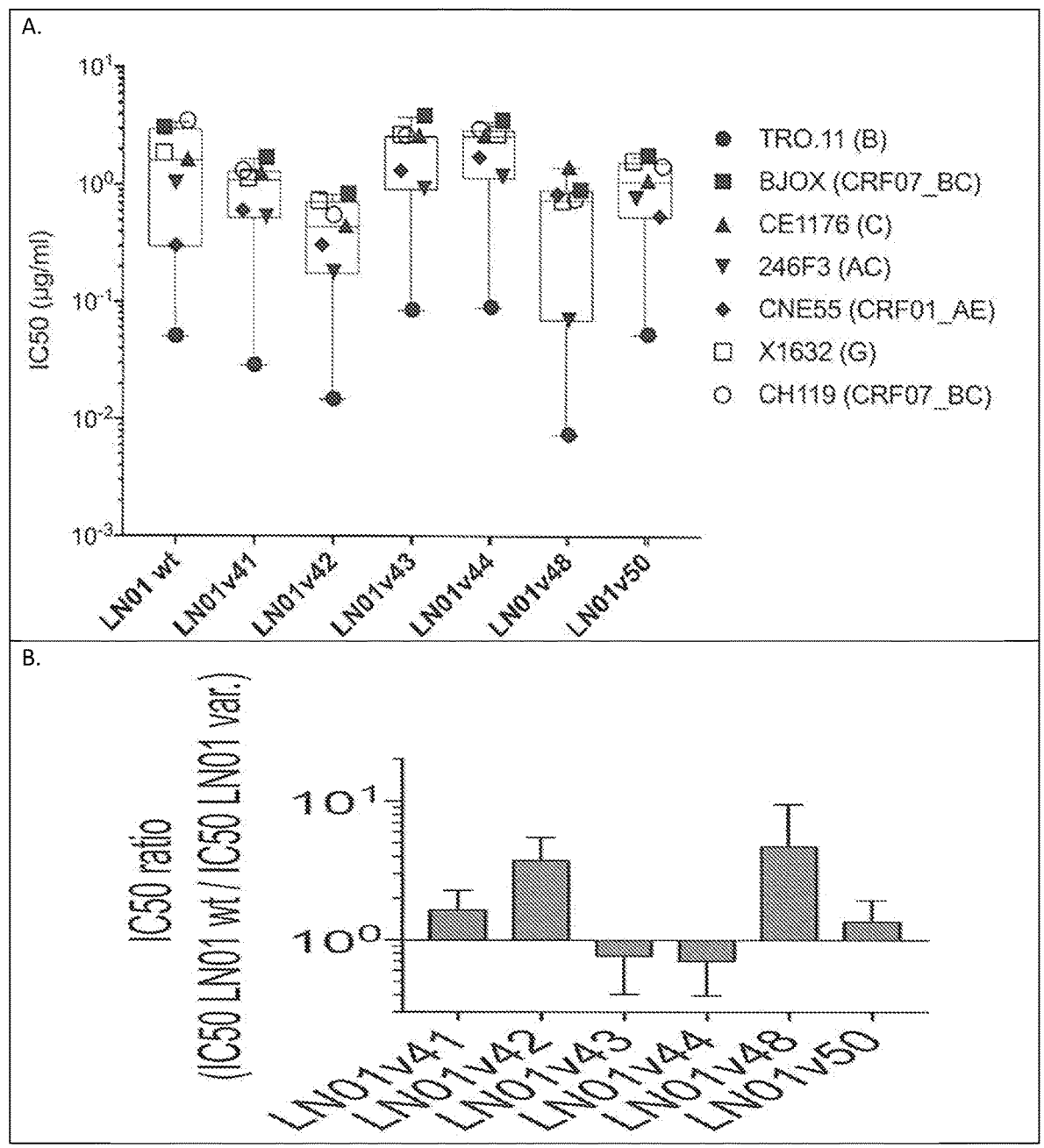
FIGURE 15A-B

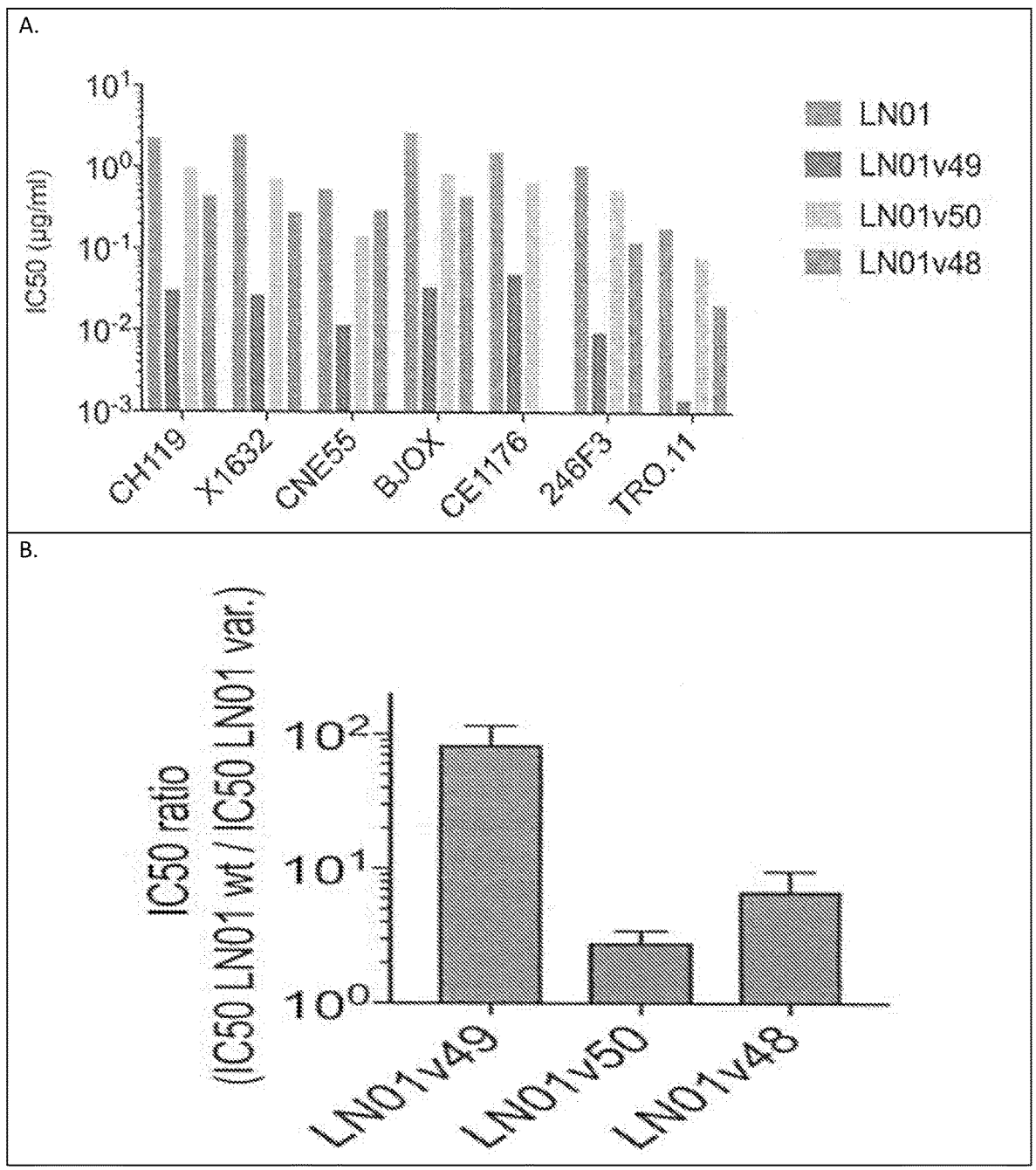
FIGURE 16A-B

SEQUENCE LISTING

```
<160> NUMBER OF SEQ ID NOS: 82

<210> SEQ ID NO 1
<211> LENGTH: 10
<212> TYPE: PRT
<213> ORGANISM: Homo sapiens

<400> SEQUENCE: 1

Gly Asp Ser Val Ser Asn Asp Asn Tyr Tyr
1               5                   10

<210> SEQ ID NO 2
<211> LENGTH: 7
<212> TYPE: PRT
<213> ORGANISM: Homo sapiens

<400> SEQUENCE: 2

Ile Tyr Tyr Ser Gly Thr Thr
1               5

<210> SEQ ID NO 3
<211> LENGTH: 20
<212> TYPE: PRT
<213> ORGANISM: Homo sapiens

<400> SEQUENCE: 3
```

-continued

Val Arg Met Pro Ser His Gly Phe Trp Ser Thr Ser Phe Ser Tyr Trp
1               5                   10                  15

Tyr Phe Asp Leu
            20

<210> SEQ ID NO 4
<211> LENGTH: 6
<212> TYPE: PRT
<213> ORGANISM: Homo sapiens

<400> SEQUENCE: 4

Gln Ser Val Thr Lys Tyr
1               5

<210> SEQ ID NO 5
<211> LENGTH: 9
<212> TYPE: PRT
<213> ORGANISM: Homo sapiens

<400> SEQUENCE: 5

Leu Ile Tyr Gly Thr Tyr Thr Leu Leu
1               5

<210> SEQ ID NO 6
<211> LENGTH: 9
<212> TYPE: PRT
<213> ORGANISM: Homo sapiens

<400> SEQUENCE: 6

Gln Gln Ala His Ser Thr Pro Trp Thr
1               5

<210> SEQ ID NO 7
<211> LENGTH: 128
<212> TYPE: PRT
<213> ORGANISM: Homo sapiens

<400> SEQUENCE: 7

Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Asp
            20                  25                  30

Asn Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
    50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
                85                  90                  95

Cys Val Arg Met Pro Ser His Gly Phe Trp Ser Thr Ser Phe Ser Tyr
            100                 105                 110

Trp Tyr Phe Asp Leu Trp Gly Arg Gly His Phe Val Ala Val Ser Trp
        115                 120                 125

<210> SEQ ID NO 8
<211> LENGTH: 107
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
            85                  90                  95

Thr Phe Gly Gln Gly Thr His Val Ala Ala Asn
            100                 105

<210> SEQ ID NO 9
<211> LENGTH: 128
<212> TYPE: PRT
<213> ORGANISM: Homo sapiens

<400> SEQUENCE: 9

Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Trp
            20                  25                  30

Asn Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
    50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
            85                  90                  95

Cys Val Arg Met Pro Ser His Gly Phe Trp Ser Thr Ser Phe Ser Tyr
            100                 105                 110

Trp Tyr Phe Asp Leu Trp Gly Arg Gly His Phe Val Ala Val Ser Trp
        115                 120                 125

<210> SEQ ID NO 10
<211> LENGTH: 107
<212> TYPE: PRT
<213> ORGANISM: Homo sapiens

<400> SEQUENCE: 10

Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
            85                  90                  95

Thr Phe Gly Gln Gly Thr His Val Ala Ala Asn
            100                 105

<210> SEQ ID NO 11
<211> LENGTH: 128
<212> TYPE: PRT
<213> ORGANISM: Homo sapiens

<400> SEQUENCE: 11

Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Asp
            20                  25                  30

Trp Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
    50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
                85                  90                  95

Cys Val Arg Met Pro Ser His Gly Phe Trp Ser Thr Ser Phe Ser Tyr
            100                 105                 110

Trp Tyr Phe Asp Leu Trp Gly Arg Gly His Phe Val Ala Val Ser Trp
        115                 120                 125

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
                85                  90                  95

Thr Phe Gly Gln Gly Thr His Val Ala Ala Asn
            100                 105

<210> SEQ ID NO 13
<211> LENGTH: 128
<212> TYPE: PRT
<213> ORGANISM: Homo sapiens

<400> SEQUENCE: 13

Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Asp
            20                  25                  30

Asn Tyr Tyr Trp Ala Trp Ile Arg Gln Thr Pro Gly Arg Glu Leu Gln

```
                 35                   40                   45
Val Ile Gly Thr Ile Tyr Tyr Ser Gly Thr Thr Tyr Tyr Asn Pro Ser
         50                      55                      60

Leu Arg Asn Arg Val Thr Ile Ser Leu Asp Lys Ser Val Asn Val Val
 65                      70                      75                  80

Ser Leu Arg Leu Gly Ser Val Ser Ala Ala Asp Thr Ala Gln Tyr Tyr
                 85                      90                      95

Cys Val Arg Met Pro Ser His Gly Phe Trp Ser Thr Phe Ser Tyr
                 100                     105                     110

Trp Tyr Phe Asp Leu Trp Gly Arg Gly His Phe Val Ala Val Ser Trp
             115                     120                     125
```

<210> SEQ ID NO 14
<211> LENGTH: 107
<212> TYPE: PRT
<213> ORGANISM: Homo sapiens

<400> SEQUENCE: 14

```
Asp Ile Gln Met Thr Gln Ser Pro Ser Ser Leu Ser Ala Ser Val Gly
 1               5                   10                  15

Asp Lys Val Thr Ile Thr Cys Arg Ala Ser Gln Ser Val Thr Lys Tyr
                 20                  25                  30

Leu Asn Trp Tyr Gln Phe Lys Thr Gly Gln Ala Pro Arg Ile Leu Ile
             35                  40                  45

Tyr Gly Thr Tyr Thr Leu Leu Ser Gly Val Ser Pro Arg Phe Ser Gly
         50                  55                  60

Ala Gly Trp Gly Ser Leu Tyr Thr Leu Thr Ile Thr Asn Ile Gln Pro
 65                  70                  75                  80

Glu Asp Phe Ala Thr Tyr Tyr Cys Gln Gln Ala His Ser Thr Pro Trp
                 85                  90                  95

Thr Phe Gly Gln Gly Thr His Val Ala Ala Asn
                 100                 105
```

<210> SEQ ID NO 15
<211> LENGTH: 128
<212> TYPE: PRT
<213> ORGANISM: Homo sapiens

<400> SEQUENCE: 15

```
Glu Val Gln Leu Val Glu Ser Gly Pro Gly Leu Val Gln Pro Trp Gly
 1               5                   10                  15

Thr Leu Ser Leu Thr Cys Arg Val Ser Gly Asp Ser Val Ser Asn Phe
                 20                  25                  30

Asn Tyr Tyr Trp Ala Trp Ile Arg Gln Thr Pro Gly Arg Glu Leu Gln
             35                  40                  45

Val Ile Gly Thr Ile Tyr Tyr Ser Gly Thr Thr Tyr Tyr Asn Pro Ser
         50                  55                  60

Leu Arg Asn Arg Val Thr Ile Ser Leu Asp Lys Ser Val Asn Val Val
 65                  70                  75                  80

Ser Leu Arg Leu Gly Ser Val Ser Ala Ala Asp Thr Ala Gln Tyr Tyr
                 85                  90                  95

Cys Val Arg Met Pro Ser His Gly Phe Trp Ser Thr Phe Ser Tyr
                 100                 105                 110

Trp Tyr Phe Asp Leu Trp Gly Arg Gly His Phe Val Ala Val Ser Trp
             115                 120                 125
```

-continued

```
<210> SEQ ID NO 16
<211> LENGTH: 107
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
                85                  90                  95

Thr Phe Gly Gln Gly Thr His Val Ala Ala Asn
            100                 105

<210> SEQ ID NO 17
<211> LENGTH: 128
<212> TYPE: PRT
<213> ORGANISM: Homo sapiens

<400> SEQUENCE: 17

Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Tyr
            20                  25                  30

Asn Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
    50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
                85                  90                  95

Cys Val Arg Met Pro Ser His Gly Phe Trp Ser Thr Ser Phe Ser Tyr
            100                 105                 110

Trp Tyr Phe Asp Leu Trp Gly Arg Gly His Phe Val Ala Val Ser Trp
        115                 120                 125

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60
```

```
Ala Gly Ser Gly Ser Leu Tyr Thr Leu Thr Ile Thr Asn Ile Gln Pro
 65                  70                  75                  80

Glu Asp Phe Ala Thr Tyr Tyr Cys Gln Gln Ala His Ser Thr Pro Trp
             85                  90                  95

Thr Phe Gly Gln Gly Thr His Val Ala Ala Asn
            100                 105
```

<210> SEQ ID NO 19
<211> LENGTH: 128
<212> TYPE: PRT
<213> ORGANISM: Homo sapiens

<400> SEQUENCE: 19

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Asp Ser Val Ser Asn Trp
             20                  25                  30

Asn Tyr Tyr Trp Ala Trp Ile Arg Gln Thr Pro Gly Arg Glu Leu Gln
         35                  40                  45

Val Ile Gly Thr Ile Tyr Tyr Ser Gly Thr Thr Tyr Tyr Asn Pro Ser
 50                  55                  60

Leu Arg Asn Arg Val Thr Ile Ser Leu Asp Lys Ser Val Asn Val Val
 65                  70                  75                  80

Ser Leu Arg Leu Gly Ser Val Ser Ala Ala Asp Thr Ala Gln Tyr Tyr
             85                  90                  95

Cys Val Arg Met Pro Ser His Gly Phe Trp Ser Thr Ser Phe Ser Tyr
            100                 105                 110

Trp Tyr Phe Asp Leu Trp Gly Arg Gly Thr Leu Val Thr Val Ser Ser
            115                 120                 125
```

<210> SEQ ID NO 20
<211> LENGTH: 107
<212> TYPE: PRT
<213> ORGANISM: Homo sapiens

<400> SEQUENCE: 20

```
Asp Ile Gln Met Thr Gln Ser Pro Ser Ser Leu Ser Ala Ser Val Gly
  1               5                  10                  15

Asp Lys Val Thr Ile Thr Cys Arg Ala Ser Gln Ser Val Thr Lys Tyr
             20                  25                  30

Leu Asn Trp Tyr Gln Phe Lys Thr Gly Gln Ala Pro Arg Ile Leu Ile
         35                  40                  45

Tyr Gly Thr Tyr Thr Leu Leu Ser Gly Val Ser Pro Arg Phe Ser Gly
 50                  55                  60

Ala Gly Ser Gly Ser Leu Tyr Thr Leu Thr Ile Thr Asn Ile Gln Pro
 65                  70                  75                  80

Glu Asp Phe Ala Thr Tyr Tyr Cys Gln Gln Ala His Ser Thr Pro Trp
             85                  90                  95

Thr Phe Gly Gln Gly Thr His Val Ala Ala Asn
            100                 105
```

<210> SEQ ID NO 21
<211> LENGTH: 128
<212> TYPE: PRT
<213> ORGANISM: Homo sapiens

<400> SEQUENCE: 21

```
Glu Val Gln Leu Val Glu Ser Gly Pro Gly Leu Val Gln Pro Trp Gly
1               5                   10                  15

Thr Leu Ser Leu Thr Cys Arg Val Ser Gly Asp Ser Val Ser Asn Trp
            20                  25                  30

Trp Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
            85                  90                  95

Cys Val Arg Met Pro Ser His Gly Phe Trp Ser Thr Ser Phe Ser Tyr
                100                 105                 110

Trp Tyr Phe Asp Leu Trp Gly Arg Gly His Phe Val Ala Val Ser Trp
            115                 120                 125
```

```
<210> SEQ ID NO 22
<211> LENGTH: 107
<212> TYPE: PRT
<213> ORGANISM: Homo sapiens

<400> SEQUENCE: 22
```

```
Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
            85                  90                  95

Thr Phe Gly Gln Gly Thr His Val Ala Ala Asn
                100                 105
```

```
<210> SEQ ID NO 23
<211> LENGTH: 128
<212> TYPE: PRT
<213> ORGANISM: Homo sapiens

<400> SEQUENCE: 23
```

```
Gln Val Gln Leu Glu Glu Ser Gly Pro Gly Leu Val Gln Pro Trp Gly
1               5                   10                  15

Thr Leu Ser Leu Thr Cys Arg Val Ser Gly Gly Ser Ile Ser Ser Ser
            20                  25                  30

Ser Tyr Tyr Trp Ala Trp Ile Arg Gln Thr Pro Gly Arg Glu Leu Gln
        35                  40                  45

Val Ile Gly Thr Ile Tyr Tyr Ser Gly Thr Thr Tyr Tyr Asn Pro Ser
50                  55                  60

Leu Arg Asn Arg Val Thr Ile Ser Leu Asp Lys Ser Val Asn Val Val
65                  70                  75                  80

Ser Leu Arg Leu Gly Ser Val Ser Ala Ala Asp Thr Ala Gln Tyr Tyr
            85                  90                  95
```

```
Cys Val Arg Met Pro Ser His Gly Phe Trp Ser Thr Ser Phe Ser Tyr
            100                 105                 110

Trp Tyr Phe Asp Leu Trp Gly Arg Gly His Phe Val Ala Val Ser Trp
        115                 120                 125
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Ser Ser Leu Ser Ala Ser Val Gly
1               5                   10                  15

Asp Lys Val Thr Ile Thr Cys Arg Ala Ser Gln Ser Val Thr Lys Tyr
            20                  25                  30

Leu Asn Trp Tyr Gln Phe Lys Thr Gly Gln Ala Pro Arg Ile Leu Ile
        35                  40                  45

Tyr Gly Thr Tyr Thr Leu Leu Ser Gly Val Ser Pro Arg Phe Ser Gly
    50                  55                  60

Ala Gly Ser Gly Ser Leu Tyr Thr Leu Thr Ile Thr Asn Ile Gln Pro
65                  70                  75                  80

Glu Asp Phe Ala Thr Tyr Tyr Cys Gln Gln Ala His Ser Thr Pro Trp
                85                  90                  95

Thr Phe Gly Gln Gly Thr His Val Ala Ala Asn
            100                 105
```

<210> SEQ ID NO 25
<211> LENGTH: 10
<212> TYPE: PRT
<213> ORGANISM: Homo sapiens

<400> SEQUENCE: 25

```
Gly Asp Ser Val Ser Asn Trp Asn Tyr Tyr
1               5                   10
```

<210> SEQ ID NO 26
<211> LENGTH: 10
<212> TYPE: PRT
<213> ORGANISM: Homo sapiens

<400> SEQUENCE: 26

```
Gly Asp Ser Val Ser Asn Asp Trp Tyr Tyr
1               5                   10
```

<210> SEQ ID NO 27
<211> LENGTH: 10
<212> TYPE: PRT
<213> ORGANISM: Homo sapiens

<400> SEQUENCE: 27

```
Gly Asp Ser Val Ser Asn Phe Asn Tyr Tyr
1               5                   10
```

<210> SEQ ID NO 28
<211> LENGTH: 10
<212> TYPE: PRT
<213> ORGANISM: Homo sapiens

<400> SEQUENCE: 28

```
Gly Asp Ser Val Ser Asn Tyr Asn Tyr Tyr
1               5                   10
```

```
<210> SEQ ID NO 29
<211> LENGTH: 10
<212> TYPE: PRT
<213> ORGANISM: Homo sapiens

<400> SEQUENCE: 29

Gly Asp Ser Val Ser Asn Leu Asn Tyr Tyr
1               5                   10

<210> SEQ ID NO 30
<211> LENGTH: 10
<212> TYPE: PRT
<213> ORGANISM: Homo sapiens

<400> SEQUENCE: 30

Gly Asp Ser Val Ser Asn Ile Asn Tyr Tyr
1               5                   10

<210> SEQ ID NO 31
<211> LENGTH: 10
<212> TYPE: PRT
<213> ORGANISM: Homo sapiens

<400> SEQUENCE: 31

Gly Asp Ser Val Ser Asn Trp Trp Tyr Tyr
1               5                   10

<210> SEQ ID NO 32
<211> LENGTH: 9
<212> TYPE: PRT
<213> ORGANISM: Homo sapiens

<400> SEQUENCE: 32

Gly Ser Ile Ser Ser Ser Ser Tyr Tyr
1               5

<210> SEQ ID NO 33
<211> LENGTH: 30
<212> TYPE: DNA
<213> ORGANISM: Homo sapiens

<400> SEQUENCE: 33
ggtgactcag tcagtaatga taattattat                              30

<210> SEQ ID NO 34
<211> LENGTH: 21
<212> TYPE: DNA
<213> ORGANISM: Homo sapiens

<400> SEQUENCE: 34
atctattaca gcggcacaac c                                       21

<210> SEQ ID NO 35
<211> LENGTH: 60
<212> TYPE: DNA
<213> ORGANISM: Homo sapiens

<400> SEQUENCE: 35
gttcgcatgc ccagtcacgg attttggagt acttctttct cttactggta tttcgatctc    60

<210> SEQ ID NO 36
<211> LENGTH: 18
<212> TYPE: DNA
<213> ORGANISM: Homo sapiens
```

<400> SEQUENCE: 36
cagagtgtca ccaaatat                                                          18

<210> SEQ ID NO 37
<211> LENGTH: 27
<212> TYPE: DNA
<213> ORGANISM: Homo sapiens

<400> SEQUENCE: 37
ctcatctatg ggacttatac tttactc                                                27

<210> SEQ ID NO 38
<211> LENGTH: 27
<212> TYPE: DNA
<213> ORGANISM: Homo sapiens

<400> SEQUENCE: 38
caacaggctc acagtactcc ctggacc                                                27

<210> SEQ ID NO 39
<211> LENGTH: 384
<212> TYPE: DNA
<213> ORGANISM: Homo sapiens

<400> SEQUENCE: 39
gaggtgcagc tggtggagtc gggcccagga ctggtgcagc cctgggggac cctgtccctc            60
acctgtcgtg tctctggtga ctcagtcagt aatgataatt attattgggc ctggattcgc           120
cagacccccg ggagggaact gcaggtcatc ggaactatct attacagcgg cacaacctac           180
tacaatccgt cgctcaggaa tcgagtcacg atctcattgg acaagtccgt caatgtggtc           240
tccctgagat tggggtctgt gagtgccgcg gacacggccc aatattattg cgttcgcatg           300
cccagtcacg gattttggag tacttctttc tcttactggt atttcgatct ctggggccgt           360
ggtcatttcg tcgctgtctc ctgg                                                  384

<210> SEQ ID NO 40
<211> LENGTH: 321
<212> TYPE: DNA
<213> ORGANISM: Homo sapiens

<400> SEQUENCE: 40
gacatccaga tgacccagtc tccgtcctcc ctgtctgcct ctgttggaga caaagtcacc            60
atcacctgcc gggccagtca gagtgtcacc aaatatttaa attggtatca gtttaagacc          120
ggccaagccc caagaatcct catctatggg acttatactt tactcagtgg cgtctcgcct          180
cggttcagtg gcgccggatc tggttcactc tacactctga ccatcaccaa tatacagcct          240
gaagacttcg ccacctatta ttgtcaacag gctcacagta ctccctggac cttcggccaa          300
ggaacccacg tggcggccaa c                                                    321

<210> SEQ ID NO 41
<211> LENGTH: 384
<212> TYPE: DNA
<213> ORGANISM: Homo sapiens

<400> SEQUENCE: 41
gaagtgcagc tggtggaatc tggccctggc ctggtgcagc cttggggcac actgagcctg            60
acctgtagag tgtccggcga cagcgtgtcc aactggaact actactgggc ctggatccgg          120

```
cagacccccg gcagagaact gcaagtgatc ggcaccatct actacagcgg cacaacctac    180 tacaaccccca gcctgcggaa cagagtgacc atcagcctgg acaagagcgt gaacgtggtg    240
tccctgagac tgggctctgt gtctgccgcc gataccgccc agtactactg cgtgcggatg    300
cccagccacg gcttctggtc taccagcttc agctactggt acttcgacct gtggggcaga    360
ggccacttcg tggccgtgtc ttgg                                            384

<210> SEQ ID NO 42
<211> LENGTH: 321
<212> TYPE: DNA
<213> ORGANISM: Homo sapiens

<400> SEQUENCE: 42
gacatccaga tgacccagtc tccgtcctcc ctgtctgcct ctgttggaga caaagtcacc     60
atcacctgcc gggccagtca gagtgtcacc aaatatttaa attggtatca gtttaagacc    120
ggccaagccc caagaatcct catctatggg acttatactt tactcagtgg cgtctcgcct    180
cggttcagtg gcgccggatc tggttcactc tacactctga ccatcaccaa tatacagcct    240
gaagacttcg ccacctatta ttgtcaacag gctcacagta ctccctggac cttcggccaa    300
ggaacccacg tggcggccaa c                                              321

<210> SEQ ID NO 43
<211> LENGTH: 384
<212> TYPE: DNA
<213> ORGANISM: Homo sapiens

<400> SEQUENCE: 43
gaagtgcagc tggtggaatc tggccctggc ctggtgcagc cttggggcac actgagcctg     60
acctgtagag tgtccggcga cagcgtgtcc aacgactggt actactgggc ctggatccgg    120
cagacccccg gcagagaact gcaagtgatc ggcaccatct actacagcgg cacaacctac    180 tacaaccccca gcctgcggaa cagagtgacc atcagcctgg acaagagcgt gaacgtggtg    240
tccctgagac tgggctctgt gtctgccgcc gataccgccc agtactactg cgtgcggatg    300
cccagccacg gcttctggtc taccagcttc agctactggt acttcgacct gtggggcaga    360
ggccacttcg tggccgtgtc ttgg                                            384

<210> SEQ ID NO 44
<211> LENGTH: 321
<212> TYPE: DNA
<213> ORGANISM: Homo sapiens

<400> SEQUENCE: 44
gacatccaga tgacccagag cccccagcagc ctgtctgcca gcgtgggcga caaagtgacc    60
atcacctgtc gggccagcca gagcgtgacc aagtacctga actggtatca gtttaagacc    120
ggccaggccc ccagaatcct gatctacggc acctacaccc tgctgagcgg cgtgtcccct    180
agattctctg gcgccggaag cggcagcctg tacaccctga caatcaccaa catccagccc    240
gaggacttcg ccacctacta ctgccagcag gcccacagca cccttggac atttggccag    300 ggaacacacg tggccgccaa c                                              321

<210> SEQ ID NO 45
<211> LENGTH: 383
<212> TYPE: DNA
<213> ORGANISM: Homo sapiens

<400> SEQUENCE: 45
```

```
aagtgcagct ggtggaatct ggccctggcc tggtgcagcc ttggggcaca ctgagcctga      60
cctgtagagt gtccggcgac agcgtgtcca acgacaacta ctactgggcc tggatccggc     120
agacccccgg cagagaactg caagtgatcg gcaccatcta ctacagcggc acaacctact     180
acaaccccag cctgcggaac agagtgacca tcagcctgga caagagcgtg aacgtggtgt     240
ccctgagact gggctctgtg tctgccgccg ataccgccca gtactactgc gtgcggatgc     300
ccagccacgc cttctggtct accagcttca gctactggta cttcgacctg tggggcagag     360
gccacttcgt ggccgtgtct tgg                                             383

<210> SEQ ID NO 46
<211> LENGTH: 320
<212> TYPE: DNA
<213> ORGANISM: Homo sapiens

<400> SEQUENCE: 46
acatccagat gacccagagc cccagcagcc tgtctgccag cgtgggcgac aaagtgacca      60
tcacctgtcg ggccagccag agcgtgacca agtacctgaa ctggtatcag tttaagaccg     120
gccaggcccc cagaatcctg atctacggca cctacaccct gctgagcggc gtgtccccta     180
gattctctgg cgccggatgg ggcagcctgt acaccctgac aatcaccaac atccagcccg     240
aggacttcgc cacctactac tgccagcagg cccacagcac cccttggaca tttggccagg     300
gaacacacgt ggccgccaac                                                 320

<210> SEQ ID NO 47
<211> LENGTH: 384
<212> TYPE: DNA
<213> ORGANISM: Homo sapiens

<400> SEQUENCE: 47
gaggtgcagc tggtggaatc tggacctgga ctggtgcagc cttggggcac tctgtctctg      60
acatgccggg tgagcgggga cagcgtctcc aactttaatt actattgggc ttggatcagg     120
cagacaccag ggcgcgagct gcaggtcatc gggactatct actattccgg aaccacatac     180
tataacccct ctctgcggaa tagagtgacc atttctctgg acaagagtgt caacgtggtc     240
agtctgcgac tgggatctgt gagtgccgct gataccgcac agtactattg cgtgcggatg     300
cccctctcac gcttctggtc aacaagcttt cctactggt atttcgatct gtggggacgg     360
ggccatttcg tggccgtctc ctgg                                            384

<210> SEQ ID NO 48
<211> LENGTH: 321
<212> TYPE: DNA
<213> ORGANISM: Homo sapiens

<400> SEQUENCE: 48
gacatccaga tgacccagtc tccgtcctcc ctgtctgcct ctgttggaga caaagtcacc      60
atcacctgcc gggccagtca gagtgtcacc aaatatttaa attggtatca gtttaagacc     120
ggccaagccc caagaatcct catctatggg acttatactt tactcagtgg cgtctcgcct     180
cggttcagtg gcgccggatc tggttcactc tacactctga ccatcaccaa tatacagcct     240
gaagacttcg ccacctatta ttgtcaacag gctcacagta ctccctggac cttcggccaa     300
ggaacccacg tggcggccaa c                                               321

<210> SEQ ID NO 49
```

<211> LENGTH: 384
<212> TYPE: DNA
<213> ORGANISM: Homo sapiens

<400> SEQUENCE: 49

| | | | | | |
|---|---|---|---|---|---|
| gaggtgcagc | tggtggaatc | tggacctgga | ctggtgcagc | cttggggcac | tctgtctctg | 60 |
| acatgccggg | tgagcgggga | cagcgtctcc | aactacaatt | actattgggc | ttggatcagg | 120 |
| cagacaccag | ggcgcgagct | gcaggtcatc | gggactatct | actattccgg | aaccacatac | 180 |
| tataacccct | ctctgcggaa | tagagtgacc | atttctctgg | acaagagtgt | caacgtggtc | 240 |
| agtctgcgac | tgggatctgt | gagtgccgct | gataccgcac | agtactattg | cgtgcggatg | 300 |
| ccctctcacg | gcttctggtc | aacaagcttt | tcctactggt | atttcgatct | gtggggacgg | 360 |
| ggccattttg | tggccgtctc | ctgg | | | | 384 |

<210> SEQ ID NO 50
<211> LENGTH: 321
<212> TYPE: DNA
<213> ORGANISM: Homo sapiens

<400> SEQUENCE: 50

| | | | | | |
|---|---|---|---|---|---|
| gacatccaga | tgacccagtc | tccgtcctcc | ctgtctgcct | ctgttggaga | caaagtcacc | 60 |
| atcacctgcc | gggccagtca | gagtgtcacc | aaatatttaa | attggtatca | gtttaagacc | 120 |
| ggccaagccc | caagaatcct | catctatggg | acttatactt | tactcagtgg | cgtctcgcct | 180 |
| cggttcagtg | gcgccggatc | tggttcactc | tacactctga | ccatcaccaa | tatacagcct | 240 |
| gaagacttcg | ccacctatta | ttgtcaacag | gctcacagta | ctccctggac | cttcggccaa | 300 |
| ggaacccacg | tggcggccaa | c | | | | 321 |

<210> SEQ ID NO 51
<211> LENGTH: 384
<212> TYPE: DNA
<213> ORGANISM: Homo sapiens

<400> SEQUENCE: 51

| | | | | | |
|---|---|---|---|---|---|
| cagctgcagc | tgcaggagag | tggacctgga | ctggtgaagc | cttcagaaac | actgagcctg | 60 |
| acttgcaccg | tgtccggcga | ctctgtcagt | aactggaatt | actattgggc | atggattaga | 120 |
| cagacaccag | gaagagagct | gcaggtcatc | gggacaatct | actatagtgg | aaccacatac | 180 |
| tataacccct | cactgcggaa | tagagtgacc | atttccctgg | acaaatctgt | caacgtggtc | 240 |
| tctctgcgac | tgggctcagt | gagcgccgct | gatactgccc | agtactattg | cgtgcggatg | 300 |
| cccagccacg | gcttctggtc | cacctctttt | agttactggt | atttcgatct | gtggggacgg | 360 |
| ggcacactgg | tgactgtcag | ctcc | | | | 384 |

<210> SEQ ID NO 52
<211> LENGTH: 321
<212> TYPE: DNA
<213> ORGANISM: Homo sapiens

<400> SEQUENCE: 52

| | | | | | |
|---|---|---|---|---|---|
| gacatccaga | tgacccagtc | tccgtcctcc | ctgtctgcct | ctgttggaga | caaagtcacc | 60 |
| atcacctgcc | gggccagtca | gagtgtcacc | aaatatttaa | attggtatca | gtttaagacc | 120 |
| ggccaagccc | caagaatcct | catctatggg | acttatactt | tactcagtgg | cgtctcgcct | 180 |
| cggttcagtg | gcgccggatc | tggttcactc | tacactctga | ccatcaccaa | tatacagcct | 240 |
| gaagacttcg | ccacctatta | ttgtcaacag | gctcacagta | ctccctggac | cttcggccaa | 300 |

```
ggaacccacg tggcggccaa c                                              321

<210> SEQ ID NO 53
<211> LENGTH: 384
<212> TYPE: DNA
<213> ORGANISM: Homo sapiens

<400> SEQUENCE: 53
gaggtgcagc tggtggaatc tggacctgga ctggtgcagc cttggggcac tctgtctctg     60
acatgccggg tgagcgggga cagcgtctcc aactggtggt actattgggc ttggatcagg    120
cagacaccag ggcgcgagct gcaggtcatc gggactatct actattccgg aaccacatac    180
tataacccct ctctgcggaa tagagtgacc atttctctgg acaagagtgt caatgtggtc    240
agtctgcgac tgggatctgt gagtgccgct gataccgcac agtactattg cgtgcggatg    300
ccctctcacg gcttctggtc aacaagcttt tcctactggt atttcgatct gtggggacgg    360
ggccattttg tggccgtctc ctgg                                           384

<210> SEQ ID NO 54
<211> LENGTH: 321
<212> TYPE: DNA
<213> ORGANISM: Homo sapiens

<400> SEQUENCE: 54
gacatccaga tgacccagtc tccgtcctcc ctgtctgcct ctgttggaga caaagtcacc     60
atcacctgcc gggccagtca gagtgtcacc aaatatttaa attggtatca gtttaagacc    120
ggccaagccc caagaatcct catctatggg acttatactt tactcagtgg cgtctcgcct    180
cggttcagtg gcgccggatc tggttcactc tacactctga ccatcaccaa tatacagcct    240
gaagacttcg ccacctatta ttgtcaacag gctcacagta ctccctggac cttcggccaa    300
ggaacccacg tggcggccaa c                                              321

<210> SEQ ID NO 55
<211> LENGTH: 384
<212> TYPE: DNA
<213> ORGANISM: Homo sapiens

<400> SEQUENCE: 55
caggtgcagc tggaggaatc tggacctgga ctggtccagc cttgggggac tctgagcctg     60
acctgccggg tgtcaggcgg gagcatcagc tcctctagtt actattgggc ttggattagg    120
cagacaccag gccgcgagct gcaggtcatc ggcactatct actatagtgg gaccacatac    180
tataacccct cactgcggaa tagagtgacc atctccctgg acaagtctgt caacgtggtc    240
tctctgcgac tgggatcagt gagcgccgct gataccgcac agtactattg cgtgcggatg    300
cccagccacg gcttctggtc cacatctttt agttactggt atttcgacct gtggggggcgg    360 ggacattttg tggccgtcag ttgg                                           384

<210> SEQ ID NO 56
<211> LENGTH: 321
<212> TYPE: DNA
<213> ORGANISM: Homo sapiens

<400> SEQUENCE: 56
gacatccaga tgacccagtc tccgtcctcc ctgtctgcct ctgttggaga caaagtcacc     60
atcacctgcc gggccagtca gagtgtcacc aaatatttaa attggtatca gtttaagacc    120
```

-continued

```
ggccaagccc caagaatcct catctatggg acttatactt tactcagtgg cgtctcgcct     180
cggttcagtg gcgccggatc tggttcactc tacactctga ccatcaccaa tatacagcct     240
gaagacttcg ccacctatta ttgtcaacag gctcacagta ctccctggac cttcggccaa     300
ggaacccacg tggcggccaa c                                                321
```

<210> SEQ ID NO 57
<211> LENGTH: 30
<212> TYPE: DNA
<213> ORGANISM: Homo sapiens

<400> SEQUENCE: 57

```
ggcgacagcg tgtccaactg gaactactac                                      30
```

<210> SEQ ID NO 58
<211> LENGTH: 30
<212> TYPE: DNA
<213> ORGANISM: Homo sapiens

<400> SEQUENCE: 58

```
ggcgacagcg tgtccaacga ctggtactac                                      30
```

<210> SEQ ID NO 59
<211> LENGTH: 30
<212> TYPE: DNA
<213> ORGANISM: Homo sapiens

<400> SEQUENCE: 59

```
ggggacagcg tctccaactt taattactat                                      30
```

<210> SEQ ID NO 60
<211> LENGTH: 30
<212> TYPE: DNA
<213> ORGANISM: Homo sapiens

<400> SEQUENCE: 60

```
ggggacagcg tctccaacta caattactat                                      30
```

<210> SEQ ID NO 61
<211> LENGTH: 30
<212> TYPE: DNA
<213> ORGANISM: Homo sapiens

<400> SEQUENCE: 61

```
ggggacagcg tctccaactt aaattactat                                      30
```

<210> SEQ ID NO 62
<211> LENGTH: 30
<212> TYPE: DNA
<213> ORGANISM: Homo sapiens

<400> SEQUENCE: 62

```
ggggacagcg tctccaacat taattactat                                      30
```

<210> SEQ ID NO 63
<211> LENGTH: 30
<212> TYPE: DNA
<213> ORGANISM: Homo sapiens

<400> SEQUENCE: 63

```
ggggacagcg tctccaactg gtggtactat                                      30
```

<210> SEQ ID NO 64
<211> LENGTH: 27
<212> TYPE: DNA
<213> ORGANISM: Homo sapiens

<400> SEQUENCE: 64
gggagcatca gctcctctag ttactat            27

<210> SEQ ID NO 65
<211> LENGTH: 9
<212> TYPE: PRT
<213> ORGANISM: Homo sapiens

<400> SEQUENCE: 65

Leu Ala Ser Trp Val Lys Tyr Ile Gln
1               5

<210> SEQ ID NO 66
<211> LENGTH: 9
<212> TYPE: PRT
<213> ORGANISM: Homo sapiens

<400> SEQUENCE: 66

Ile Thr Lys Trp Leu Trp Tyr Ile Lys
1               5

<210> SEQ ID NO 67
<211> LENGTH: 9
<212> TYPE: PRT
<213> ORGANISM: Homo sapiens

<400> SEQUENCE: 67

Ile Thr Ser Trp Ile Lys Tyr Ile Gln
1               5

<210> SEQ ID NO 68
<211> LENGTH: 856
<212> TYPE: PRT
<213> ORGANISM: Homo sapiens

<400> SEQUENCE: 68

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

```
Ile Ser Thr Ser Ile Arg Gly Lys Val Gln Lys Glu Tyr Ala Phe Phe
            165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
            245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
            325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
            370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
            405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
            450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
            530                 535                 540

Leu Ser Gly Ile Val Gln Gln Asn Asn Leu Leu Arg Ala Ile Glu
545                 550                 555                 560

Ala Gln Gln His Leu Leu Gln Leu Thr Val Trp Gly Ile Lys Gln Leu
            565                 570                 575
```

```
Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
        660                 665                 670

Phe Asn Ile Thr Asn Trp Leu Trp Tyr Ile Lys Leu Phe Ile Met Ile
    675                 680                 685

Val Gly Gly Leu Val Gly Leu Arg Ile Val Phe Ala Val Leu Ser Ile
690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
            725                 730                 735

Gly Gly Glu Arg Asp Arg Asp Arg Ser Ile Arg Leu Val Asn Gly Ser
        740                 745                 750

Leu Ala Leu Ile Trp Asp Asp Leu Arg Ser Leu Cys Leu Phe Ser Tyr
    755                 760                 765

His Arg Leu Arg Asp Leu Leu Leu Ile Val Thr Arg Ile Val Glu Leu
770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
        820                 825                 830

Val Gln Gly Ala Cys Arg Ala Ile Arg His Ile Pro Arg Arg Ile Arg
    835                 840                 845

Gln Gly Leu Glu Arg Ile Leu Leu
    850                 855

<210> SEQ ID NO 69
<211> LENGTH: 200
<212> TYPE: PRT
<213> ORGANISM: Homo sapiens

<400> SEQUENCE: 69

Ala Val Gly Ile Gly Ala Leu Phe Leu Gly Phe Leu Gly Ala Ala Gly
1               5                   10                  15

Ser Thr Met Gly Ala Ala Ser Met Thr Leu Thr Val Gln Ala Arg Gln
            20                  25                  30

Leu Leu Ser Gly Ile Val Gln Gln Gln Asn Asn Leu Leu Arg Ala Ile
        35                  40                  45

Glu Ala Gln Gln His Leu Leu Gln Leu Thr Val Trp Gly Ile Lys Gln
    50                  55                  60

Leu Gln Ala Arg Ile Leu Ala Val Glu Arg Tyr Leu Lys Asp Gln Gln
65                  70                  75                  80

Leu Leu Gly Ile Trp Gly Cys Ser Gly Lys Leu Ile Cys Thr Thr Ala
                85                  90                  95
```

```
Val Pro Trp Asn Ala Ser Trp Ser Asn Lys Ser Leu Glu Gln Ile Trp
            100                 105                 110

Asn Asn Met Thr Trp Met Glu Trp Asp Arg Glu Ile Asn Asn Tyr Thr
            115                 120                 125

Ser Leu Ile His Ser Leu Ile Glu Glu Ser Gln Asn Gln Gln Glu Lys
            130                 135                 140

Asn Glu Gln Glu Leu Leu Glu Leu Asp Lys Trp Ala Ser Leu Trp Asn
145                 150                 155                 160

Trp Phe Asn Ile Thr Asn Trp Leu Trp Tyr Ile Lys Leu Phe Ile Met
                    165                 170                 175

Ile Val Gly Gly Leu Val Gly Leu Arg Ile Val Phe Ala Val Leu Ser
            180                 185                 190

Ile Val Asn Arg Val Arg Gln Gly
            195                 200

<210> SEQ ID NO 70
<211> LENGTH: 65
<212> TYPE: PRT
<213> ORGANISM: Homo sapiens

<400> SEQUENCE: 70

Ile Tyr Tyr Ser Gly Thr Thr Tyr Tyr Asn Pro Ser Leu Arg Asn Arg
1               5                   10                  15

Val Thr Ile Ser Leu Trp Lys Ser Val Asn Val Val Ser Leu Arg Leu
            20                  25                  30

Gly Ser Val Ser Ala Ala Asp Thr Ala Gln Tyr Tyr Cys Val Arg Met
            35                  40                  45

Pro Ser His Gly Phe Trp Ser Thr Ser Phe Ser Tyr Trp Tyr Phe Asp
        50                  55                  60

Leu
65

<210> SEQ ID NO 71
<211> LENGTH: 65
<212> TYPE: PRT
<213> ORGANISM: Homo sapiens

<400> SEQUENCE: 71

Ile Tyr Tyr Ser Gly Thr Thr Tyr Tyr Asn Pro Ser Leu Arg Asn Arg
1               5                   10                  15

Val Thr Ile Ser Leu Asp Trp Ser Val Asn Val Val Ser Leu Arg Leu
            20                  25                  30

Gly Ser Val Ser Ala Ala Asp Thr Ala Gln Tyr Tyr Cys Val Arg Met
            35                  40                  45

Pro Ser His Gly Phe Trp Ser Thr Ser Phe Ser Tyr Trp Tyr Phe Asp
        50                  55                  60

Leu
65

<210> SEQ ID NO 72
<211> LENGTH: 20
<212> TYPE: PRT
<213> ORGANISM: Homo sapiens

<400> SEQUENCE: 72

Val Arg Met Pro Ser His Gly Ala Trp Ser Thr Ser Phe Ser Tyr Trp
1               5                   10                  15
```

Tyr Phe Asp Leu
        20

<210> SEQ ID NO 73
<211> LENGTH: 20
<212> TYPE: PRT
<213> ORGANISM: Homo sapiens

<400> SEQUENCE: 73

Val Arg Met Pro Ser His Gly Phe Ala Ser Thr Ser Phe Ser Tyr Trp
1               5                   10                  15

Tyr Phe Asp Leu
        20

<210> SEQ ID NO 74
<211> LENGTH: 20
<212> TYPE: PRT
<213> ORGANISM: Homo sapiens

<400> SEQUENCE: 74

Val Arg Met Pro Ser His Gly Phe Trp Trp Thr Ser Phe Ser Tyr Trp
1               5                   10                  15

Tyr Phe Asp Leu
        20

<210> SEQ ID NO 75
<211> LENGTH: 20
<212> TYPE: PRT
<213> ORGANISM: Homo sapiens

<400> SEQUENCE: 75

Val Arg Met Pro Ser His Gly Phe Trp Ser Trp Ser Phe Ser Tyr Trp
1               5                   10                  15

Tyr Phe Asp Leu
        20

<210> SEQ ID NO 76
<211> LENGTH: 20
<212> TYPE: PRT
<213> ORGANISM: Homo sapiens

<400> SEQUENCE: 76

Val Arg Met Pro Ser His Gly Phe Trp Ser Thr Trp Phe Ser Tyr Trp
1               5                   10                  15

Tyr Phe Asp Leu
        20

<210> SEQ ID NO 77
<211> LENGTH: 20
<212> TYPE: PRT
<213> ORGANISM: Homo sapiens

<400> SEQUENCE: 77

Val Arg Met Pro Ser His Gly Phe Trp Ser Thr Ser Phe Trp Tyr Trp
1               5                   10                  15

Tyr Phe Asp Leu
        20

<210> SEQ ID NO 78
<211> LENGTH: 20
<212> TYPE: PRT
<213> ORGANISM: Homo sapiens -continued

```
<400> SEQUENCE: 78

Val Arg Met Pro Ser His Gly Phe Trp Ser Thr Ser Phe Ser Trp Trp
1               5                   10                  15

Tyr Phe Asp Leu
            20

<210> SEQ ID NO 79
<211> LENGTH: 6
<212> TYPE: PRT
<213> ORGANISM: Homo sapiens

<400> SEQUENCE: 79

Gln Ser Val Thr Trp Tyr
1               5

<210> SEQ ID NO 80
<211> LENGTH: 6
<212> TYPE: PRT
<213> ORGANISM: Homo sapiens

<400> SEQUENCE: 80

Gln Ser Val Thr Lys Trp
1               5

<210> SEQ ID NO 81
<211> LENGTH: 34
<212> TYPE: PRT
<213> ORGANISM: Homo sapiens

<400> SEQUENCE: 81

Arg Arg Arg Asn Glu Gln Glu Leu Leu Glu Leu Asp Lys Trp Ala Ser
1               5                   10                  15

Leu Trp Asn Trp Phe Asp Ile Thr Asn Trp Leu Trp Tyr Ile Arg Arg
            20                  25                  30

Arg Arg

<210> SEQ ID NO 82
<211> LENGTH: 9
<212> TYPE: PRT
<213> ORGANISM: Homo sapiens

<400> SEQUENCE: 82

Asp Ser Val Ser Asn Asp Asn Tyr Tyr
1               5
```

US 10,730,933 B2

HIV BINDING AGENTS

RELATED APPLICATIONS

This application was filed under 35 U.S.C. § 371 and claims priority to International Application No. PCT/IB2016/057367 filed on Dec. 5, 2016, and claims priority to U.S. Ser. No. 62/263,618 filed on Dec. 5, 2015; each of which being hereby incorporated by reference into this disclosure in their entirety.

FIELD OF THE DISCLOSURE

This disclosure relates to binding agents with specificity for human immunodeficiency virus (HIV), methods for making the same, and to methods for using the same to treat and/or prevent HIV infection.

BACKGROUND OF THE DISCLOSURE

As we enter the fourth decade of the HIV epidemic, significant advances have been made in the understanding of HIV pathogenesis and in the development of potent and safe antiviral drugs. More than 30 antiviral drugs have been registered and the impact of combination antiretroviral therapy (ART) on both morbidity and mortality has been remarkable. However, despite the long-term suppression of HIV replication achieved in patients with optimal adherence to ART, HIV invariably rebounds after interruption of therapy. Furthermore, successful therapy does not induce or allow restoration/development of virus-specific immune responses capable of controlling HIV replication in the absence of ART. Thus, life-long ART is needed to control HIV replication and associated disease in the large majority of HIV infected subjects.

A number of immunological interventions have been investigated in the past and currently being further developed with the goal to achieve HIV functional cure, wherein viral replication is suppressed without sustained antiviral therapy. Therapeutic vaccine strategies have been the primary intervention strategy investigated but the results have shown modest efficacy in experimental animal models and patients with the exception of a CMV-based vector HIV vaccine (50% efficacy in the NHP model). Recent studies have generated interesting results on the possibility of using anti-envelope broad neutralizing antibodies (bNabs) as therapeutic agents in HIV infection.

There is a need in the art for additional reagents for targeting HIV, especially neutralizing antibodies, and methods for using the same. This disclosure addresses those needs by providing reagents and methods that may be used to target HIV and cells and/or tissues infected by and/or harboring the same.

BRIEF DESCRIPTION OF THE DRAWINGS

In the following a brief description of the appended figures will be given. The figures are intended to illustrate the present invention in more detail. However, they are not intended to limit the subject matter of the invention in any way.

FIGS. 1A-D show the results of neutralization of a panel of nine (9) HIV-1 pseudoviruses from the Global Panel of HIV-1 reference strains by 70 plasma samples from chronically infected patients naïve to antiretroviral therapy. MLV pseudovirus is used as a negative control. Boxed are the seven donors selected for the collection of lymph nodes to isolate potent broadly neutralizing antibodies. Highlighted with the arrow is donor SA003 who was selected for the isolation of the broadly neutralizing antibody described in the present invention. ID50 values indicate the dilution of plasma capable of neutralizing 50% of viral infection.

FIG. 7 shows the results of neutralization of a panel of seven (7) HIV-2/HIV-1 chimeric pseudoviruses where the HIV-2 (strain 7312A) MPER region is mutagenized by introducing corresponding residues from the MPER consensus sequence of clade B or clade C (in the case of the variant 7312A.C1C) HIV-1 strains.

FIGS. 8A-D show the binding of LN01 or 7B2 monoclonal antibodies to an array of 1423 15-mer peptides, overlapping by 12 amino acids, that cover the full length of the consensus HIV-1 Env gp160 sequences for clades A, B, C, D, group M, CRF01_AE and CRF02_AG. Signals below 2.0E+4 are scored as negative. As expected 7B2 reacts with the gp41 immunodominant region (gp41 ID).

FIGS. 9A-D show the binding, as assessed by surface plasmon resonance, of LN01, PGT145, PGT151 and 17B monoclonal antibodies to the cleaved and soluble HIV-1 Env trimer BG505 SOSIP.664 gp140 that expresses multiple epitopes for broadly neutralizing in the presence or absence of soluble CD4 (sCD4). As expected PGT145 (V1-V2 glycan specific) and PGT151 (binding to a site at the interface between gp120 and gp41) bound with high affinity to BG505 SOSIP.664 gp140 in the absence and presence of sCD4, while 17b (binding to a CD4 binding induced site) bound only in the presence of sCD4.

FIG. 12 shows the binding of mAb 10E8 to the gp41 peptide RRR-NEQELLELDKWASLWNWFDITNWL-WYIRRRR (SEQ ID NO. 89).

Figure 13A:
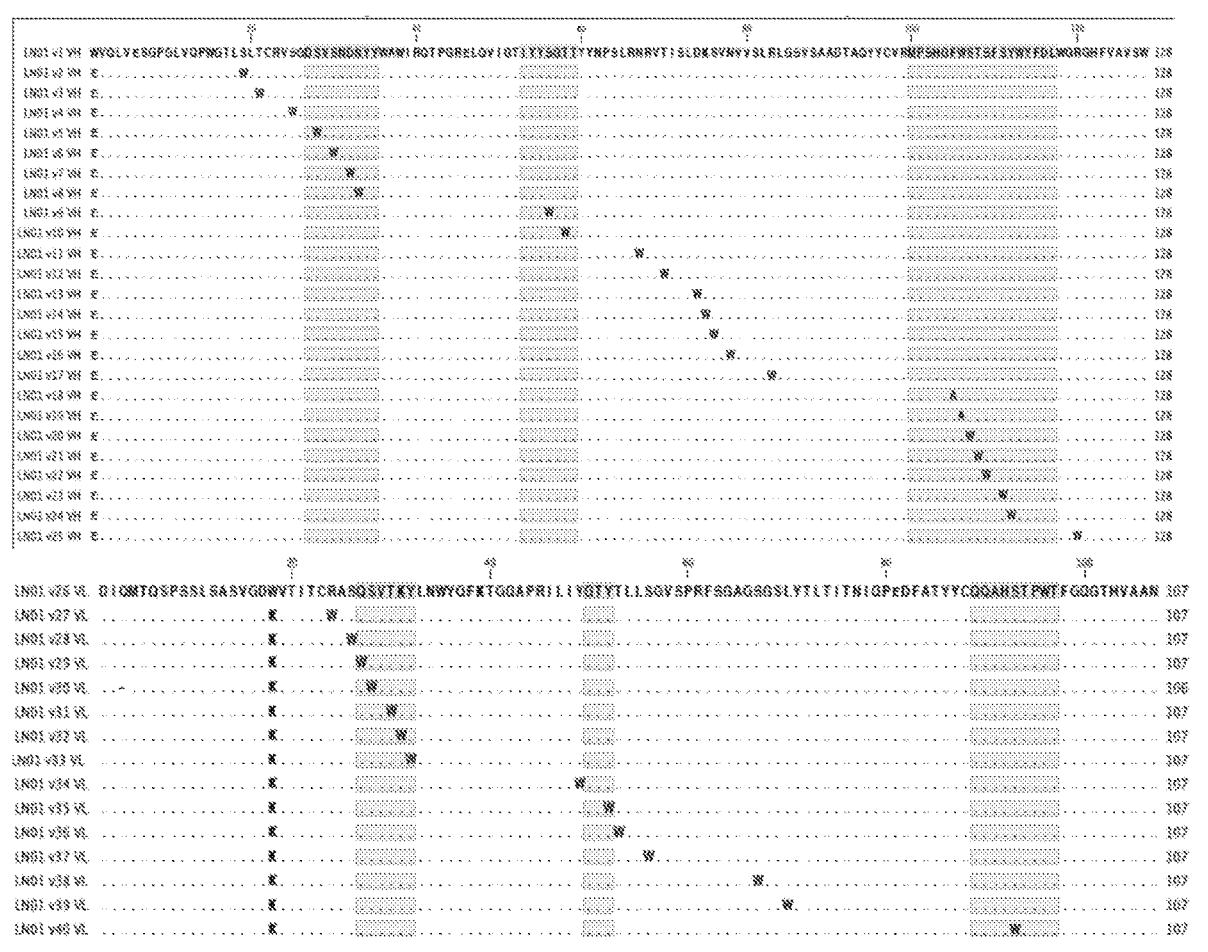

FIGS. 13A-C show the potency of LN01 antibody point mutation variants. A. LN01 VH and VL variants. B. $IC_{50}$ (μg/ml) of LN01 variants. C. $IC_{50}$ ratio ($IC_{50}$ LN01 wt/$IC_{50}$ LN01 variants ("var.")).

FIG. 14A-K show testing of LN01 variants 7, 8 and 38 in parallel with the parental LN01 antibody against a multiclade panel of eight viruses. A-I. Percent (%) neutralization. J. $IC_{50}$ (μg/ml). K. $IC_{50}$ ratio ($IC_{50}$ LN01 wt/$IC_{50}$ LN01 variants ("var.")).

FIGS. 15A-B show testing of LN01 variants 41, 42, 43, 44, 48 and 50 against a multiclade panel of seven viruses. A. $IC_{50}$ (μg/ml). B. $IC_{50}$ ratio ($IC_{50}$ LN01 wt/$IC_{50}$ LN01 variants ("var.")).

FIGS. 18A-B show testing of LN01 variant 49 against a panel of seven viruses. A. $IC_{50}$ (μg/ml). B. $IC_{50}$ ratio ($IC_{50}$ LN01 wt/$IC_{50}$ LN01 variants ("var.")).

SUMMARY OF THE DISCLOSURE

Figure 2:
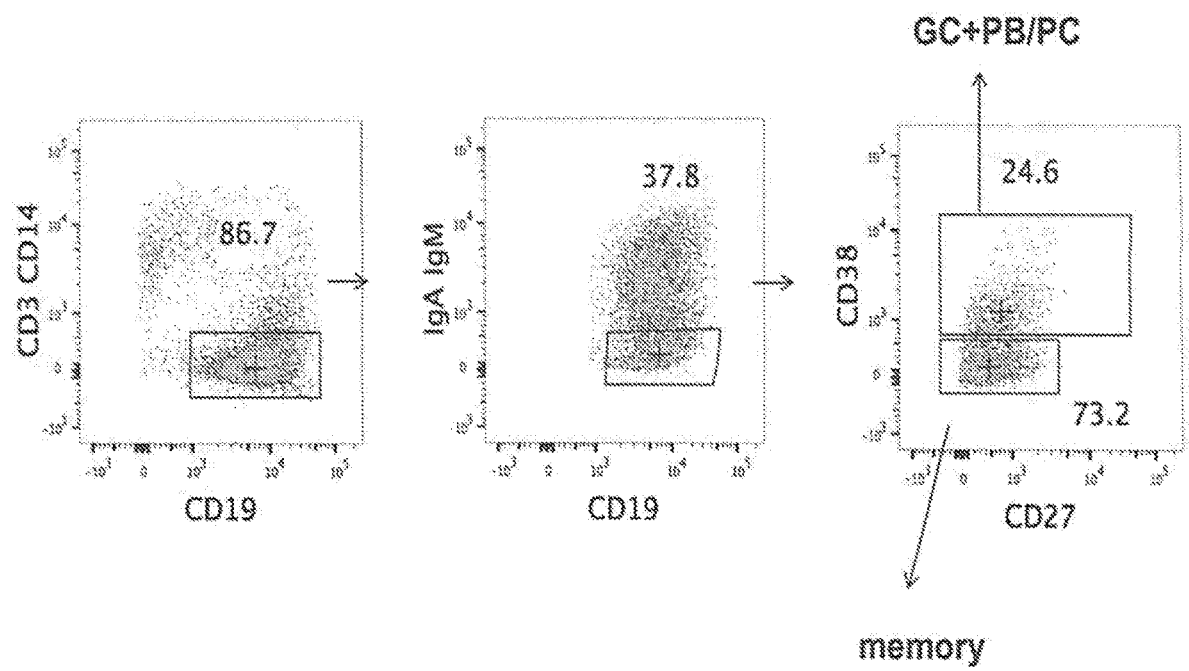
FIG. 2 shows the gating and sorting strategy used to purify memory and germinal center IgG B cells from lymph node samples. B cells were selected for the expression of the surface marker CD19 and IgG B cells were negatively selected for the lack of IgA and IgM B cell receptor (BCR) expression. Germinal center B cells were further selected for the expression of the CD38 marker (that is absent on memory B cells).

This disclosure relates to binding agents with specificity for human immunodeficiency virus (HIV), methods for producing such binding agents, as well as methods for using such binding agents to treat, prevent and/or ameliorate HIV infection.

DETAILED DESCRIPTION

This disclosure relates to binding agents having binding affinity for human immunodeficiency virus (HIV). In some embodiments, the binding agent can bind HIV antigens on viral particles per se or on the surface of cells in vitro and/or in vivo. The binding agents may also bind isolated HIV antigens and/or fragments and/or derivatives thereof, typically in vitro. Also provided are methods for using such binding agents to diagnose, treat, prevent and/or ameliorate one or more diseases associated with HIV. For instance, the binding agents may be antibodies (e.g., monoclonal antibodies) that may react with and/or bind to the epitopes of HIV or polypeptides thereof. The binding agents may be useful for treating disease caused by HIV, such as Acquired Immune Deficiency Syndrome (AIDS). In some embodiments, the binding agents described herein may selectively target and/or eliminate HIV and/or HIV-infected cells containing HIV (e.g., replication competent HIV) and/or expressing proteins thereof. In some embodiments, such cells may be reservoirs for replication competent HIV. In some embodiments, binding agents having, for instance, different specificities (e.g., recognizing different epitopes) may be combined to HIV activity such as infection, replication and/or spread to other cells. In some embodiments, the binding agents described herein may also provide for the selective elimination and/or suppression of HIV or HIV-expressing cells. In some embodiments, the binding agents described herein may be used to suppress and/or eliminate HIV and/or HIV-expressing cells to treat, for instance, HIV infection and/or AIDS. Other embodiments, uses and the like are described below.

The binding agents may be antibodies such as monoclonal antibodies. As shown in the examples herein, the techniques discussed below have been used to identify a fully human mAb termed "LN01", having particular characteristics that are described herein and shown in the examples. The LN01 antibody was isolated and the amino acid sequences of variable heavy ($V_H$) and light ($V_L$) chain domains of said antibody determined. A binding agent such as LN01 may identified by referencing the amino acid and/or nucleic acid sequences corresponding to the variability and/or complementarity determining regions ("CDRs") thereof. A CDR comprises amino acid residues within the variable region identified in accordance with the definitions of the Kabat, Chothia, the accumulation of both Kabat and Chothia, AbM, contact, and/or conformational definitions or any method of CDR determination well known in the art. antibody modeling software (now Accelrys®), or the "contact definition" of CDRs based on observed antigen contacts described by MacCallum et al., 1996, J. Mol. Biol., 262:732-745. In the "conformational definition" of CDRs, the positions of the CDRs may be identified as the residues that make enthalpic contributions to antigen binding (Makabe et al., 2008, Journal of Biological Chemistry, 283:1156-1166). Still other CDR boundary definitions may not strictly follow one of the above approaches, but may nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The amino acid sequences of the heavy chain CDRs (CDRH1, CDRH2, CDRH3), light chain CDRs (CDRL1, CDRL2 (and CDRL2 long), CDRL3), $V_H$ and $V_L$ domains of LN01 and certain exemplary variants thereof are shown in Table 1 below.

TABLE 1

| LN01 region | SEQ ID NO. | Amino Acid Sequence (one letter code) |
|---|---|---|
| LN01 CDRH1 | 1 | GDSVSNDNYY |
| LN01 CDRH2 | 2 | IYYSGTT |
| LN01 CDRH3 | 3 | VRMPSHGFWSTSFSYWYFDL |
| LN01 CDRL1 | 4 | QSVTKY |
| LN01 CDRL2 | — | GTY |

TABLE 1-continued

| LN01 region | SEQ ID NO. | Amino Acid Sequence (one letter code) |
|---|---|---|
| LN01 CDRL2 (long) | 5 | LIYGTYTLL |
| LN01 CDRL3 | 6 | QQAHSTPWT |
| LN01 Variable Heavy (V$_H$) (CDRH1, CDRH2 and CDRH3 underlined) | 7 | EVQLVESGPGLVQPWGTLSLTCRVSGDSVSNDN YYWAWIRQTPGRELQVIGTIYYSGTTYYNPSLRN RVTISLDKSVNVVSLRLGSVSAADTAQYYCVRMP SHGFWSTSFSYWYFDLWGRGHFVAVSW |
| LN01 Variable Light (V$_L$) (CDRL1, CDRL2 and CDRL3 underlined) | 8 | DIQMTQSPSSLSASVGDKVTITCRASQSVTKYLN WYQFKTGQAPRILIYGTYTLLSGVSPRFSGAGSG SLYTLTITNIQPEDFATYYCQQAHSTPWTFGQGT HVAAN |
| LN01 variant 7 Variable Heavy (V$_H$) (CDRH1, CDRH2 and CDRH3 underlined) | 9 | EVQLVESGPGLVQPWGTLSLTCRVSGDSVSNW NYYWAWIRQTPGRELQVIGTIYYSGTTYYNPSLR NRVTISLDKSVNVVSLRLGSVSAADTAQYYCVRM PSHGFWSTSFSYWYFDLWGRGHFVAVSW |
| LN01 variant 7 Variable Light (V$_L$) (CDRL1, CDRL2 and CDRL3 underlined) | 10 | DIQMTQSPSSLSASVGDKVTITCRASQSVTKYLN WYQFKTGQAPRILIYGTYTLLSGVSPRFSGAGSG SLYTLTITNIQPEDFATYYCQQAHSTPWTFGQGT HVAAN |
| LN01 variant 8 Variable Heavy (V$_H$) (CDRH1, CDRH2 and CDRH3 underlined) | 11 | EVQLVESGPGLVQPWGTLSLTCRVSGDSVSND WYYWAWIRQTPGRELQVIGTIYYSGTTYYNPSLR NRVTISLDKSVNVVSLRLGSVSAADTAQYYCVRM PSHGFWSTSFSYWYFDLWGRGHFVAVSW |
| LN01 variant 8 Variable Light (V$_L$) (CDRL1, CDRL2 and CDRL3 underlined) | 12 | DIQMTQSPSSLSASVGDKVTITCRASQSVTKYLN WYQFKTGQAPRILIYGTYTLLSGVSPRFSGAGSG SLYTLTITNIQPEDFATYYCQQAHSTPWTFGQGT HVAAN |
| LN01 variant 38 Variable Heavy (V$_H$) (CDRH1, CDRH2 and CDRH3 underlined) | 13 | EVQLVESGPGLVQPWGTLSLTCRVSGDSVSNDN YYWAWIRQTPGRELQVIGTIYYSGTTYYNPSLRN RVTISLDKSVNVVSLRLGSVSAADTAQYYCVRMP SHGFWSTSFSYWYFDLWGRGHFVAVSW |
| LN01 variant 38 Variable Light (V$_L$) (CDRL1, CDRL2 and CDRL3 underlined) | 14 | DIQMTQSPSSLSASVGDKVTITCRASQSVTKYLN WYQFKTGQAPRILIYGTYTLLSGVSPRFSGAGWG SLYTLTITNIQPEDFATYYCQQAHSTPWTFGQGT HVAAN |
| LN01 variant 41 Variable Heavy (V$_H$) (CDRH1, CDRH2 and CDRH3 underlined) | 15 | EVQLVESGPGLVQPWGTLSLTCRVSGDSVSNFN YYWAWIRQTPGRELQVIGTIYYSGTTYYNPSLRN RVTISLDKSVNVVSLRLGSVSAADTAQYYCVRMP SHGFWSTSFSYWYFDLWGRGHFVAVSW |
| LN01 variant 41 Variable Light (V$_L$) (CDRL1, CDRL2 and CDRL3 underlined) | 16 | DIQMTQSPSSLSASVGDKVTITCRASQSVTKYLN WYQFKTGQAPRILIYGTYTLLSGVSPRFSGAGSG SLYTLTITNIQPEDFATYYCQQAHSTPWTFGQGT HVAAN |
| LN01 variant 42 Variable Heavy (V$_H$) (CDRH1, CDRH2 and CDRH3 underlined) | 17 | EVQLVESGPGLVQPWGTLSLTCRVSGDSVSNYN YYWAWIRQTPGRELQVIGTIYYSGTTYYNPSLRN RVTISLDKSVNVVSLRLGSVSAADTAQYYCVRMP SHGFWSTSFSYWYFDLWGRGHFVAVSW |
| LN01 variant 42 Variable Light (V$_L$) (CDRL1, CDRL2 and CDRL3 underlined) | 18 | DIQMTQSPSSLSASVGDKVTITCRASQSVTKYLN WYQFKTGQAPRILIYGTYTLLSGVSPRFSGAGSG SLYTLTITNIQPEDFATYYCQQAHSTPWTFGQGT HVAAN |
| LN01 variant 48 Variable Heavy (V$_H$) (CDRH1, CDRH2 and CDRH3 underlined) | 19 | QLQLQESGPGLVKPSETLSLTCTVSGDSVSNWN YYWAWIRQTPGRELQVIGTIYYSGTTYYNPSLRN RVTISLDKSVNVVSLRLGSVSAADTAQYYCVRMP SHGFWSTSFSYWYFDLWGRGTLVTVSS |
| LN01 variant 48 Variable Light (V$_L$) | 20 | DIQMTQSPSSLSASVGDKVTITCRASQSVTKYLN WYQFKTGQAPRILIYGTYTLLSGVSPRFSGAGSG |

TABLE 1-continued

| LN01 region | SEQ ID NO. | Amino Acid Sequence (one letter code) |
|---|---|---|
| (CDRL1, CDRL2 and CDRL3 underlined) | | SLYTLTITNIQPEDFATYYC<u>QQAHSTPWT</u>FGQGT HVAAN |
| LN01 variant 49 Variable Heavy (V<sub>H</sub>) (CDRH1, CDRH2 and CDRH3 underlined) | 21 | EVQLVESGPGLVQPWGTLSLTCRVS<u>GDSVSNW WY</u>YWAWIRQTPGRELQVIGT<u>IYYSGTTYY</u>NPSLR NRVTISLDKSVNVVSLRLGSVSAADTAQYYC<u>VRM PSHGFWSTSFSYWYFDL</u>WGRGHFVAVSW |
| LN01 variant 49 Variable Light (V<sub>L</sub>) (CDRL1, CDRL2 and CDRL3 underlined) | 22 | DIQMTQSPSSLSASVGDKVTITCRAS<u>QSVTKYLN</u> WYQFKTGQAPRI<u>LIYGTYTLL</u>SGVSPRFSGAGSG SLYTLTITNIQPEDFATYYC<u>QQAHSTPWT</u>FGQGT HVAAN |
| LN01 variant 82 Variable Heavy (V<sub>H</sub>) (CDRH1, CDRH2 and CDRH3 underlined) | 23 | QVQLEESGPGLVQPWGTLSLTCRVSG<u>GSISSSS YY</u>YWAWIRQTPGRELQVIGT<u>IYYSGTTYY</u>NPSLRN RVTISLDKSVNVVSLRLGSVSAADTAQYYC<u>VRMP SHGFWSTSFSYWYFDL</u>WGRGHFVAVSW |
| LN01 variant 82 Variable Light (V<sub>L</sub>) (CDRL1, CDRL2 and CDRL3 underlined) | 24 | DIQMTQSPSSLSASVGDKVTITCRAS<u>QSVTKYLN</u> WYQFKTGQAPRI<u>LIYGTYTLL</u>SGVSPRFSGAGSG SLYTLTITNIQPEDFATYYC<u>QQAHSTPWT</u>FGQGT HVAAN |
| LN01 variants 7 and 48 Variable Heavy (V<sub>H</sub>) CDRH1 | 25 | GDSVSNWNYY |
| LN01 variant 8 Variable Heavy (V<sub>H</sub>) CDRH1 | 26 | GDSVSNDWYY |
| LN01 variant 41 Variable Heavy (V<sub>H</sub>) CDRH1 | 27 | GDSVSNFNYY |
| LN01 variant 42 Variable Heavy (V<sub>H</sub>) CDRH1 | 28 | GDSVSNYNYY |
| LN01 variant 43 Variable Heavy (V<sub>H</sub>) CDRH1 | 29 | GDSVSNLNYY |
| LN01 variant 44 Variable Heavy (V<sub>H</sub>) CDRH1 | 30 | GDSVSNINYY |
| LN01 variant 49 Variable Heavy (V<sub>H</sub>) CDRH1 | 31 | GDSVSNWWYY |
| LN01 variant 82 Variable Heavy (V<sub>H</sub>) CDRH1 | 32 | GSISSSSYY |

A binding agent of this disclosure may comprise, for example, any one or more of the amino acid sequences shown in Table 1 (i.e., any one or more of SEQ ID NOS. 1-32 or GTY (LN01 CDRL2)). Fragments and/or derivatives (e.g., comprising substituted amino acids, such as conservative substitutions) thereof are also disclosed. An exemplary derivative of the LN01 antibody (an IgG3 antibody), for instance, is termed "IgG1 LN01" in which the LN01 variable regions were cloned into an IgG1 backbone. In some embodiments, then, a binding agent of this disclosure may comprise one or more (i.e., one, two, three, four, five, six or seven) of SEQ ID NOS. 1-32. In some embodiments, it is preferred that the binding agent comprise each of SEQ ID NOS. 1-6 and or GTY (LN01 CDRL2). In some embodiments, such a binding agent may comprise SEQ ID NO. 7 and/or SEQ ID NO. 8; SEQ NOS. 9 and/or 10; SEQ NOS. 11 and/or 12; SEQ NOS. 13 and/or 14; SEQ NOS. 15 and/or 16; SEQ NOS. 17 and/or 18; SEQ NOS. 19 and/or 20; SEQ NOS. 21 and/or 22; or SEQ NOS. 23 and/or 24; or a conservatively substituted variant thereof. In preferred embodiments, the binding agent comprises SEQ ID NO. 7 and SEQ ID NO. 8; SEQ NOS. 9 and 10; SEQ NOS. 11 and 12; SEQ NOS. 13 and 14; SEQ NOS. 15 and 16; SEQ NOS. 17 and 18; SEQ NOS. 19 and 20; SEQ NOS. 21 and 22; or SEQ NOS. 23 and 24; or a conservatively substituted variant thereof. In some embodiments, the binding agent may comprise any of SEQ ID NOS. 1-32 comprising one or more amino acid substitutions, in particular conservative substitutions (see, e.g., Table 2). Exemplary variants of SEQ ID NO.:1 (LN01 CDR H1) include, for instance, any of SEQ ID NOS. 25-32. In some embodiments, the binding agent may be a monoclonal antibody or a fragment or derivative thereof. In some embodiments, the binding agent may be an HIV-binding fragment of such a monoclonal antibody. Such embodiments would typically include at least one or more of SEQ ID NOS. 1-32, and preferably include each of SEQ ID NOS. 1-6 (or GTY (LN01 CDRL2) such as SEQ ID NOS. 7-8; SEQ ID NO. 25 (LN01 variants 7 and 48 CDR H1); SEQ ID NO. 26 (LN01 variant 8 CDR H1); SEQ ID NO. 27 (LN01 variant 41 CDR H1); SEQ ID NO. 28 (LN01 variant 42 CDR H1); SEQ ID NO. 29 (LN01 variant 43 CDR H1); SEQ ID NO. 30 (LN01 variant 44 CDR H1); SEQ ID NO. 31 (LN01 variant 49, a combination of LN01 variant 7 CDR H1 and LN01 variant 8 CDR H1); or SEQ ID NO. 32 (LN01 variant 82 CDR H1). In some embodiments, it may be beneficial to avoid variants comprising a variable heavy chain region comprising SEQ ID NO. 70 or 71 (LN01 variants 13 and 14, respectively); tryptophan (W) at an amino acid corresponding to amino acid 22 of SEQ ID NO. 70 (LN01 variant 13); tryptophan (W) at an amino acid corresponding to amino acid 23 of SEQ ID NO. 71 (LN01 variant 14); a CDRH3 amino acid sequence of any of SEQ ID NOS. 72-78 (LN01 variants 18-24, respectively); alanine (A) at an amino acid corresponding to amino acid 8 of SEQ ID NO. 72 (LN01 variant 18); alanine (A) at an amino acid corresponding to amino acid 9 of SEQ ID NO. 73 (LN01 variant 19); tryptophan (W) at an amino acid corresponding to amino acid 10 of SEQ ID NO. 74 (LN01 variant 20); tryptophan (W) at an amino acid corresponding to amino acid 11 of SEQ ID NO. 75 (LN01 variant 21); tryptophan (W) at an amino acid corresponding to amino acid 12 of SEQ ID NO. 76 (LN01 variant 22); tryptophan (W) at an amino acid corresponding to amino acid 14 of SEQ ID NO. 77 (LN01 variant 23); tryptophan (W) at an amino acid corresponding to amino acid 15 of SEQ ID NO. 78 (LN01 variant 24); a variable light chain region comprising SEQ ID NO. 79 or 80 (LN01 variants 32 and 33, respectively); tryptophan (W) at an amino acid corresponding to amino acid 5 of SEQ ID NO. 79 (LN01 variant 32); and/or, tryptophan (W) at an amino acid corresponding to amino acid 6 of SEQ ID NO. 80 (LN01 variant 33), as these may not provide suitable HIV neutralizing activity. Thus, in some embodiments, the binding agent may comprise any of SEQ ID NOS. 1-32 but not those of any one or more of SEQ ID NOS. 70-80. Other suitable embodiments may be derived by those of ordinary skill in the art from this disclosure.

It is preferred that the binding agent (e.g., antibody, or the antigen binding fragment thereof), comprises one or more amino acid sequences having at least 70%, at least 75%, at least 80%, at least 85%, at least 88%, at least 90%, at least 92%, at least 95%, at least 96%, at least 97%, at least 98% or at least 99% identity to at least one of SEQ ID NOS. 1-32 (i.e., the CDR sequences, the VH sequence and/or the VL sequence shown in Table 1). In some embodiments, that percent identity is with respect to an amino acid sequence of at least three amino acids (e.g., as in GTY of LN01 CDRL2), six amino acids (e.g., as in LN01 CDRL1 (SEQ ID NO.:4)), seven amino acids (e.g., as in LN01 CDRH2 (SEQ ID NO.:2)), nine amino acids (e.g., as in LN01 CDRL2 (long), (SEQ ID NO.:5), LN01 CDRL3 (SEQ ID NO.:6), LN01 variant 82 CDRH1 (SEQ ID NO. 32)), ten amino acids (e.g., as in LN01 CDRH1 (SEQ ID NO.:1) or any of SEQ ID NOS. 25-31), or twenty amino acids (e.g., as in LN01 CDRH3 (SEQ ID NO.:3). As discussed below, identities of less than 100% may result from the natural or synthetic substitution of one or more amino acids with another amino acid(s), as in a conservative substitution (see, e.g., Table 2). Various combinations of SEQ ID NOS. 1-32 may be useful as may ascertained by one of ordinary skill in the art using the techniques described herein or as may be otherwise available to those of ordinary skill in the art. In preferred embodiments, the binding agent binds HIV and/or cells infected by HIV and/or expressing HIV proteins. In some especially preferred embodiments, the binding agent neutralizes HIV as described herein. In preferred embodiments, the binding agent both binds HIV and/or cells infected by HIV and/or expressing HIV proteins, and neutralizes HIV.

The variable region and/or CDR sequences (e.g., of Table 1) may be used in combination with one or more other variable region/CDR amino acid sequences available to those of ordinary skill in the art. Such variable region/CDR amino acid sequences may alternatively and/or also be adjoined to one or more types of constant region polypeptides of an antibody molecule. For instance, the CDR amino acid sequences shown in Table 1 may be adjoined to or associated with the constant regions of any antibody molecule of the same or a different species (e.g., human, goat, rat, sheep, chicken) and/or antibody subtype of that from which the CDR amino acid sequence was derived. For instance, an exemplary binding agent may be, or may be derived from, one having about the same neutralizing activity and/or binding the same or similar epitopes and/or exhibiting about the same affinity as another binding agent comprising one or more of the amino acid sequences shown in Table 1 (e.g., LN01 and IgG1 LN01). The binding agent may comprise an antibody heavy and/or a light chain that each comprises one or more constant and/or variable regions. Any of the amino acid sequences described herein (e.g, as in Table 1), and/or any fragments and/or derivatives thereof, may also be combined with any other variable region and/or CDR in any order and/or combination to form new binding agents, e.g., hybrid and/or fusion binding agents, and/or inserted into other heavy and/or light chain variable regions using standard techniques.

This disclosure also provides for the use of such binding agents to isolate, identify, and/or target HIV and/or cells harboring and/or infected by HIV and/or expressing HIV antigens. In certain embodiments, such binding agents may be reactive against HIV antigens such as proteins expressed on the surface of cells. In some embodiments, the binding agent(s) is an antibody (antibodies). The term "antibody" or "antibodies" may refer to whole or fragmented antibodies in unpurified or partially purified form (e.g., hybridoma supernatant, ascites, polyclonal antisera) or in purified form. The antibodies may be of any suitable origin or form including, for example, murine (e.g., produced by murine hybridoma cells), or expressed as humanized antibodies, chimeric antibodies, human antibodies, and the like.

For instance, antibodies may be wholly or partially derived from human (e.g., IgG (IgG1, IgG2, IgG2a, Ig2b, IgG3, IgG4), IgM, IgA (IgA1 and IgA2), IgD, and IgE), canine (e.g., IgGA, IgGB, IgGC, IgGD), chicken (e.g., IgA, IgD, IgE, IgG, IgM, IgY), goat (e.g., IgG), mouse (e.g., IgG, IgD, IgE, IgG, IgM), pig (e.g., IgG, IgD, IgE, IgG, IgM), and/or rat (e.g., IgG, IgD, IgE, IgG, IgM) antibodies, for instance. Methods of preparing, utilizing and storing various types of antibodies are well-known to those of skill in the art and would be suitable in practicing the present invention (see, for example, Harlow, et al. *Antibodies: A Laboratory Manual*, Cold Spring Harbor Laboratory, 1988; Harlow, et al. *Using Antibodies: A Laboratory Manual, Portable Protocol No.* 1, 1998; Kohler and Milstein, Nature, 256:495 (1975)); Jones et al. Nature, 321:522-525 (1986); Riechmann et al. Nature, 332:323-329 (1988); Presta (Curr. Op.

Struct. Biol., 2:593-596 (1992); Verhoeyen et al. (Science, 239:1534-1536 (1988); Hoogenboom et al., J. Mol. Biol., 227:381 (1991); Marks et al., J. Mol. Biol., 222:581 (1991); Cole et al., Monoclonal Antibodies and Cancer Therapy, Alan R. Liss, p. 77 (1985); Boemer et al., J. Immunol., 147(1):86-95 (1991); Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995); as well as U.S. Pat. Nos. 4,816,567; 5,545,807; 5,545,806; 5,569,825; 5,625,126; 5,633,425; and, 5,661,016). In certain applications, the antibodies may be contained within hybridoma supernatant or ascites and utilized either directly as such or following concentration using standard techniques. In other applications, the antibodies may be further purified using, for example, salt fractionation and ion exchange chromatography, or affinity chromatography using Protein A, Protein G, Protein A/G, and/or Protein L ligands covalently coupled to a solid support such as agarose beads, or combinations of these techniques. The antibodies may be stored in any suitable format, including as a frozen preparation (e.g., −20° C. or −70° C.), in lyophilized form, or under normal refrigeration conditions (e.g., 4° C.). When stored in liquid form, for instance, it is preferred that a suitable buffer such as Tris-buffered saline (TBS) or phosphate buffered saline (PBS) is utilized. In some embodiments, the binding agent may be prepared as an injectable preparation, such as in suspension in a non-toxic parenterally acceptable diluent or solvent. Suitable vehicles and solvents that may be utilized include water, Ringer's solution, and isotonic sodium chloride solution, TBS and/or PBS, among others. Such preparations may be suitable for use in vitro or in vivo may be prepared as is known in the art and the exact preparation may depend on the particular application.

The binding agents described herein are not, however, in any way limited to antibodies (i.e., whole antibodies). For example, the binding agent may be any compound exhibiting similar binding properties as another (e.g., a mimetic). For example, an exemplary binding agent may be one that binds HIV and/or can compete with another binding agent having specificity therefor (e.g., a monoclonal antibody such as LN01). In some embodiments, the mimetic may exhibit substantially the same affinity in binding assays as the binding agent (e.g., monoclonal antibody) to which it is being compared. The affinity a particular binding agent may be measured by any suitable assay including but not limited to FACS staining of cell surface HIV antigens (e.g., polypeptides). One binding agent may be said to have "substantially the same affinity" as another where the measurements (e.g., nm) are within about any of 1-20, 1-5, 5-10, 10-15, or 15-20 percent of one another. Exemplary mimetics may include, for example, organic compounds that specifically bind HIV, or an affibody (Nygren, et al. FEBS J. 275 (11): 2668-76 (2008)), affilin (Ebersbach, et al. J. Mol. Biol. 372 (1): 172-85 (2007)), affitin (Krehenbrink, et al. J. Mol. Biol. 383 (5): 1058-68 (2008)), anticalin (Skerra, A. FEBS J. 275 (11): 2677-83 (2008)), avimer (Silverman, et al. Nat. Biotechnol. 23 (12): 1556-61 (2005)), DARPin (Stumpp, et al. Drug Discov. Today 13 (15-16): 695-701 (2008)), Fynomer (Grabulovski, et al. J. Biol. Chem. 282 (5): 3196-3204 (2007)), Kunitz domain peptide (Nixon, et al. Curr. Opin. Drug Discov. Devel. 9 (2): 261-8 (2006)), and/or a monobody (Koide, et al. Methods Mol. Biol. 352: 95-109 (2007)). Other mimetics may include, for example, a derivative of an antibody such as, for example, an $F_{ab}$, $F_{ab2}$, Fab' single chain antibody, $F_v$, single domain antibody, mono-specific antibody, bi-specific antibody, tri-specific antibody, multi-valent antibody, chimeric antibody, canine-human chimeric antibody, canine-mouse chimeric antibody, antibody comprising a canine Fc, humanized antibody, human antibody, caninized, CDR-grafted antibody (i.e., comprising any of SEQ ID NOS. 1-32 shown in Table 1), shark antibody, nanobody, canelid antibody, microbody, and/or intrabody, or derivative thereof. Other binding agents are also provided herein as would be understood by one of ordinary skill in the art.

Any method known to those of ordinary skill in the art may be used to generate binding agents having specificity for (e.g., binding to) HIV. For instance, to generate and isolate monoclonal antibodies an animal such as a mouse may be administered (e.g., immunized) with one or more HIV proteins. Animals exhibiting serum reactivity to HIV expressed on activated human T lymphocytes (as determined by, for instance, flow cytometry and/or microscopy) may then be selected for generation of anti-HIV hybridoma cell lines. This may be repeated for multiple rounds. Screening may also include, for instance, affinity binding and/or functional characterization to identify the binding agent as an being specific for HIV. In some embodiments, such as in the Examples herein, human beings may be screened for the expression of antibodies against HIV. In some embodiments, plasma samples of human beings infected by HIV may be screened to identify persons expressing anti-HIV antibodies, and in particular, neutralizing antibodies. Neutralizing antibody-producing cells of such persons may then be isolated, followed by the isolation and characterization of the antibodies produced thereby (e.g., as in the examples herein). A neutralizing antibody may be one that exhibits the ability to neutralize, or inhibit, infection of cells by HIV. In general, a neutralization assay typically measures the loss of infectivity of the virus through reaction of the virus with specific antibodies. Typically, a loss of infectivity is caused by interference by the bound antibody with any of the virus replication steps including but not limited to binding to target cells, entry, and/or viral release. The presence of unneutralized virus is detected after a predetermined amount of time, e.g., one, two, three, four, five, six, seven, eight, nine, 10, 12 or 14 days, by measuring the infection of target cells using any of the systems available to those of ordinary skill in the art (e.g., a luciferase-based system). A non-limiting example of a neutralization assay may include combining a given amount of a virus or pseudovirus (see below) and different concentrations of the test or control (typically positive and negative controls assayed separately) antibody or antibodies are mixed under appropriate conditions (e.g., one (1) hour at room temperature) and then inoculated into an appropriate target cell culture (e.g., TZM-bl cells). For instance, binding agent-producing cells (e.g., B cells producing antibodies) may be assayed for the production of HIV-1 neutralizing antibodies by seeding such cells in separate plates as single cell micro-cultures on human feeder cells in the presence of Epstein-Barr Virus (EBV) (which also stimulate polyclonally memory B cells), a cocktail of growth factors (e.g., TLR9 agonist CpG-2006, IL-2 (1000 IU/ml), IL-6 (10 ng/ml), IL-21 (10 ng/ml), and anti-B cell receptor (BCR) goat antibodies (which trigger BCRs). After an appropriate time (e.g., 14 days), supernatants of such cultures may tested in a primary luciferase-based screening system using two or more representative HIV-1 viruses or pseudoviruses that productively infect such cells. The pseudoviruses may be incubated with B cell culture supernatants for an appropriate time and temperature (e.g., one (1) h at 37% (5% $CO_2$)) before the addition of host cells (e.g., 3000 TZM-bl cells). Incubation for an appropriate time (e.g., 72 hours) may then follow, after which the supernatant may be removed and Steadylite reagent (Perkin Elmer) added (e.g., 15 µl). Luciferase activity may then deteremined (e.g., five minutes later) on a Synergy microplate luminometer (BioTek). Decreased luciferase activity relative to a negative control typically indicates virus neutralization. Neutralization assays such as these, suitable for analyzing binding agents of this disclosure, are known in the art (see, e.g., Montefiori, D. C. Curr. Protocol. Immunol. Chapter 12, Unit 12.11 (2005); Edmonds, et al. Virology, 408(1): 1-13 (2010); Seaman, et al. J. Virol. 84(3): 1439-1452 (2010); Pace, et al. PNAS USA, 110(33): 13540-13545 (2013)). In some embodiments, test samples may be screened for the presence of antibodies able to neutralize a panel of HIV pseudoviruses (e.g., nine (9) HIV-1 pseudoviruses from the Global Panel of HIV-1 reference strains as conducted in the examples herein (those pseudoviruses being BJOX (CRF007_BC), CE1176 (C), TRO. 11 (B), X1632 (G), CH119 (CRF07_BC), CNE55 (CRF01_AE), 25710 (C), 246F3 (AC), CE0217 (C)); DeCamp, A. et al. Global panel of HIV-1 Env reference strains for standardized assessments of vaccine-elicited neutralizing antibodies. J Virol 88, 2489-2507 (2014)). Neutralization of a larger panel of psuedoviruses may also be tested; for instance, de Camp et al. describe a group of 12 pseudoviruses (also known as HIV-1 Env Reference Strains): 398F1, 25710, CNE8, TRO11, X2278, BJOX2000, X1632, CE1176, 246F3, CH119, CE0217, and CNE55. In some embodiments, a panel of ten HIV isolates may be tested and a BNA may be identified as one that neutralizes six, seven, eight, nine members of a panel of nine pseudoviruses; or six, seven, eight, nine, 10, 11 or 12 members of a panel of 12 pseudoviruses. Screening of larger panels of such pseudoviruses (e.g., a panel of 118 pseudoviruses as in the examples herein) may also be carried out. An exemplary panel of 118 pseudoviruses used in the examples against which test samples may be tested for neutralizing antibodies may include, for instance, those shown in FIG. 4 (including clade A, clade B, clade C, clade D, clade G, circulating recombinant forms CRF10_CD, CRF01_AE, CRF02_AG and CRF07_BC, as well as non-circulating recombinants AC and ACD strains). In some embodiments, neutralization may be determined as a measure of the concentration (e.g., µg/ml) of monoclonal antibody capable of neutralizing any of about 50%, 60%, 70%, 80%, 90%, 95%, or 99% of viral infection (an "$IC_{50}$" value). In some embodiments, a binding agent may be considered neutralizing if it is able to neutralize 50% of viral infection at a concentration of, for instance, about any of $10^{-5}$, $10^{-4}$, $10^{-3}$, $10^{-2}$, $10^{-1}$, $10^{0}$, $10^{1}$, $10^{2}$, or $10^{3}$ µg/ml (an $IC_{50}$ value as shown in in FIG. 3). In some embodiments, as in the Examples herein, it is preferred that this $IC_{50}$ value be below 25 µg/ml, and even more preferably below about any of 15, 10, 5, 2, 1, 0.5, 0.25, 0.1, 0.05, or 0.01 µg/ml. In preferred embodiments, as for the LN01 antibody described herein, the $IC_{50}$ value may be less than 0.011 (e.g., FIG. 7). In some embodiments, the ability of a neutralizing antibody to neutralize viral infection may also be expressed as a percent neutralization (e.g., 10%, 20%, 30%, 40%, 50%, 60%, 70%, 80%, 90%, 95%, or 99% (e.g., as in FIG. 3)). Other measures of neutralization may also be suitable as may be determined by those of ordinary skill in the art.

In some embodiments, the binding agents described herein may be broadly neutralizing antibodies (BNAs) identified in biological samples (e.g., plasma) obtained from HIV-infected persons. As mentioned above and shown in the examples herein, such BNAs may be identified by testing plasma samples of patients chronically infected by HIV (preferably those naïve to antiretroviral therapy) for the ability to neutralize multi-clade HIV isolates (e.g., initially using a nine or 12-member panel and then a larger panel (e.g., 118 members) of pseudoviruses)). In some embodiments, the samples may be derived from patients known to be "Elite Controllers" with viremia <50 HIV RNA copies per ml of plasma. Screening procedures such as these may result in the identification of patients that may serve as lymph node donors for the subsequent isolation and characterization of B cells producing BNAs. In carrying out such screening assays, neutralizing activity is typically compared to a negative control such as murine leukemia virus (MLV) pseudovirus.

In some embodiments, germinal center and memory IgG B cells of patients expressing neutralizing binding agents (e.g., antibodies) may be isolated and further studied. In some embodiments, the cells may be sorted separately according to IgG (e.g., IgA and IgM negative cells), CD19, and CD38 expression (germinal center B cells are CD38 positive) (see, e.g., FIG. 2) and interrogated for the production of HIV-1 neutralizing antibodies. For instance, highly pure IgG memory B cells and IgG germinal cells may be seeded in separate plates as single cell micro-cultures on human feeder cells in the presence of Epstein-Barr Virus (EBV) (which also stimulate polyclonally memory B cells) and a cocktail of growth factors and the like (e.g., composed TLR9 agonist CpG-2006, IL-2 (1000 IU/ml), IL-6 (10 ng/ml), IL-21 (10 ng/ml), and anti-BCR goat antibodies (B cell receptor (BCR) triggering)). Supematants of such cultures (e.g., from day 14 cultures) may then be tested in a primary screening (e.g., using a 384-well based HIV-1 pseudoviruses neutralization assay using in parallel two strains, CE1176 and BJOX2000, representative of clade C and CRF07, as shown in the examples herein). Neutralization assays may be carried out using any suitable host cells (e.g., TZM-bl cells (Seaman, et al. J. Virol. 84(3): 1439-52 (2010); NIH AIDS Reagent Program Catalog Number 8129)). HIV-1 pseudoviruses resulting in a significant output relative light units (RLU) (e.g., of $50\text{-}100\times10^{4}$ RLU) (i.e., indicating productive infection of cells) may then incubated with B cell culture supematants for an appropriate time and temperature (e.g., one (1) h at 37% (5% $CO_2$)) before the addition of host cells (e.g., 3000 TZM-bl cells). Incubation for an appropriate time (e.g., 72 hours) typically follows, after which the supernatant may be removed and Steadylite reagent (Perkin Elmer) added (e.g., 15 µl). Luciferase activity may then detected (e.g., five minutes later) on a Synergy microplate luminometer (BioTek). Decreased luciferase activity indicates a lesser amount of virus being released by the cells and virus neutralization. For instance, if the base RLU for a particular psuedovirus is $50\text{-}100\times10^{4}$ RLU, a neutralizing antibody may be determined to decrease the RLU for that pseudovirus to $25\text{-}50\times10^{4}$ RLU (i.e., a 50% decrease), or less. Using such systems, supematants capable of cross-neutralizing strains may be identified, further harvested, and tested for their ability to neutralize other pseudoviruses.

Figure 3:
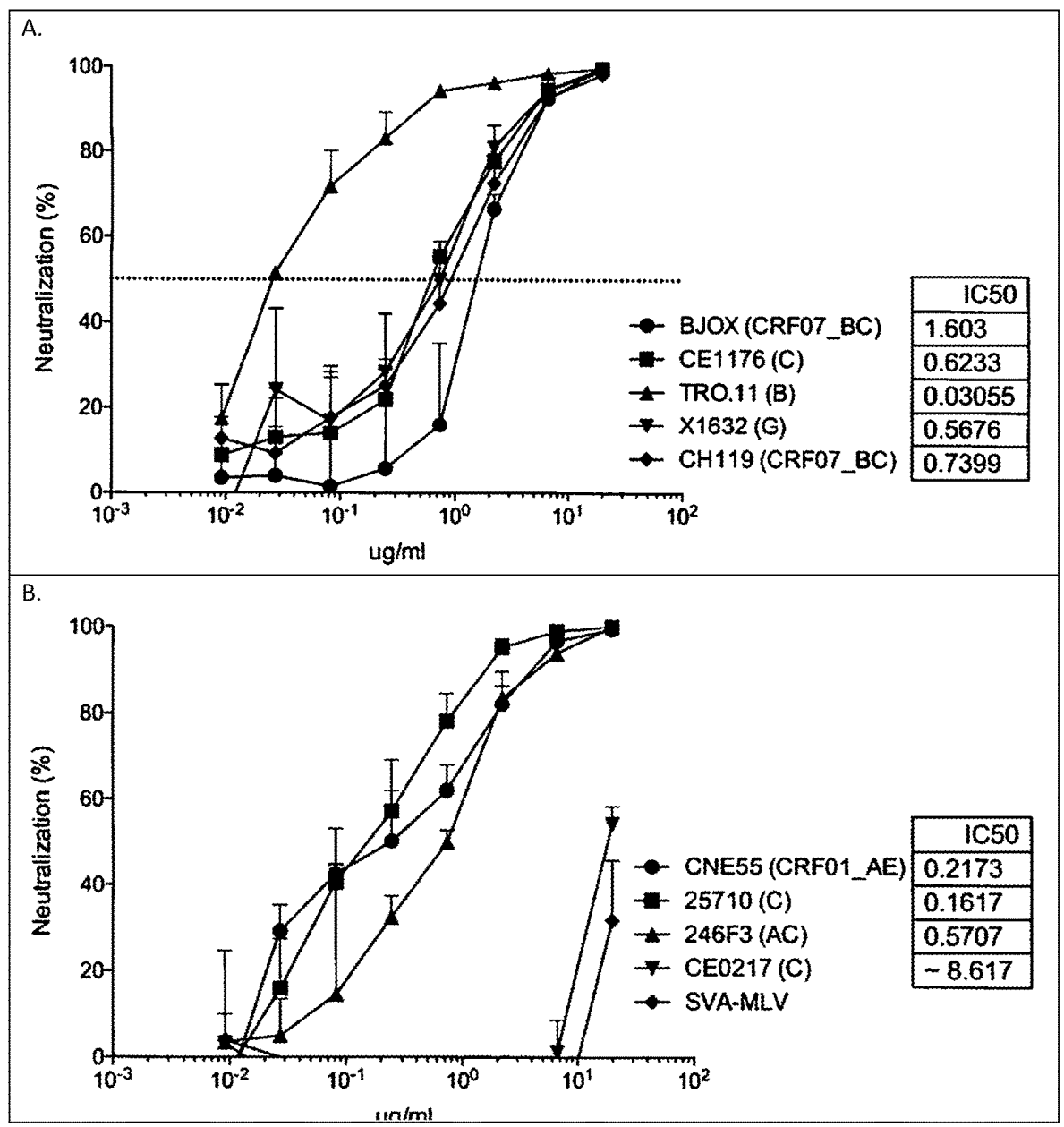
FIGS. 3A-B show the results of neutralization of a panel of nine (9) HIV-1 pseudoviruses (and MLV as negative control) from the Global Panel of HIV-1 reference strains by different concentration (in µg/ml) of the monoclonal antibody LN01. IC50 values indicate the concentration of monoclonal antibody capable of neutralizing 50% of viral infection. Error bars indicate the standard deviation of duplicates.
Figure 4:
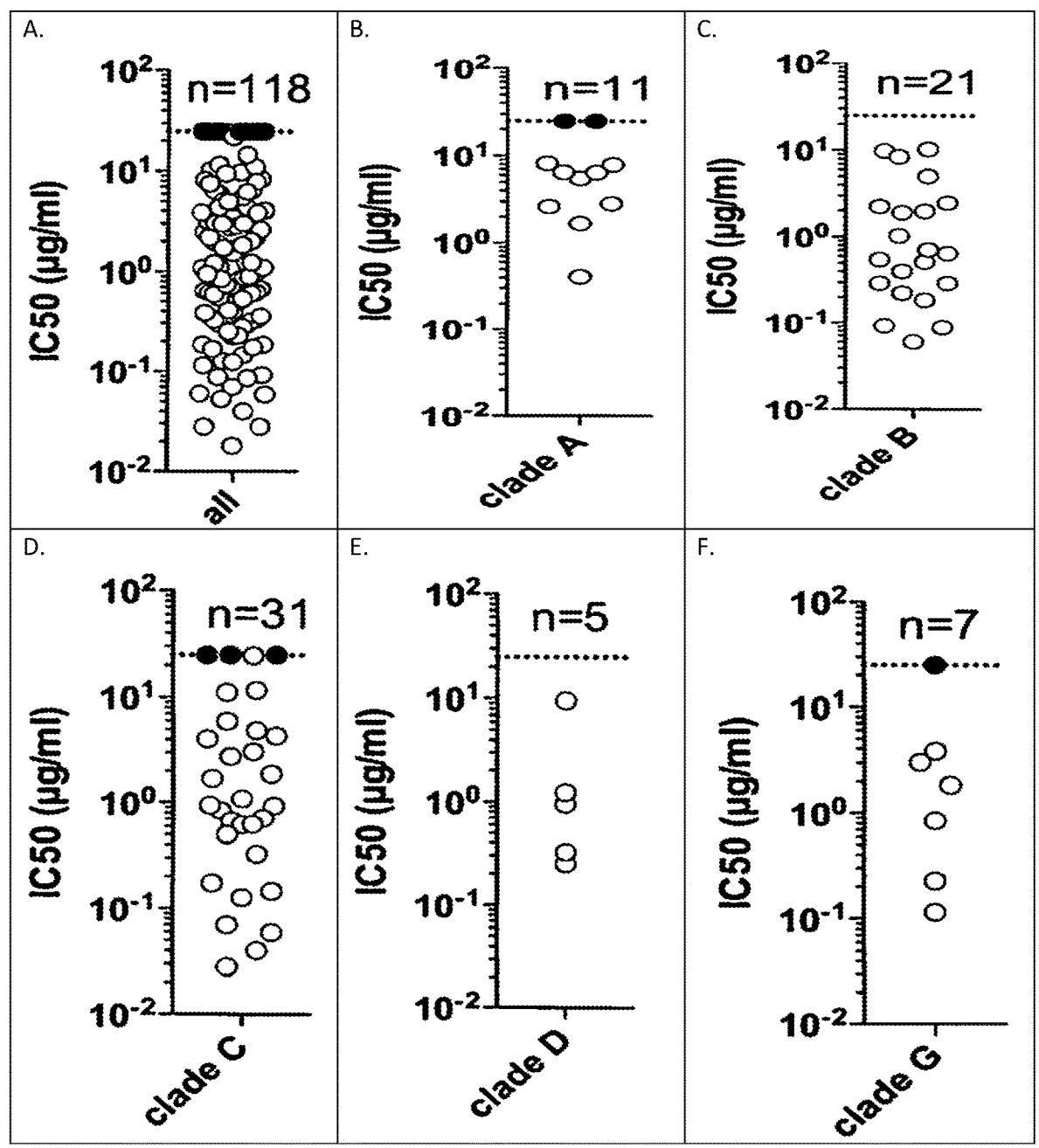
FIG. 4 shows the results of neutralization of a multi-clade panel of 118 HIV-1 pseudoviruses by the monoclonal antibody LN01. IC50 values indicate the concentration of monoclonal antibody capable of neutralizing 50% of viral infection.

The antibodies derived from such neutralizing antibody-containing cultures may then be further characterized by determining the amino acid and nucleotide sequences of the antibody variable and complementarity determining regions (CDRs) regions. Using these techinques, the HIV-neutralizing binding agent termed "LN01" was identified as an IgG3-type fully human monoclonal antibody having the CDR, VH and VL sequences shown in Table 1 (SEQ ID NOS. 1-7 and/or GTY). LN01 was determined to be derived from the IGHV4-39*07 and IGKV1-39*01 germline genes and highly somatically mutated in variable genes of both heavy chain (28%) and kappa light chain (27%) compared to germ line. LN01 was also found to possess a long heavy-chain complementarity-determining 3 region ("CDR H3") loop composed of 20 amino acids. In some embodiments, the variable heavy chain ($V_H$) and variable light chain ($V_L$) genes of a binding agent may then be cloned into an IgG expression vector of the same or a different isotype. As shown in the examples, for instance, nucleic acids encoding LN01 CDRs (Table 3) were cloned into IgG1 backbone, and the recombinant IgG1-based antibody (IgG1 LN01) was produced by transfecting appropriate host cells (e.g., Expi293F cells). The antibody full-length IgG1-based antibody may then be purified using standard techniques (e.g., a full-length IgG1-based antibody may be purified using a recombinant protein-A column (GE-Healthcare)). The recombinantly-produced IgG1 antibody may then be tested against any of a panel of pseudoviruses such as any of those described herein (e.g., the Global Panel of nine (9) HIV-1 reference pseudoviruses used in the examples) on an appropriate host cell (e.g., TZM-bl cells). In preferred embodiments, the binding agent will exhibit the ability to neutralize a majority (i.e., at least about 50% or greater) of the pseudovirus panel members (e.g., comprising nine, 12 or 118 members) without neutralizing a negative control virus (e.g., MLV pseudovirus). It is preferred that the binding agent exhibit the ability to neutralize a majority of such viruses (e.g., neutralization of greater than about 50%, such as any of about 60%, 70%, 80%, 90%, 95%, 99%, or 100%) with $IC_{50}$ values considered neutralizing (see below). For example, in some embodiments, a binding agent of this disclosure may exhibit neutralization of HIV-1 pseudoviruses BJOX (CRF07_BC), CE1176, TRO.11 (B), X1632 (G), CH119 (CRF07_BC), CNE55 (CRF01_AE), 25710 (C), CD0217(C) but not of the control virus SVA-MLV at about $10^0$ μg/ml or less (FIG. 3). In some embodiments, neutralization of the HIV-1 pseudoviruses viruses may be observed where the antibody concentration is from $10^2$-$10^0$ μg/ml, or between $10^0$-$10^1$ g/ml (FIG. 3). In some such embodiments, the percent neutralization by the binding agent is at least about 50% (FIG. 3). In some embodiments, infection of one HIV-1 isolate is considered neutralized by a binding agent (e.g., antibody) at an $IC_{50}$ of less than 25 μg/ml, if infection of at least one isolate of this isolate is neutralized with an $IC_{50}$ of less than 25 μg/ml. In some embodiments, the binding agent may be considered neutralizing where a majority of the 118 HIV-1 pseudoviruses listed in FIG. 4 are considered neutralized at an $IC_{50}$ of less than 25 μg/ml, such as about 10 μg/ml, 9 μg/ml, 8 μg/ml, 7 μg/ml, 6 μg/ml, 5 μg/ml, 4 μg/ml, 3 μg/ml, 2 μg/ml, 1 μg/ml, 0.9 μg/ml, 0.8 μg/ml, 0.7 μg/ml, 0.6 μg/ml, 0.5 μg/ml, 0.4 μg/ml, 0.3 μg/ml, 0.2 μg/ml, 0.1 μg/ml, 0.09 μg/ml, 0.08 μg/ml, 0.07 μg/ml, 0.06 μg/ml, 0.05 μg/ml, 0.04 μg/ml, 0.03 μg/ml, 0.02 μg/ml, or 0.01 μg/ml. In preferred embodiments, the binding agent may neutralize HIV-1 pseudovirus strains of ID 6535.3, QH0692.42, SC422661.8, PVO.4, TRO.11, PEJ04541.67, W1T04160.33, 1006_11_C3_1601, 1054_07_TC4_1499, 1056_TA11_1826, 1012_11_TC21_3257, 6244_13_B5_4576, SC05_8C11_2344, Du156.12, Du172.17, Du422.1, ZM197M.PB7, ZM214M.PL15, ZM233M.PB6, ZM249M.PL1, ZM109F.PB4, ZM135M.PL10a, HIV-0013095-2.11, HIV-16055-2.3, HIV-16845-2.22, Ce1086_B2, Cell76_A3, Ce0682_E4, Ce1172_H1, ZM247v1(Rev-), 3016.v5.c45, A07412M1.vrc12, 231966.c02, CNE20, CNE21, CNE17, CNE30, CNE53, CNE58, 9004SS_A3_4, 928-28, 263-8, T255-34, 211-9, 235-47, CNE8, C1080.c03, R2184.c04, R1166.c01, C2101.c01, C3347.c11, BJOX015000.11.5, BJOX010000.06.2, BJOX025000.01.1, BJOX028000.10.3, X1193_c1, X2131_C1_B5, P1981_C5_3, 6952.v1.c20, and 0815.v3.c3 at an $IC_{50}$ of less than or about 1 μg/ml (FIG. 4). In some preferred embodiments, the binding agent may neutralize HIV-1 pseudovirus strains of ID QH0692.42, SC422661.8, PVO.4, TRO.11, PEJ04541.67, WITO4160.33, 1006_11_C3_1601, 1054_07_TC4_1499, 1056_TA11_1826, 6244_13_B5_4576, SC05_8C11_2344, Du156.12, Du172.17, ZM197M.PB7, HIV-0013095-2.11, HIV-16055-2.3, HIV-16845-2.22, Ce1086_B2, Cel172_H1, ZM247v1(Rev-), 3016.v5.c45, A07412M1.vrc12, CNE20, CNE21, CNE53, CNE58, 9004SS_A3_4, 928-28, 263-8, T255-34, CNE8, C1080.c03, BJOX015000.11.5, BJOX010000.06.2, BJOX025000.01.1, BJOX028000.10.3, X2131_C1_B5, P1981_C5_3, 6952.v1.c20, and 0815.v3.c3 at an $IC_{50}$ of less than or about 0.5 μg/ml (FIG. 4). In some preferred embodiments, the binding agent may neutralize HIV-1 pseudovirus strains of ID 1054_07_TC4_1499, 1056_TA11_1826, 6244_13_B5_4576, Du172.17, HIV-0013095-2.11, HIV-16845-2.22, Ce1172_H1, CNE20, CNE21, 928-28, CNE8, P1981_C5_3 at an $IC_{50}$ of less than or about 0.1 μg/ml (FIG. 4). It is further preferred that the binding agent not exhibit clade-dependency. For instance, in some embodiments, the binding agent may exhibit the ability to neutralize pseudoviruses of HIV-1 Clades B, B (T/F), C, C (T/F), D, D (T/F), BC, A, A (T/F), CRF02_AG, CRF01_Ae, CRF01_AE (T/F), G, CD, AC and ACD (FIG. 4). In some preferred embodiments, the binding agent may neutralize at least one pseudovirus in each of clades B, B (T/F), C, C (T/F), D, BC, A, A (T/F), CRF02_AG, CRF01_Ae, CRF01_AE (T/F), G, CD, and ACD at an $IC_{50}$ of less than or about 1 μg/ml (FIG. 4). In some preferred embodiments, the binding agent may neutralize at least one pseudovirus in each of clades B, B (T/F), C, C (T/F), D, BC, A (T/F), CRF02_AG, CRF01_Ae, CRF01_AE (T/F), G, CD, and ACD at an $IC_{50}$ of less than or about 0.5 μg/ml (FIG. 4). In some preferred embodiments, the binding agent may neutralize at least one pseudovirus in each of clades B (T/F), C, C (T/F), BC, A (T/F), CRF02_AG, CRF01_AE, CRF01_AE (T/F), G, and CD at an $IC_{50}$ of less than or about 0.1 μg/ml (FIG. 4). In some embodiments, the binding agent comprises any one or more of these properties and one or more of SEQ ID NOS. 1-32, preferably each of SEQ ID NOS. 1-7 and/or SEQ ID NOS. 8-9 and/or fragments and/or derivatives thereof. These are characteristics of LN01-type binding agents, such as IgG1 LN01, as shown in FIG. 4.

In some embodiments, the binding agents may be tested for neutralization capacity against HIV reference pseudoviruses (e.g., the above-described Global Panel of nine (9) HIV-1 reference pseudoviruses) using cells expressing or not expressing one or more types of Fc receptors (e.g., parental TZM-bl cells and TZM-bl cells expressing Fc-gamma receptor I (CD64) as in the examples; see e.g. Perez, et al. Utilization of immunoglobulin G Fc receptors by human immunodeficiency virus type 1: a specific role for antibodies against the membrane-proximal external region of gp41. J Virol 83, 7397-7410 (2009); NIH AIDS Reagent Program Catalog No. 11798). Enhanced neutralizing activity in cells expressing Fc receptors may provide antibodies a kinetic advantage for virus inhibition. This kinetic advantage could be unique to antibodies, whose epitopes are thought to be difficult to access or exposed for only a short time on intermediate conformations of the Env protein during an early stage of fusion. Fc-gamma receptors could also potentially facilitate HIV-1 neutralization is phagocytosis, thereby increasing neutralization capacity of the antibodies. To this point, HeLa cells, from which the TZM-bl cell line was constructed, are known to exhibit properties of nonprofessional phagocytes. Thus, it is possible that TZM-bl cells were converted to professional phagocytic cells by introducing Fc-gamma receptor on their surface. Any Fc-gamma-receptor-mediated antiviral effects on HIV-1 neutralizing antibodies, whether by entry inhibition or phagocytosis, might be beneficial in HIV treatment and vaccine regimens. Fc-gamma receptors are rarely expressed on CD4+ lymphocytes, but several other HIV-1-susceptible cell types express multiple Fc-gamma receptors and are involved in sexual transmission and the early establishment of long-lived viral reservoirs. In particular, macrophages are among the first infection-susceptible cells that the virus encounters after mucosal exposure, and are thought to serve as a long-lived virus reservoir in chronic infection. Macrophages, as well as certain subsets of monocytes and dendritic cells, are known to express multiple Fc-gamma receptors. It is also important to mention that Fc-gamma receptors play a role in regulating adaptive immunity and peripheral tolerance, by facilitating antigen uptake, antigen presentation, cell activation and B cell tolerance. Thus, is some embodiments, the binding agents described herein may be used in conjunction with agents that induce and/or enhance Fc receptor expression, including the introduction of nucleic acids encoding one or more Fc receptors with or in conjunction with treatment by the binding agents described herein.

The specificity of the binding agents described herein may be determined using any of the many techniques available to those of ordinary skill in the art. For instance, as shown in the examples herein, the specificity of a binding agent (e.g., IgG1 LN01 antibody), with respect to particular epitopes, may be ascertained using a panel of chimeric pseudoviruses (e.g., HIV-2/HIV-1 chimeras containing various segments of the HIV-1 MPER into the parental HIV-2/7312A) to test for neutralization capacity. For instance, the examples herein demonstrate that IgG1 LN01 antibody does not neutralize the parental HIV-2 7312A strain. However, IgG1 LN01 antibody was found to potently neutralize the chimeric virus 7312A.C4 in which six (6) residues of HIV-2 MPER (LASWVKYIQ (SEQ ID NO. 65)) were replaced by those of HIV-1 MPER region (ITKWLWYIK (SEQ ID NO. 66)). IgG1 LN01 antibodies was also found not to neutralize the chimeric virus 7312A.C6 in which only three (3) residues in the same region were replaced (ITSWIKYIQ (SEQ ID NO. 67)) (see, e.g., FIG. 7). A similar finding was obtained with the chimeric virus 7312A.C1C where the same six (6) changes to 7312A.C4 were combined with an additional seven (7) mutations in the N-terminal region. These results indicate that amino acid residues L679, W680 and K683 in the C-terminal region of gp41 MPER are involved in IgG1 LN01 antibody binding. Thus, in some embodiments, the binding agent exhibits the capacity to bind to and/or neutralize HIV expressing gp41 comprising the amino acid residues L679, W680 and K683 as found in the HIV-1 envelope amino acid sequence of GenBank Accession No. K03455 (NCBI GenPept Accession No. AAB50262), such as, for instance, SEQ ID NO. 68 (L679, W680 and K683 underlined):

(SEQ ID NO. 68)

1 MRVKEKYQHL WRWGWRWGTM LLGMLMICSA TEKLWVTVYY GVPVWKEATT TLFCASDAKA

61 YDTEVHNVWA THACVPTDPN PQEVVLVNVT ENFNMWKNDM VEQMHEDIIS LWDQSLKPCV

121 KLTPLCVSLK CTDLKNDTNT NSSSGRMIME KGEIKNCSFN ISTSIRGKVQ KEYAFFYKLD

181 IIPIDNDTTS YKLTSCNTSV ITQACPKVSF EPIPIHYCAP AGFAILKCNN KTFNGTGPCT

241 NVSTVQCTHG IRPVVSTQLL LNGSLAEEEV VIRSVNFTDN AKTIIVQLNT SVEINCTRPN

301 NNTRKRIRIQ RGPGRAFVTI GKIGNMRQAH CNISRAKWNN TLKQIASKLR EQFGNNKTII

361 FKQSSGGDPE IVTHSFNCGG EFFYCNSTQL FNSTWFNSTW STEGSNNTEG SDTITLPCRI

421 KQIINMWQKV GKAMYAPPIS GQIRCSSNIT GLLLTRDGGN SNNESEIFRP GGGDMRDNWR

481 SELYKYKVVK IEPLGVAPTK AKRRVVQREK RAVGIGALFL GFLGAAGSTM GAASMTLTVQ

541 ARQLLSGIVQ QQNNLLRAIE AQQHLLQLTV WGIKQLQARI LAVERYLKDQ QLLGIWGCSG

601 KLICTTAVPW NASWSNKSLE QIWNHTTWME WDREINNYTS LIHSLIEESQ NQQEKNEQEL

661 LELDKWASLW NWFNITNWLW YIKLFIMIVG GLVGLRIVFA VLSIVNRVRQ GYSPLSFQTH

721 LPTPRGPDRP EGIEEEGGER DRDRSIRLVN GSLALIWDDL RSLCLFSYHR LRDLLLIVTR

781 IVELLGRRGW EALKYWWNLL QYWSQELKNS AVSLLNATAI AVAEGTDRVI EVVQGACRAI

841 RHIPRRIRQG LERILL, or equivalents thereof as would be understood by those of ordinary skill in the art. An exemplary gp41 polypeptide is shown below:

(SEQ ID NO. 69)

AVGIGALFLGFLGAAGSTMGAASMTLTVQARQLLSGIVQQQNNLLRAIEA

QQHLLQLTVWGIKQLQARILAVERYLKDQQLLGIWGCSGKLICTTAVPWN

ASWSNKSLEQIWNNMTWMEWDREINNYTSLIHSLIEESQNQQEKNEQELL

ELDKWASLWNWFNITNWLWYIKLFIMIVGGLVGLRIVFAVLSIVNRVRQ

G.

Another exemplary gp41 polypeptide has GenBank Accession No. 1103299B (Meusing, et al. Nature 313 (6002), 450-458 (1985)). Exemplary equivalents to amino acid residues L679, W680 and K683 are the underlined amino acid residues L168, W169 and K172 of SEQ ID NO. 14 (as well as GenBank Accession No. 1103299B). In some embodiments, the binding agent exhibits the capacity to bind to and/or neutralize HIV expressing amino acid sequence ITKWLWYIK (SEQ ID NO. 66). In some embodiments, the binding agent exhibits the capacity to bind to and/or neutralize HIV expressing amino acid sequence ITKWLWYIK (SEQ ID NO. 66) but not LASWVKYIQ (SEQ ID NO. 65) and/or ITKWIKYIQ (SEQ ID NO. 67). In some embodiments, the epitope(s) to which the binding agent binds (i.e., has specificity) includes the amino acid residues L679, W680 and K683, or equivalents thereof of, HIV env (e.g., SEQ ID NO. 68. With respect gp41, in preferred embodiments, the epitope(s) to which the binding agent binds (i.e., has specificity) includes the amino acid residues L168, W169 and K172 of SEQ ID NO. 69, or equivalents thereof. In some embodiments, a binding agent of this disclosure may comprise these binding specificities along with the neutralization characteristics described above (i.e., neutralization of HIV-1 pseudoviruses BJOX (CRF07_BC), CE1176, TRO.11 (B), X1632 (G), CH119 (CRF07_BC), CNE55 (CRF01_AE), 25710 (C), CD0217(C) but not of the control virus SVA-MLV at a concentration is from $10^2$-$10^0$ ug/ml, or between $10^0$-$10^1$ ug/ml, to at least about 50% (FIG. 3), as well as the neutralization a majority of the 118 HIV-1 pseudoviruses listed in FIG. 4 at an $IC_{50}$ of less than 25 µg/ml).

Peptide microarrays may alternatively and/or also be used to determine the binding specificity of the binding agents described herein. One or more peptide microarrays may be designed such that overlapping peptides encompassing the entire amino acid sequence of a HIV polypeptide. For instance, as shown in the examples herein, a peptide microarray formed by 1423 overlapping (by 12 amino acids) 15-mer peptides covering the consensus HIV-1 Env gp160 sequences for clades A, B, C, D, group M, CRF01_AE and CRF02_AG was utilized to test the specificity of binding agent IgG1 LN01. In the examples herein, the peptides were printed onto 3D-Epoxy glass slides and were analyzed with a GenePix 4000B scanner (Tomaras, G. D. et al. Polyclonal B cell responses to conserved neutralization epitopes in a subset of HIV-1-infected individuals. J Virol 85, 11502-11519 (2011)) but any suitable system available to those of ordinary skill in the art may be utilized. The binding agent may be tested along with a control binding agent (e.g., in the examples herein IgG01 LN01 was tested at 20 µg/ml in parallel with a control antibody called 7B2 haivng specificity for the immunodominant region of gp41). The binding of the binding agent to the peptides in the microarray may be detected by any suitable process, including by incubation with DyLight 649-labeled goat anti-human IgG as in the examples herein. Fluorescence intensity may be measured by any suitable system, such as a GenePix 4000B scanner/GenePix software as in the examples herein (see, e.g., FIG. 8). As shown in the examples herein, IgG1 LN01 antibody did not clearly react with any of the peptides in that library, while the control antibody (7B2) strongly reacted with 190-195 peptides that spanned the gp41 immunodominant region, indicating that the IgG1 LN01 antibody does not recognize a linear epitope in HIV-1 Env. Similar tests may also be performed on any of the binding agents contemplated herein.

The specificity of a binding agent may also be tested for binding to soluble trimers representing HIV proteins (e.g., soluble, cleaved SOSIP.664 gp140 trimers based on the subtype A transmitted/founder strain, BG505 as used in the examples herein). Preferred trimers (such as those used in the examples herein) are those being highly stable, homogenous and closely resembling native virus spikes when visualized by negative stain electron microscopy (EM) (Sanders, R. W. et al. A next-generation cleaved, soluble HIV-1 Env trimer, BG505 SOSIP.664 gp140, expresses multiple epitopes for broadly neutralizing but not non-neutralizing antibodies. PLoS Pathog. 9, e1003618 (2013)). Typically, broadly neutralizing antibodies against multiple neutralizing epitopes on HIV-1 Env will be highly reactive with such trimers (e.g., the BG505 SOSIP.664 gp140 trimers, including quaternary epitopes antibodies (CH01, PG9, PG16 and PGT145)). Conversely, non-neutralizing antibodies (NAbs) to the CD4-binding site, CD4-induced epitopes or gp41 ectodomain would not (and did not in the example) react with the trimers, even when their epitopes were present on simpler forms of Env (e.g., gp120 monomers or dissociated gp41 subunits). The examples also included a test, which may be used in testing any of binding agents described herein, in which the MPER was also deleted to improve trimer solubility and reduce aggregate formation. The binding agents may also be tested for binding to such trimers in the presence or absence of soluble CD4 (sCD4). The examples herein describe the testing of the IgG1 LN01, PGT145 (V1-V2 glycan specific), PGT151 (binding to a site at the interface between gp120 and gp41) and 17b (binding to a CD4 binding induced site) antibodies for binding to BG505 SOSIP.664 gp140 trimers in the presence or absence of sCD4 (measured by surface plasmon resonance (SPR)). As shown therein, the PGT145 and PGT151 antibodies reacted strongly to BG505 SOSIP.664 gp140 trimers in the presence and absence of sCD4; 17b reacted to BG505 SOSIP.664 gp140 trimers only in the presence of sCD4; and IgG1 LN01 did not react with BG505 SOSIP.664 gp140 trimers neither in the presence nor in the absence of sCD4 (see, e.g., FIG. 9). Similar tests may also be performed on any of the binding agents contemplated herein.

Figure 10:
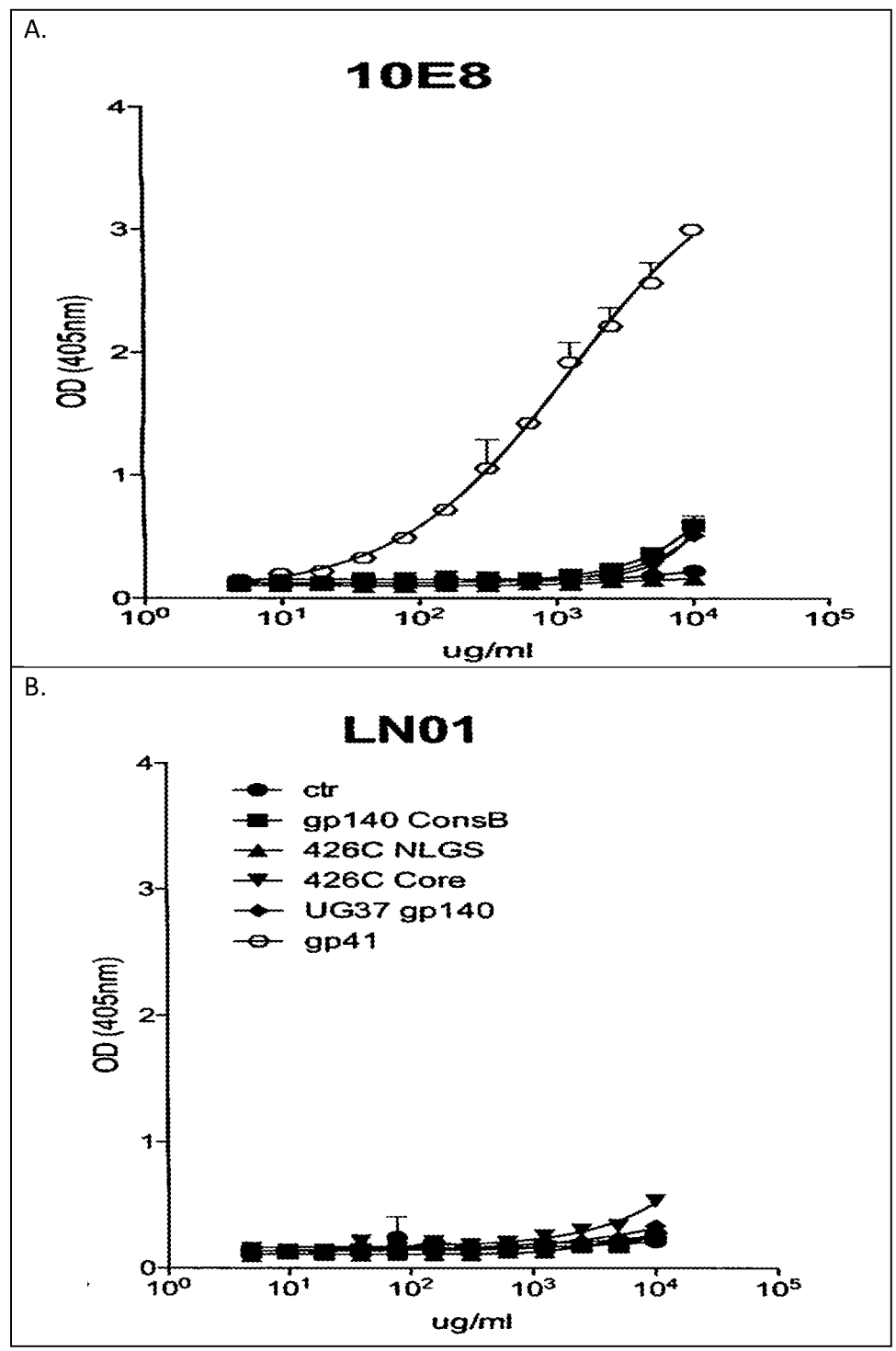
FIGS. 10A-B show the binding, as measured by ELISA, of LN01 and 10E8 (MPER-specific broadly neutralizing antibody) antibodies to a set of HIV-1 Env antigens and a negative control (Ctr) antigen. 10E8 antibody reacted to the recombinant ecto-domain of gp41 that contains the MPER region.
Figure 11:
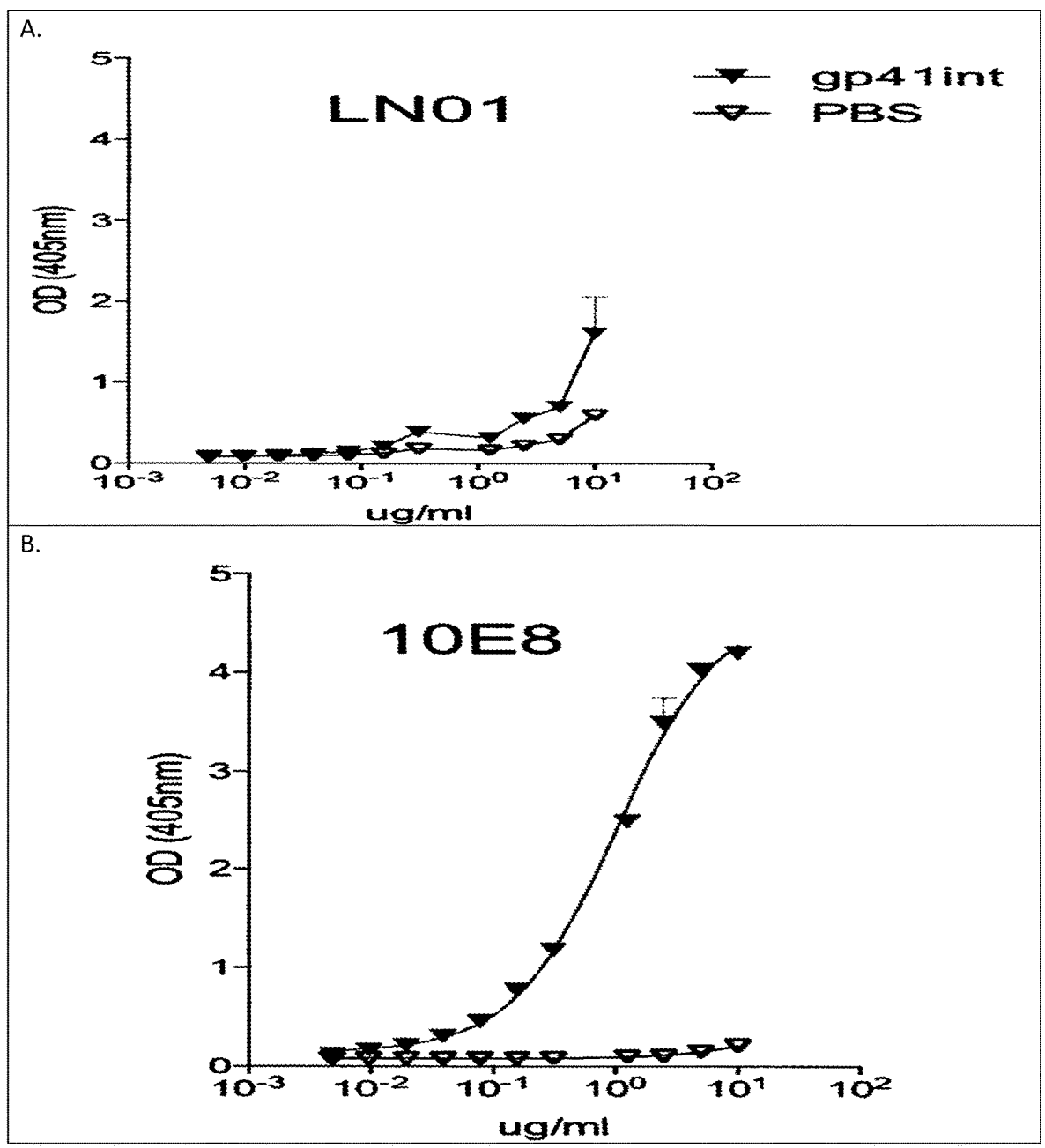
FIGS. 11A-B shows the binding, as measured by ELISA, of LN01 and 10E8 monoclonal antibodies to a fusion intermediate gp41 (gp41int) or uncoated plates as a negative control (PBS). 10E8 antibody reacted to gp41 that contains the MPER region.

Other assay systems such as ELISA may also be used to test the binding agents contemplated herein. For instance, as shown in the examples, the IgG1 LN01 antibody, in parallel with MPER-specific 10E8 antibody (Huang, J. et al. Broad and potent neutralization of HIV-1 by a gp41-specific human antibody. Nature 491, 406-412 (2012)), was tested by ELISA against a panel of HIV-1 antigens (ConsB, consensus clade B gp140, 426c, clade C gp140, 426c-NLGS, 426c gp140 where the N-linked glycosylation sites were removed, 426c core, gp140 where the V loops were removed, UG37 gp140, clade A and gp41, recombinant ecto-domain of gp41, amino acids 541-682 from HxB2 strain, Vybion). None of the tested antigens was recognized by IgG1 LN01 antibody by ELISA (see, e.g., FIG. 10). Conversely, 10E8 antibody reacted to the recombinant ecto-domain of gp41. The results presented in the examples therefore indicate that IgG1 LN01 antibody might recognize an epitope in the MPER of gp41 different from 10E8. The examples herein also demonstrate the testing of IgG1 LN01 antibody against a fusion intermediate gp41 and uncoated plates (PBS), called gp41int (Lai, R. P. J. et al. A fusion intermediate gp41 immunogen elicits neutralizing antibodies to HIV-1. J Biol Chem 289, 29912-29926 (2014)), using ELISA. The gp41int antigen is recognized with high affinity by MPER antibodies 4E10, 2F5 and 10E8. While 10E8 reacted to gp41int by ELISA, IgG1 LN01 antibody did not (see, e.g., FIG. 11). These results indicate that IgG1 LN01 antibody recognizes a conserved epitope, possibly in the MPER region, that is not readily displayed in any of the antigens tested. Similar tests may be performed on any of the binding agents contemplated herein.

The term "binding affinity" and/or $K_D$ refers to the dissociation rate of a particular antibody-antigen interaction. The $K_D$ is the ratio of the rate of dissociation ("off-rate ($k_d$)") to the association rate ("on-rate ($k_a$)"). $K_D$ therefore equals $k_d/k_a$ and is expressed as a molar concentration (M). Thus, the smaller the $K_D$, the stronger the affinity of binding. For example, a a $K_D$ of 1 mM indicates weak binding as compared to a $K_D$ of 1 nM. $K_D$ values for antibodies can be determined using methods well established in the art such as by using a Biacore® system. In some embodiments, the binding agents described herein may be compared with another binding agent with reference to the respective $K_D$ values of each. These properties may be combined with other characteristics such as neutralization capacity and/or epitope specificity in order to compare binding agents to one another. Accordingly, binding agents having a similar $K_D$ to those described herein, perhaps also sharing the neutralization capacity and epitope specificity described herein (e.g., as exhibited by LN01), are also contemplated as part of this disclosure.

Any of the amino acid sequences of Tables 1 (and/or any one or more fragments and/or derivatives thereof) may be also substituted by any other amino acid as desired by one of ordinary skill in the art. For example, one of skill in the art may make conservative substitutions by replacing particular amino acids with others as shown in Table 2 below. The specific amino acid substitution selected may depend on the location of the site selected. An amino acid substitution may be said to "correspond to" where one of ordinary skill in the art could ascertain a significant amount of similarity between the amino acid sequences surrounding the amino acid being substituted. For instance, a particular amino acid sequence may correspond to another where two, three, four or more N-terminal and C-terminal amino acids surrounding the amino acid being substituted are the same or similar (e.g., as described in Table 2) in the polypeptides being compared. Conservative amino acid substitutions may involve a substitution of a native amino acid residue with a non-native residue such that there is little or no effect on the size, polarity, charge, hydrophobicity, or hydrophilicity of the amino acid residue at that position and, in particular, does not result in, e.g., decreased HIV neutralization capacity and/or different epitope specificity.

TABLE 2

| Original Amino Acid Residue | Exemplary Conservative Substitutions of the Original Amino Acid Residue | Preferred Conservative Substitution of the Original Amino Acid Residue |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |

TABLE 2-continued

| Original Amino Acid Residue | Exemplary Conservative Substitutions of the Original Amino Acid Residue | Preferred Conservative Substitution of the Original Amino Acid Residue |
|---|---|---|
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In certain embodiments, a nucleic acid molecule encoding one or more binding agents described herein may be inserted into one or more expression vectors, as discussed below in greater detail. In such embodiments, the binding agent may be encoded by nucleotides corresponding to the amino acid sequence. The particular combinations of nucleotides (codons) that encode the various amino acids (AA) are well known in the art, as described in various references used by those skilled in the art (e.g., Lewin, B. Genes V, Oxford University Press, 1994). The nucleotide sequences encoding the amino acids of said binding agents may be ascertained with reference to Table 3, for example. Nucleic acid variants may use any combination of nucleotides that encode the binding agent.

TABLE 3

Codons Encoding Amino Acids (AA)

| AA | Codon | AA | Codons | AA | Codons | AA | Codons |
|---|---|---|---|---|---|---|---|
| Phe (F) | TTT | Ser (S) | TCT | Tyr (Y) | TAT | Cys (C) | TGT |
|  | TTC |  | TCC |  | TAC |  | TGC |
| Leu (L) | TTA |  | TCA | TERM | TAA | TERM | TGA |
|  | TTG |  | TCG |  | TAG | Trp (W) | TGG |
|  | CTT | Pro (P) | CCT | His (H) | CAT | Arg (R) | CGT |
|  | CTC |  | CCC |  | CAC |  | CGC |
|  | CTA |  | CCA | Gln (Q) | CAA |  | CGA |
|  | CTG |  | CCG |  | CAG |  | CGG |
| Ile (I) | ATT | Thr (T) | ACT | Asn (N) | AAT | Ser (S) | AGT |
|  | ATC |  | ACC |  | AAC |  | AGC |
|  | ATA |  | ACA | Lys (K) | AAA | Arg (R) | AGA |
| Met (M) | ATG |  | ACG |  | AAG |  | AGG |
| Val (V) | GTT | Ala (A) | GCT | Asp (D) | GAT | Gly (G) | GGT |
|  | GTC |  | GCC |  | GAC |  | GGC |
|  | GTA |  | GCA | Glu (E) | GAA |  | GGA |
|  | GTG |  | GCG |  | GAG |  | GGG |

Those of ordinary skill in the art understand that the nucleotide sequence encoding a particular amino acid sequence may be easily derived from the amino acid sequence of any of SEQ ID NOS. 1-7 and the information presented in Table 4. For instance, it may be deduced from the amino acid sequence GDSVSNDNYY (SEQ ID NO.: 1) and the information presented in Table 4 that the amino acid sequence may be encoded by the nucleotide sequence GGTGACTCAGTCAGTAATGATAATTATTAT (SEQ ID NO.: 33). Those of ordinary skill in the art would understand that nucleotide sequences encoding SEQ ID NOS. 2-32 and 34-36 may be deduced in the same way, and such nucleotide sequences are contemplated herein. Table 4 provides exemplary nucleic acid sequences encoding the amino acid sequences shown in Table 1 (SEQ ID NOS. 1-32):

TABLE 4

| LN01 region | Amino Sequence | Exemplary Nucleotide Sequence |
|---|---|---|
| LN01 CDRH1 | GDSVSNDNYY (SEQ ID NO. 1) | GGTGACTCAGTCAGTAATGATA ATTATTAT (SEQ ID NO. 33) |
| LN01 CDRH2 | IYYSGTT (SEQ ID NO. 2) | ATCTATTACAGCGGCACAACC (SEQ ID NO. 34) |
| LN01 CDRH3 | VRMPSHGFWSTSFSYWYF DL (SEQ ID NO. 3) | GTTCGCATGCCCAGTCACGGAT TTTGGAGTACTTCTTTCTCTTAC TGGTATTTCGATCTC (SEQ ID NO. 35) |
| LN01 CDRL1 | QSVTKY (SEQ ID NO. 4) | CAGAGTGTCACCAAATAT (SEQ ID NO. 36) |
| LN01 CDRL2 | GTY | GGGACTTAT |
| LN01 CDRL2 (long) | LIYGTYTLL (SEQ ID NO. 5) | CTCATCTATGGGACTTATACTT TACTC (SEQ ID NO. 37) |
| LN01 CDR3 | QQAHSTPWT (SEQ ID NO. 6) | CAACAGGCTCACAGTACTCCC TGGACC (SEQ ID NO. 38) |
| LN01 Variable Heavy (VH) | EVQLVESGPGLVQPWGTLSL TCRVSGDSVSNDNYYWAWI RQTPGRELQVIGTIYYSGTTY YNPSLRNRVTISLDKSVNVVS LRLGSVSAADTAQYYCVRMP SHGFWSTSFSYWYFDLWGR GHFVAVSW (SEQ ID NO. 7) | GAGGTGCAGCTGGTGGAGTCG GGCCCAGGACTGGTGCAGCCC TGGGGGACCCTGTCCCTCACCT GTCGTGTCTCTGGTGACTCAGT CAGTAATGATAATTATTATTGGG CCTGGATTCGCCAGACCCCCGG GAGGGAACTGCAGGTCATCGGA ACTATCTATTACAGCGGCACAAC CTACTACAATCCGTCGCTCAGG AATCGAGTCACGATCTCATTGG ACAAGTCCGTCAATGTGGTCTC CCTGAGATTGGGGTCTGTGAGT GCCGCGGACACGGCCCAATATT ATTGCGTTCGCATGCCCAGTCA CGGATTTTGGAGTACTTCTTTCT CTTACTGGTATTTCGATCTCTGG GGCCGTGGTCATTTCGTCGCTG TCTCCTGG (SEQ ID NO. 39) |
| LN01 Variable Light (VL) | DIQMTQSPSSLSASVGDKVTI TCRASQSVTKYLNWYQFKT GQAPRILIYGTYTLLSGVSPR FSGAGSGSLYTLTITNIQPED FATYYCQQAHSTPWTFGQG THVAAN (SEQ ID NO. 8) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO. 40) |
| LN01 variant 7 Variable Heavy (V$_H$) (CDRH1, CDRH2 and CDRH3 underlined) | EVQLVESGPGLVQPWGTLSL TCRVSGDSVSNWNYYWAWI RQTPGRELQVIGTIYYSGTTY YNPSLRNRVTISLDKSVNVVS LRLGSVSAADTAQYYCVRMP SHGFWSTSFSYWYFDLWG RGHFVAVSW (SEQ ID NO.: 9) | GAAGTGCAGCTGGTGGAATCTG GCCCTGGCCTGGTGCAGCCTTG GGGCACACTGAGCCTGACCTGT AGAGTGTCCGGCGACAGCGTGT CCAACTGGAACTACTACTGGGC CTGGATCCGGCAGACCCCCGG CAGAGAACTGCAAGTGATCGGC ACCATCTACTACAGCGGCACAA CCTACTACAACCCCAGCCTGCG GAACAGAGTGACCATCAGCCTG GACAAGAGCGTGAACGTGGTGT CCCTGAGACTGGGCTCTGTGTC TGCCGCCGATACCGCCCAGTAC TACTGTGTGCGGATGCCCAGCC ACGGCTTCTGGTCTACCAGCTT CAGCTACTGGTACTTCGACCTG TGGGGCAGAGGCCACTTCGTG GCCGTGTCTTGG (SEC) ID NO. 41) |

TABLE 4-continued

| LN01 region | Amino Sequence | Exemplary Nucleotide Sequence |
|---|---|---|
| LN01 variant 7 Variable Light (V_L) (CDRL1, CDRL2 and CDRL3 underlined) | DIQMTQSPSSLSASVGDKVTI TCRAS<u>QSVTKYLN</u>WYQFKT GQAPRIL<u>IYGTYTLL</u>SGVSPR FSGAGSGSLYTLTITNIQPED FATYYC<u>QQAHSTPWT</u>FGQG THVAAN (SEQ ID NO.: 10) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO. 42) |
| LN01 variant 8 Variable Heavy (V_H) (CDRH1, CDRH2 and CDRH3 underlined) | EVQLVESGPGLVQPWGTLSL TCRVS<u>GDSVSNDWYY</u>WAWI RQTPGRELQVIGT<u>IYYSGTTY YNPSLRN</u>RVTISLDKSVNVVS LRLGSVSAADTAQYYC<u>VRMP SHGFWSTSFSYWYFDL</u>WGR GHFVAVSW (SEQ ID NO.: 11) | GAAGTGCAGCTGGTGGAATCTG GCCCTGGCCTGGTGCAGCCTTG GGGCACACTGAGCCTGACCTGT AGAGTGTCCGGCGACAGCGTGT CCAACGACTGGTACTACTGGGC CTGGATCCGGCAGACCCCCGG CAGAGAACTGCAAGTGATCGGC ACCATCTACTACAGCGGCACAA CCTACTACAACCCCAGCCTGCG GAACAGAGTGACCATCAGCCTG GACAAGAGCGTGAACGTGGTGT CCCTGAGACTGGGCTCTGTGTC TGCCGCCGATACCGCCCAGTAC TACTGCGTGCGGATGCCCAGCC ACGGCTTCTGGTCTACCAGCTT CAGCTACTGGTACTTCGACCTG TGGGGCAGAGGCCACTTCGTG GCCGTGTCTTGG (SEQ ID NO. 43) |
| LN01 variant 8 Variable Light (V_L) (CDRL1, CDRL2 and CDRL3 underlined) | DIQMTQSPSSLSASVGDKVTI TCRAS<u>QSVTKYLN</u>WYQFKT GQAPRIL<u>IYGTYTLL</u>SGVSPR FSGAGSGSLYTLTITNIQPED FATYYC<u>QQAHSTPWT</u>FGQG THVAAN (SEQ ID NO.: 12) | GACATCCAGATGACCCAGAGCC CCAGCAGCCTGTCTGCCAGCGT GGGCGACAAAGTGACCATCACC TGTCGGGCCAGCCAGAGCGTG ACCAAGTACCTGAACTGGTATC AGTTTAAGACCGGCCAGGCCCC CAGAATCCTGATCTACGGCACC TACACCCTGCTGAGCGGCGTGT CCCCTAGATTCTCTGGCGCCGG AAGCGGCAGCCTGTACACCCTG ACAATCACCAACATCCAGCCCG AGGACTTCGCCACCTACTACTG CCAGCAGGCCCACAGCACCCCT TGGACATTTGGCCAGGGAACAC ACGTGGCCGCCAAC (SEQ ID NO. 44) |
| LN01 variant 38 Variable Heavy (V_H) (CDRH1, CDRH2 and CDRH3 underlined) | EVQLVESGPGLVQPWGTLSL TCRVS<u>GDSVSNDNYY</u>WAWI RQTPGRELQVIGT<u>IYYSGTTY YNPSLRN</u>RVTISLDKSVNVVS LRLGSVSAADTAQYYC<u>VRMP SHGFWSTSFSYWYFDL</u>WGR GHFVAVSW (SEQ ID NO.: 13) | AAGTGCAGCTGGTGGAATCTGG CCCTGGCCTGGTGCAGCCTTGG GGCACACTGAGCCTGACCTGTA GAGTGTCCGGCGACAGCGTGTC CAACGACAACTACTACTGGGCC TGGATCCGGCAGACCCCCGGC AGAGAACTGCAAGTGATCGGCA CCATCTACTACAGCGGCACAAC CTACTACAACCCCAGCCTGCGG AACAGAGTGACCATCAGCCTGG ACAAGAGCGTGAACGTGGTGTC CCTGAGACTGGGCTCTGTGTCT GCCGCCGATACCGCCCAGTACT ACTGCGTGCGGATGCCCAGCCA CGGCTTCTGGTCTACCAGCTTC AGCTACTGGTACTTCGACCTGT GGGGCAGAGGCCACTTCGTGG CCGTGTCTTGG (SEQ ID NO. 45) |
| LN01 variant 38 Variable Light (V_L) (CDRL1, CDRL2 and CDRL3 underlined) | DIQMTQSPSSLSASVGDKVTI TCRAS<u>QSVTKYLN</u>WYQFKT GQAPRIL<u>IYGTYTLL</u>SGVSPR FSGAGWGSLYTLTITNIQPED FATYYC<u>QQAHSTPWT</u>FGQG | ACATCCAGATGACCCAGAGCCC CAGCAGCCTGTCTGCCAGCGTG GGCGACAAAGTGACCATCACCT GTCGGGCCAGCCAGAGCGTGA CCAAGTACCTGAACTGGTATCA |

TABLE 4-continued

| LN01 region | Amino Sequence | Exemplary Nucleotide Sequence |
| --- | --- | --- |
| | THVAAN (SEQ ID NO.: 14) | GTTTAAGACCGGCCAGGCCCCC AGAATCCTGATCTACGGCACCT ACACCCTGCTGAGCGGCGTGTC CCCTAGATTCTCTGGCGCCGGA TGGGGCAGCCTGTACACCCTGA CAATCACCAACATCCAGCCCGA GGACTTCGCCACCTACTACTGC CAGCAGGCCCACAGCACCCCTT GGACATTTGGCCAGGGAACACA CGTGGCCGCCAAC (SEQ ID NO. 46) |
| LN01 variant 41 Variable Heavy (V$_H$) (CDRH1, CDRH2 and CDRH3 underlined) | EVQLVESGPGLVQPWGTLSL TCRVS<u>GDSVSNFNYYWA</u>WI RQTPGRELQVIGT<u>IYYSGTTY YNPSLRN</u>RVTISLDKSVNVVS LRLGSVSAADTAQYYC<u>VRMP SHGFWSTSFSYWYFDL</u>WGR GHFVAVSW (SEQ ID NO.: 15) | GAGGTGCAGCTGGTGGAATCTG GACCTGGACTGGTGCAGCCTTG GGGCACTCTGTCTCTGACATGC CGGGTGAGCGGGGACAGCGTC TCCAACTTTAATTACTATTGGGC TTGGATCAGGCAGACACCAGGG CGCGAGCTGCAGGTCATCGGG ACTATCTACTATTCCGGAACCAC ATACTATAACCCCTCTCTGCGGA ATAGAGTGACCATTTCTCTGGAC AAGAGTGTCAACGTGGTCAGTC TGCGACTGGGATCTGTGAGTGC CGCTGATACCGCACAGTACTAT TGCGTGCGGATGCCCTCTCACG GCTTCTGGTCAACAAGCTTTTCC TACTGGTATTTCGATCTGTGGG GACGGGGCCATTTCGTGGCCGT CTCCTGG (SEQ ID NO. 47) |
| LN01 variant 41 Variable Light (V$_L$) (CDRL1, CDRL2 and CD RL3 underlined) | DIQMTQSPSSLSASVGDKVTI TCRAS<u>QSVTKYLN</u>WYQFKT GQAPRIL<u>IYGTYTLL</u>SGVSPR FSGAGSGSLYTLTITNIQPED FATYYC<u>QQAHSTPWT</u>FGQG THVAAN (SEQ ID NO.: 16) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO. 48) |
| LN01 variant 42 Variable Heavy (V$_H$) (CDRH1, CDRH2 and CDRH3 underlined) | EVQLVESGPGLVQPWGTLSL TCRVS<u>GDSVSNYNYYWA</u>WI RQTPGRELQVIGT<u>IYYSGTTY YNPSLRN</u>RVTISLDKSVNVVS LRLGSVSAADTAQYYC<u>VRMP SHGFWSTSFSYWYFDL</u>WGR GHFVAVSW (SEQ ID NO.: 17) | GAGGTGCAGCTGGTGGAATCTG GACCTGGACTGGTGCAGCCTTG GGGCACTCTGTCTCTGACATGC CGGGTGAGCGGGGACAGCGTC TCCAACTACAATTACTATTGGGC TTGGATCAGGCAGACACCAGGG CGCGAGCTGCAGGTCATCGGG ACTATCTACTATTCCGGAACCAC ATACTATAACCCCTCTCTGCGGA ATAGAGTGACCATTTCTCTGGAC AAGAGTGTCAACGTGGTCAGTC TGCGACTGGGATCTGTGAGTGC CGCTGATACCGCACAGTACTAT TGCGTGCGGATGCCCTCTCACG GCTTCTGGTCAACAAGCTTTTCC TACTGGTATTTCGATCTGTGGG GACGGGGCCATTTTGTGGCCGT CTCCTGG (SEQ ID NO. 49) |
| LN01 variant 42 Variable Light (V$_L$) (CDRL1, CDRL2 and CD RL3 underlined) | DIQMTQSPSSLSASVGDKVTI TCRAS<u>QSVTKYLN</u>WYQFKT GQAPRIL<u>IYGTYTLL</u>SGVSPR FSGAGSGSLYTLTITNIQPED FATYYC<u>QQAHSTPWT</u>FGQG THVAAN (SEQ ID NO.: 18) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC |

TABLE 4-continued

| LN01 region | Amino Sequence | Exemplary Nucleotide Sequence |
|---|---|---|
| | | AGGCTCACAGTACTCCCTGGAC CTTCGGCCAAGGAACCCACGTG GCGGCCAAC (SEQ ID NO. 50) |
| LN01 variant 48 Variable Heavy (V$_H$) (CDRH1, CDRH2 and CDRH3 underlined) | QLQLQESGPGLVKPSETLSL TCTVS<u>GDSVSNWNYYWAWI</u> RQTPGRELQVIGT<u>IYYSGTTY</u> YNPSLRNRVTISLDKSVNVVS LRLGSVSAADTAQYYC<u>VRMP SHGFWSTSFSYWYFDLWGR</u> GTLVTVSS (SEQ ID NO.: 19) | CAGCTGCAGCTGCAGGAGAGTG GACCTGGACTGGTGAAGCCTTC AGAAACACTGAGCGTGACTTGC ACCGTGTCCGGCGACTCTGTCA GTAACTGGAATTACTATTGGGCA TGGATTAGACAGACACCAGGAA GAGAGCTGCAGGTCATCGGGAC AATCTACTATAGTGGAACCACAT ACTATAACCCCTCACTGCGGAA TAGAGTGACCATTTCCCTGGAC AAATCTGTCAACGTGGTCTCTCT GCGACTGGGCTCAGTGAGCGC CGCTGATACTGCCCAGTACTATT GCGTGCGGATGCCCAGCCACG GCTTCTGGTCCACCTCTTTTAGT TACTGGTATTTCGATCTGTGGG GACGGGGCACACTGGTGACTGT CAGCTCC (SEQ ID NO. 51) |
| LN01 variant 48 Variable Light (V$_L$) (CDRL1, CDRL2 and CD RL3 underlined) | DIQMTQSPSSLSASVGDKVTI TCRAS<u>QSVTKYLNWYQFKT GQAPRILIYGTYTLL</u>SGVSPR FSGAGSGSLYTLTITNIQPED FATYYC<u>QQAHSTPWTFGQG THVAAN</u> (SEQ ID NO.: 20) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO. 52) |
| LN01 variant 49 Variable Heavy (V$_H$) (CDRH1, CDRH2 and CDRH3 underlined) | EVQLVESGPGLVQPWGTLSL TCRVS<u>GDSVSNWWYYWAWI</u> RQTPGRELQVIGT<u>IYYSGTTY</u> YNPSLRNRVTISLDKSVNVVS LRLGSVSAADTAQYYC<u>VRMP SHGFWSTSFSYWYFDLWGR</u> GHFVAVSW (SEQ ID NO.: 21) | GAGGTGCAGCTGGTGGAATCTG GACCTGGACTGGTGCAGCCTTG GGGCACTCTGTCTCTGACATGC CGGGTGAGCGGGGACAGCGTC TCCAACTGGTGGTACTATTGGG CTTGGATCAGGCAGACACCAGG GCGCGAGCTGCAGGTCATCGG GACTATCTACTATTCCGGAACCA CATACTATAACCCCTCTCTGCG GAATAGAGTGACCATTTCTCTG GACAAGAGTGTCAATGTGGTCA GTCTGCGACTGGGATCTGTGAG TGCCGCTGATACCGCACAGTAC TATTGCGTGCGGATGCCCTCTC ACGGCTTCTGGTCAACAAGCTT TTCCTACTGGTATTTCGATCTGT GGGGACGGGGCCATTTGTGG CCGTCTCCTGG (SEQ ID NO.: 53) |
| LN01 variant 49 Variable Light (V$_L$) (CDRL1, CDRL2 and CDRL3 underlined) | DIQMTQSPSSLSASVGDKVTI TCRAS<u>QSVTKYLNWYQFKT GQAPRILIYGTYTLL</u>SGVSPR FSGAGSGSLYTLTITNIQPED FATYYC<u>QQAHSTPWTFGQG THVAAN</u> (SEQ ID NO.: 22) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO. 54) |
| LN01 variant 82 Variable Heavy (V$_H$) (CDRH1, CDRH2 and CDRH3 | QVQLEESGPGLVQPWGTLS LTGRVS<u>GGSISSSSYYWAWI</u> RQTPGRELQVIGT<u>IYYSGTTY</u> YNPSLRNRVTISLDKSVNVVS | CAGGTGCAGCTGGAGGAATCTG GACCTGGACTGGTCCAGCCTTG GGGGACTCTGAGCCTGACCTGC CGGGTGTCAGGCGGGAGCATC |

TABLE 4-continued

| LN01 region | Amino Sequence | Exemplary Nucleotide Sequence |
|---|---|---|
| underlined) | LRLGSVSAADTAQYYC<u>VRMP SHGFWSTSFSYWYFDLWGR</u> GHFVAVSW (SEQ ID NO. 23) | AGCTCCTCTAGTTACTATTGGGC TTGGATTAGGCAGACACCAGGC CGCGAGCTGCAGGTCATCGGCA CTATCTACTATAGTGGGACCACA TACTATAACCCCTCACTGCGGA ATAGAGTGACCATCTCCCTGGA CAAGTCTGTCAACGTGGTCTCT CTGCGACTGGGATCAGTGAGCG CCGCTGATACCGCACAGTACTA TTGCGTGCGGATGCCCAGCCAC GGCTTCTGGTCCACATCTTTTAG TTACTGGTATTTCGACCTGTGG GGGCGGGGACATTTTGTGGCC GTCAGTTGG (SEQ ID NO.: 55) |
| LN01 variant 82 Variable Light ($V_L$) (CDRL1, CDRL2 and CDRL3 underlined) | DIQMTQSPSSLSASVGDKVTI TCRAS<u>QSVTKYLN</u>WYQFKT GQAPRI<u>LIYGTYTLL</u>SGVSPR FSGAGSGSLYTLTITNIQPED FATYYC<u>QQAHSTPW</u>TFGQG THVAAN (SEQ ID NO.: 24) | GACATCCAGATGACCCAGTCTC CGTCCTCCCTGTCTGCCTCTGT TGGAGACAAAGTCACCATCACC TGCCGGGCCAGTCAGAGTGTCA CCAAATATTTAAATTGGTATCAG TTTAAGACCGGCCAAGCCCCAA GAATCCTCATCTATGGGACTTAT ACTTTACTCAGTGGCGTCTCGC CTCGGTTCAGTGGCGCCGGATC TGGTTCACTCTACACTCTGACCA TCACCAATATACAGCCTGAAGA CTTCGCCACCTATTATTGTCAAC AGGCTCACAGTACTCCCTGGAC CTTCGGCCAAGGAACCCACGTG GCGGCCAAC (SEQ ID NO.: 56) |
| LN01 variants 7 and 48 Variable Heavy ($V_H$) CDRH1 | GDSVSN<u>W</u>NYY (SEQ ID NO.: 25) | GGCGACAGCGTGTCCAACTGGA ACTACTAC (SEQ ID NO. 57) |
| LN01 variant 8 Variable Heavy ($V_H$) CDRH1 | GDSVSN<u>D</u>WYY (SEQ ID NO.: 26) | GGCGACAGCGTGTCCAACGACT GGTACTAC (SEQ ID NO. 58) |
| LN01 variant 41 Variable Heavy ($V_H$) CDRH1 | GDSVSN<u>F</u>NYY (SEQ ID NO.: 27) | GGGGACAGCGTCTCCAACTTTA ATTACTAT (SEQ ID NO. 59) |
| LN01 variant 42 Variable Heavy ($V_H$) CDRH1 | GDSVSN<u>Y</u>NYY (SEQ ID NO.: 28) | GGGGACAGCGTCTCCAACTACA ATTACTAT (SEQ ID NO. 60) |
| LN01 variant 43 Variable Heavy ($V_H$) CDRH1 | GDSVSN<u>L</u>NYY (SEQ ID NO.: 29) | GGGGACAGCGTCTCCAACTTAA ATTACTAT (SEQ ID NO. 61) |
| LN01 variant 44 Variable Heavy ($V_H$) CDRH1 | GDSVSN<u>I</u>NYY (SEQ ID NO.: 30) | GGGGACAGCGTCTCCAACATTA ATTACTAT (SEQ ID NO. 62) |
| LN01 variant 49 Variable Heavy ($V_H$) CDRH1 | GDSVSN<u>WW</u>YY (SEQ ID NO.: 31) | GGGGACAGCGTCTCCAACTGGT GGTACTAT (SEQ ID NO. 63) |
| LN01 variant 82 Variable Heavy ($V_H$) CDRH1 (germline sequence) | GSISSSSYY (SEQ ID NO.: 32) | GGGAGCATCAGCTCCTCTAGTT ACTAT (SEQ ID NO. 64) |

Thus, a nucleic acid encoding a binding agent of this disclosure may comprise one or more SEQ ID NOS. 33-64 or GGGACTTAT, or a derivative thereof that encodes any of SEQ ID NOS. 1-32 or GTY (LN01 CDRL2) and/or a derivative thereof (e.g., any of SEQ ID NOS. 1-32 conservatively substituted as described in Table 2, encoded by a nucleotide sequence determined using standard techniques, e.g., as described in Table 3, including but not limited to those described in Table 4). Expression vectors comprising such nucleic acid sequences are also contemplated by this disclosure. Where the binding agents are antibodies, nucleotide sequences encoding the variable regions thereof may also be isolated from the phage and/or hybridoma cells expressing the same cloned into expression vectors. Methods for producing such preparations are well-known in the art.

Nucleic acid molecules encoding one or more HIV binding agents may be contained within a viral and/or a non-viral vector. In one embodiment, a DNA vector is utilized to deliver nucleic acids encoding one or more HIV binding agents to the patient. In doing so, various strategies may be utilized to improve the efficiency of such mechanisms including, for example, the use of self-replicating viral replicons (Caley, et al. 1999. Vaccine, 17: 3124-2135; Dubensky, et al. 2000. *Mol. Med.* 6: 723-732; Leitner, et al. 2000. *Cancer Res.* 60: 51-55), codon optimization (Liu, et al. 2000. *Mol. Ther.*, 1: 497-500; Dubensky, supra; Huang, et al. 2001. *J. Virol.* 75: 4947-4951), in vivo electroporation (Widera, et al. 2000. *J. Immunol.* 164: 4635-3640), incorporation of nucleic acids encoding co-stimulatory molecules, cytokines and/or chemokines (Xiang, et al. 1995. *Immunity*, 2: 129-135; Kim, et al. 1998. *Eur. J. Immunol.*, 28: 1089-1103; Iwasaki, et al. 1997. *J. Immunol.* 158: 4591-3201; Sheerlinck, et al. 2001. *Vaccine*, 19: 2647-2656), incorporation of stimulatory motifs such as CpG (Gurunathan, supra; Leitner, supra), sequences for targeting of the endocytic or ubiquitin-processing pathways (Thomson, et al. 1998. *J. Virol.* 72: 2246-2252; Velders, et al. 2001. *J. Immunol.* 166: 5366-5373), prime-boost regimens (Gurunathan, supra; Sullivan, et al. 2000. *Nature*, 408: 605-609; Hanke, et al. 1998. *Vaccine*, 16: 439-445; Amara, et al. 2001. *Science*, 292: 69-74), proteasome-sensitive cleavage sites, and the use of mucosal delivery vectors such as *Salmonella* (Darji, et al. 1997. *Cell*, 91: 765-775; Woo, et al. 2001. *Vaccine*, 19: 2945-2954). Other methods are known in the art, some of which are described below. Various viral vectors that have been successfully utilized for introducing a nucleic acid to a host include retrovirus, adenovirus, adeno-associated virus (AAV), herpes virus, and poxvirus, among others. The vectors may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.). "Non-viral" plasmid vectors may also be suitable in certain embodiments. Preferred plasmid vectors are compatible with bacterial, insect, and/or mammalian host cells. Such vectors include, for example, PCR-ii, PCR3, and pcDNA3.1 (Invitrogen, San Diego, Calif.), pBSii (Stratagene, La Jolla, Calif.), pet15 (Novagen, Madison, Wis.), pGEX (Pharmacia Biotech, Piscataway, N.J.), pEGFp-n2 (Clontech, Palo Alto, Calif.), pETI (Bluebacii, Invitrogen), pDSR-alpha (PCT pub. No. WO 90/14363) and pFASTBACdual (Gibco-BRL, Grand island, N.Y.) as well as Bluescript® plasmid derivatives (a high copy number COLe1-based phagemid, Stratagene Cloning Systems, La Jolla, Calif.), PCR cloning plasmids designed for cloning TAQ-amplified PCR products (e.g., TOPO™ TA Cloning® kit, PCR2.1® plasmid derivatives, Invitrogen, Carlsbad, Calif.). Bacterial vectors may also be used. These vectors include, for example, *Shigella, Salmonella, Vibrio cholerae, Lactobacillus*, Bacille Calmette Guérin (BCG), and *Streptococcus* (see for example, WO 88/6626; WO 90/0594; WO 91/13157; WO 92/1796; and WO 92/21376). Many other non-viral plasmid expression vectors and systems are known in the art and may be use. Other delivery techniques may also suffice including, for example, DNA-ligand complexes, adenovirus-ligand-DNA complexes, direct injection of DNA, CaPO$_4$ precipitation, gene gun techniques, electroporation, and colloidal dispersion systems. Colloidal dispersion systems include macromolecule complexes, nanocapsules, microspheres, beads, and lipid-based systems including oil-in-water emulsions, micelles, mixed micelles, and liposomes. The preferred colloidal system is a liposome, which are artificial membrane vesicles useful as delivery vehicles in vitro and in vivo. RNA, DNA and intact virions can be encapsulated within the aqueous interior and be delivered to cells in a biologically active form (Fraley, R., et al., 1981, *Trends Biochem. Sci.*, 6: 77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

A cultured cell comprising the vector is also provided. The cultured cell may be a cultured cell transfected with the vector or a progeny of the cell, wherein the cell expresses the immunogenic polypeptide. Suitable cell lines are known to those of skill in the art and are commercially available, for example, through the American Type Culture Collection (ATCC). The transfected cells can be used in a method of producing an immunogenic polypeptide. The method comprises culturing a cell comprising the vector under conditions that allow expression of the immunogenic polypeptide, optionally under the control of an expression sequence. The immunogenic polypeptide can be isolated from the cell or the culture medium using standard protein purification methods. In some embodiments, the binding agents described herein may be conjugated to active agents to target and inhibit the function of and/or eliminate cell populations expressing HIV polypeptides and/or harboring HIV (and/or another antigen in the case of binding agents with multiple specificities). For instance, CD4$^+$ T-cell populations containing replication competent HIV may be targeted and eliminated using binding agent/drug conjugates (e.g., antibody-drug conjugates (ADC)). Mono- and/or bi-specific candidate binding agents may be conjugated with one or more types of drugs (e.g., drugs damaging DNA, targeting microtubules). The binding agents described herein and/or derivatives thereof may also be adjoined to and/or conjugated to functional agents for in vitro and/or in vivo use. For instance, the binding agent may be adjoined to and/or conjugated to functional moieties such as cytotoxic drugs or toxins, and/or active fragments thereof such as diphtheria A chain, exotoxin A chain, ricin A chain, abrin A chain, curcin, crotin, phenomycin, enomycin, among others. Suitable functional moieties may also include radiochemicals. Binding agents, such as antibodies, may be adjoined to and/or conjugated to the one or more functional agents using standard techniques in the art.

In some embodiments, this disclosure provides binding agents with multiple specificities such that epitopes bound by LN01 (e.g., ITKWLWYIK (SEQ ID NO. 72) but not LASWVKYIQ (SEQ ID NO. 71) and/or ITKWIKYIQ (SEQ ID NO. 73)) and at least one other secondary antigen (e.g., a cell surface protein) may be bound by a single binding agent. In some embodiments, the secondary antigen may be one expressed by cells infected by an infectious agent. For instance, an exemplary secondary antigen may be HIV Env antigen other than gp41. Such binding agents may bind the secondary antigen and/or may serve to neutralize the infectious agent as may be determined using the assays described herein. Combinations of binding agents, such as one or more described herein with another available to those of ordinary skill in the art, are also contemplated herein. For instance, in some embodiments, the combinations may be identified to provide statistically significant differences from results (e.g., neutralization assays) obtained using only one or more of the binding agents and not others. In some embodiments, combinations exhibit synergistic neutralization of HIV, for example. In some embodiments, the combination may comprise a first binding agent having the characteristics of LN01 (e.g., such as IgG1 LN01) and/or comprising any one or more of SEQ ID NOS. 1-32 (and/or as described in Table 1), and/or derivatives thereof, and any one or more of the antibodies described in any one or more of U.S. Pat. Nos. 5,087,557; 5,298,419; 5,459,060; 5,693,752; 5,731,189; 5,753,503; 5,756,674; 5,777,074; 5,804,440; 5,831,034; 6,008,044; 7,774,887B2; U.S. Pat. Publications 2003/0118985A1, 2007/0292390A1, or 2014/0205612A1; WO 2002/032452A1 (e.g., binding the gp41 epitopes ELDKWA, ELEKWA, ELNKWA, ELDEWA); EP0335134B1 U.S. Pat. No. 176,077 (e.g., a humanized version of the mouse mAbs described therein); DE3932461A1 (mAb against the epitope Arg-Ile-Leu-Ala-Val-Glu-Arg-Leu-Lys-Try-Asp-Gln-Gln-Leu-Leu-Gly-Ile-Trp-Gly-Cys-Ser); Evans, et al. J. Immunol. 140(3): 941-3 (1988); Gorney, et al. Proc. Natl. Acad. Sci. USA, 86: 1624-28 (1989); Teeuwsen, et al. (1990) *AIDS Res. Hum. Retroviruses* 6, 381-392; Earl, et al. J. Virol. 71(4): 2674-2684 (1997); Jiang, et al. J. Virol. 72(12): 10213-17 (1998); Zwick, et al. J. Virol. 75(22): 10892-10905 (2001); Eckert et al. PNAS USA, 98(20): 11187-11192 (2001); Louis, et al. J. Biol. Chem. 278(22): 20278-20285 (2003); and/or Pietzsch, et al. J. Virol. 84(10): 5032-42 (2010); all of which are incorporated herein in their entirety. For instance, any of the binding agents described herein may be combined with (i.e., as a single composition, and/or used in conjunction with) one or more the antibodies commonly known as 2F5, 4E10 and/or Z13e1, and/or derivatives thereof, among others. The binding agents of such compositions may be different entities such as two or more different monoclonal antibodies or derivatives thereof, or may be found on the same entity such as a bi-functional antibody (a single antibody or derivative thereof comprising multiple binding specificities). Such combinations as described herein may also be combined with one or more other agents that may effect immune cell function such as antibodies against CTLA-4, and the like. One of ordinary skill in the art would recognize that many such combinations may be suitable for use as descrbed herein.

As mentioned above, the HIV binding agents described herein may be used to treat and/or prevent and/or ameliorate the symptoms of infection by HIV. As is well-known in the art, HIV isolates are now classified into discrete genetic subtypes. HIV-1 is known to comprise at least ten subtypes (A1, A2, A3, A4, B, C, D, E, F1, F2, G, H, J and K) (Taylor et al, NEJM, 359(18):1965-1966 (2008)). HIV-2 is known to include at least five subtypes (A, B, C, D, and E). Subtype B has been associated with the HIV epidemic in homosexual men and intravenous drug users worldwide. Most HIV-1 immunogens, laboratory adapted isolates, reagents and mapped epitopes belong to subtype B. In sub-Saharan Africa, India and China, areas where the incidence of new HIV infections is high, HIV-1 subtype B accounts for only a small minority of infections, and subtype HIV-1 C appears to be the most common infecting subtype. Any of these types of isolates may be addressed using the binding agents described herein. One or more binding agents may also be administered with or in conjunction with one or more agents used to prevent, treat and/or ameliorate HIV such as for example, a protease inhibitor, an HIV entry inhibitor, a reverse transcriptase inhibitor, and/or an anti-retroviral nucleoside analog. Suitable compounds include, for example, Agenerase (amprenavir), Combivir (Retrovir/Epivir), Crixivan (indinavir), Emtriva (emtricitabine), Epivir (3tc/lamivudine), Epzicom, Fortovase/Invirase (saquinavir), Fuzeon (enfuvirtide), Hivid (ddc/zalcitabine), Kaletra (lopinavir), Lexiva (Fosamprenavir), Norvir (ritonavir), Rescriptor (delavirdine), Retrovir/AZT (zidovudine), Reyatax (atazanavir, BMS-232632), Sustiva (efavirenz), Trizivir (abacavir/zidovudine/lamivudine), Truvada (Emtricitabine/Tenofovir DF), Videx (ddI/didanosine), Videx EC (ddI, didanosine), Viracept (nevirapine), Viread (tenofovir disoproxil fumarate), Zerit (d4T/stavudine), and Ziagen (abacavir) may be utilized. Other suitable agents are known to those of skill in the art and may be suitable for use as described herein. Such agents may either be used prior to, during, or after administration of the binding agents and/or use of the methods described herein.

The skilled artisan has many suitable techniques for using the binding agents (e.g., antibodies) described herein to identify biological samples containing proteins that bind thereto. For instance, antibodies may be utilized to isolate HIV or cells containing HIV and/or expressing HIV antigens using, for example, immunoprecipitation or other capture-type assay. This well-known technique is performed by attaching the antibody to a solid support or chromatographic material (e.g., a bead coated with Protein A, Protein G and/or Protein L). The bound antibody is then introduced into a solution either containing or believed to contain HIV antigens (e.g., an HIV-infected cell). The HIV antigen(s) may then bind to the antibody and non-binding materials are washed away under conditions in which the HIV antigen(s) remains bound to the antibody. The bound protein may then be separated from the antibody and analyzed as desired. Similar methods for isolating a protein using an antibody are well-known in the art. The binding agents (e.g., antibodies) may also be utilized to detect HIV or HIV antigens within a biological sample. For instance, the antibodies may be used in assays such as, for example, flow cytometric analysis, ELISA, immunoblotting (e.g., western blot), in situ detection, immunocytochemistry, and/or immunhistochemistry. Methods of carrying out such assays are well-known in the art. In some embodiments, the binding agents may be adjoined to and/or conjugated to one or more detectable labels. For instance, suitable detectable labels may include, for instance, fluorosceins (e.g., DyLight, Cy3, Cy5, FITC, HiLyte Fluor 555, HiLyte Fluor 647; 5-carboxy-2,7-dichlorofluorescein; 5-Carboxyfluorescein (5-FAM); 5-HAT (Hydroxy Tryptamine); 5-Hydroxy Tryptamine (HAT); 6-JOE; 6-carboxyfluorescein (6-FAM); FITC; 6-carboxy-1,4-dichloro-2',7'-dichlorofluorescein (TET); 6-carboxy-1,4-dichloro-2',4',5',7'-tetrachlorofluorescein (HEX); 6-carboxy-4',5'-dichloro-2',7'-dimethoxyfluorescein (JOE); Alexa fluors (e.g., 350, 405, 430, 488, 500, 514, 532, 546, 555, 568, 594, 610, 633, 635, 647, 660, 680, 700, 750); BODIPY fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE)), rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2, ROX (6-carboxy-X-rhodamine), 5-ROX (carboxy-X-rhodamine), Sulphorhodamine B can C, Sulphorhodamine G Extra, TAMRA (6-carboxytetramethyirhodamine), Tetramethylrhodamine (TRITC), WT), Texas Red, and/or Texas Red-X. Other detectable labels known in the art may also be suitable for use. Binding agents, such as antibodies, may be adjoined to and/or conjugated to the one or more detectable labels using standard techniques in the art.

The binding agents described herein may be also be used to determine the presence of a disease state in a patient, to predict prognosis, or to determine the effectiveness of a chemotherapeutic or other treatment regimen. Expression profile assays, performed as described herein or as is otherwise known in the art, may be used to determine the relative level of expression of HIV in a cell, for instance. The level of expression may then be correlated with base (e.g., control) levels to determine whether a particular disease is present within the patient, the patient's prognosis, or whether a particular treatment regimen is effective. For example, if the patient is being treated with a particular anti-infective regimen, an increased or decreased level of expression of HIV in the patient's tissues (e.g., in plasma) may indicate the regimen is worsening or improving the load of HIV in that host. The increase or decrease in expression may indicate the regimen is having or not having the desired effect and another therapeutic modality may therefore be selected.

It is also possible to use the binding agents described herein as reagents in drug screening assays to test, for example, new drug candidates. The reagents may be used to ascertain the effect of a drug candidate on the expression of the immunogenic target in a cell line, or a cell or tissue of a patient. The expression profiling technique may be combined with high throughput screening techniques to allow rapid identification of useful compounds and monitor the effectiveness of treatment with a drug candidate (see, for example, Zlokamik, et al., Science 279, 84-8 (1998)). Drug candidates may be chemical compounds, nucleic acids, proteins, antibodies, or derivatives therefrom, whether naturally occurring or synthetically derived. Drug candidates thus identified may be utilized, among other uses, as pharmaceutical compositions for administration to patients or for use in further screening assays.

In some embodiments, the binding agents are in purified form. A "purified" binding agent (e.g., antibody) may be one that is separated from at least about 50% of the proteins and/or other components with which it is initially found (e.g., as part of a hybridoma supernatant or ascites preparation in the case of a monoclonal antibody). A purified binding agent (e.g., antibody) may be one that is separated from at least about 50%, 60%, 75%, 90%, or 95% of the proteins and/or other components with which it is initially found.

The polypeptides and nucleic acids described herein may also be combined with one or more pharmaceutically acceptable carriers prior to administration to a host. A pharmaceutically acceptable carrier is a material that is not biologically or otherwise undesirable, e.g., the material may be administered to a subject, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. Suitable pharmaceutical carriers and their formulations are described in, for example, *Remington's: The Science and Practice of Pharmacy,* 21st *Edition,* David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally from about 5 to about 8 or from about 7 to about 7.5. Other carriers include sustained-release preparations such as semipermeable matrices of solid hydrophobic polymers containing polypeptides or fragments thereof. Matrices may be in the form of shaped articles, e.g., films, liposomes or microparticles. It will be apparent to those persons skilled in the art that certain carriers may be more preferable depending upon, for instance, the route of administration and concentration of composition being administered. Carriers are those suitable for administration of polypeptides and/or fragments thereof to humans or other subjects. Pharmaceutical compositions may also include carriers, thickeners, diluents, buffers, preservatives, surface active agents, adjuvants, immunostimulants, in addition to the immunogenic polypeptide. Pharmaceutical compositions may also include one or more active ingredients such as antimicrobial agents, antiinflammatory agents and anesthetics. The pharmaceutical composition may be administered orally, parentally, by inhalation spray, rectally, intranodally, or topically in dosage unit formulations containing conventional pharmaceutically acceptable carriers, adjuvants, and vehicles. The term "pharmaceutically acceptable carrier" or "physiologically acceptable carrier" as used herein refers to one or more formulation materials suitable for accomplishing or enhancing the delivery of a nucleic acid, polypeptide, or peptide as a pharmaceutical composition. A "pharmaceutical composition" is a composition comprising a therapeutically effective amount of a nucleic acid or polypeptide. The terms "effective amount" and "therapeutically effective amount" each refer to the amount of a binding agent, nucleic acid or the like used to observe the desired therapeutic effect (e.g., eliminating HIV).

Methods for treating one or more disease conditions (e.g., HIV or cancer) in a mammalian host comprising administering to the mammal at least one or more effective doses of one or more binding agents (and/or derivative(s) thereof) described herein are also provided. In some embodiments, the binding agent is a monoclonal antibody or fragment or derivative thereof comprising one or more of SEQ ID NOS. 1-32 and/or shown in Table 1. The one or more binding agents may be administered in a dosage amount of about 1 to about 50 mg/kg, about 1 to about 30 mg/kg, or about 5 to about 30 mg/kg (e.g., about any of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, or 40 mg/kg). In certain embodiments, the one or more binding agents may be administered to the mammal (e.g., intradermally, intravenously, orally, rectally) at about 10 mg/kg one or more times. When multiple doses are administered, the doses may comprise about the same or different amount of binding agent in each dose. The doses may also be separated in time from one another by the same or different intervals. For instance, the doses may be separated by about any of 6, 12, 24, 36, 48, 60, 72, 84, or 96 hours, one week, two weeks, three weeks, one month, two months, three months, four months, five months, six months, seven months, eight months, nine months, 10 months, 11 months, 12 months, 1.5 years, 2 years, 3 years, 4 years, 5 years, or any time period before, after, and/or between any of these time periods. In some embodiments, the binding agents may be administered in conjunction with other agents (e.g., anti-infective agents and/or chemotherapeutic agent).

Such other agents may be administered about simultaneously with the binding agents, or at a different time and/or frequency. Other embodiments of such methods may also be appropriate as could be readily determined by one of ordinary skill in the art.

To assist the skilled artisan in using the binding agents such as antibodies described herein, the same may be provided in kit format. A kit including one or more of such binding agents and optionally other components necessary for using the same to detect cells expressing HIV is also provided. The binding agents of the kit may be provided in any suitable form, including frozen, lyophilized, or in a pharmaceutically acceptable buffer such as TBS or PBS. The kit may also include other reagents required for utilization of the binding agents in vitro or in vivo such as buffers (e.g., TBS, PBS), blocking agents (solutions including nonfat dry milk, normal sera, Tween-20 Detergent, BSA, or casein), and/or detection reagents (e.g., goat anti-mouse IgG biotin, streptavidin-HRP conjugates, allophycocyanin, B-phycoerythrin, R-phycoerythrin, peroxidase, detectable labels, and other labels and/or staining kits (e.g., ABC Staining Kit, Pierce)). The kits may also include other reagents and/or instructions for using the antibodies in commonly utilized assays described above such as, for example, flow cytometric analysis, ELISA, immunoblotting (e.g., western blot), in situ detection, immunocytochemistry, immunhistochemistry. In one embodiment, the kit provides a binding agent in purified form. In another embodiment, the binding agent may be provided in biotinylated form either alone or along with an avidin-conjugated detection reagent (e.g., antibody). In another embodiment, the kit includes a binding agents comprising one or more detectable labels that may be used to directly detect HIV. Buffers and the like required for using any of these systems are well-known in the art and/or may be prepared by the end-user or provided as a component of the kit. The kit may also include a solid support containing positive- and negative-control protein and/or tissue samples. For example, kits for performing spotting or western blot-type assays may include control cell or tissue lysates for use in SDS-PAGE or nylon or other membranes containing pre-fixed control samples with additional space for experimental samples. Kits for visualization of HIV in cells on slides may include pre-formatted slides containing control cell or tissue samples with additional space for experimental samples. Other embodiments of kits are also contemplated herein as would be understood by those of ordinary skill in the art.

Thus, this disclosure provides binding agents such as the LN01 antibody with specificity for HIV. In some embodiments, the binding agent is a polypeptide comprising at least one amino acid sequence selected from the group consisting of SEQ ID NOS. 1-32 and/or shown in Table 1. In some embodiments, the binding agent is a polypeptide comprising one or more combinations of SEQ ID NOS. 1-32. In some embodiments, the binding agent is an antibody. In some embodiments, the binding agent is a polypeptide such as an antibody comprising a heavy chain CDR amino acid sequence selected from the group consisting of SEQ ID NOS. 1-3. In some embodiments, the binding agent is a polypeptide such as an antibody comprising a light chain CDR amino acid sequence selected from the group consisting of SEQ ID NOS. 4-7. In some embodiments, the binding agent is a polypeptide such as an antibody comprising a $V_H$ amino acid sequence of SEQ ID NO. 7 (LN01), SEQ ID NO. 9 (LN01 variant 7), SEQ ID NO. 11 (LN01 variant 8), SEQ ID NO. 13 (LN01 variant 38), SEQ ID NO. 15 (LN01 variant 41), SEQ ID NO. 17 (LN01 variant 42), SEQ ID NO. 19 (LN01 variant 48), SEQ ID NO. 21 (LN01 variant 49), or SEQ ID NO. 23 (LN01 variant 82). In some embodiments, the binding agent is a polypeptide such as an antibody comprising a $V_L$ amino acid sequence of SEQ ID NO. 8 (LN01), SEQ ID NO. 10 (LN01 variant 7), SEQ ID NO. 12 (LN01 variant 8), SEQ ID NO. 14 (LN01 variant 38), SEQ ID NO. 16 (LN01 variant 41), SEQ ID NO. 18 (LN01 variant 42), SEQ ID NO. 20 (LN01 variant 48), SEQ ID NO. 22 (LN01 variant 49), or SEQ ID NO. 28 (LN01 variant 24). In some embodiments, the binding agent comprises the combinations of CDRs (SEQ ID NOS. 1-6 or GNT (LN01 CDRL1)) and/or variable regions (SEQ ID NOS. 7 and 8; SEQ NOS. 9 and 10; SEQ NOS. 11 and 12; SEQ NOS. 13 and 14; SEQ NOS. 15 and 16; SEQ NOS. 17 and 18; SEQ NOS. 19 and 20; SEQ NOS. 21 and 22; or, SEQ ID NOS. 23 and 24; or a conservatively substituted variant thereof) shown in Table 1.

In some embodiments, the binding agents have specificity for an epitope comprising amino acid residues L679, W680 and K683 of SEQ ID NO. 68 and/or amino acid residues L168, W169 and K172 of SEQ ID NO. 69. In some embodiments, the binding agent exhibits the capacity to bind to and/or neutralize HIV expressing amino acid sequence ITKWLWYIK (SEQ ID NO. 66). In some embodiments, the binding agent exhibits the capacity to bind to and/or neutralize HIV expressing amino acid sequence ITKWLWYIK (SEQ ID NO. 66) but not LASWVKYIQ (SEQ ID NO. 65) and/or ITKWIKYIQ (SEQ ID NO. 67). In some embodiments, a binding agent of this disclosure may comprise any one or more of these binding specificities along with the neutralization characteristics described above (i.e., neutralization of HIV-1 pseudoviruses BJOX (CRF07_BC), CE1176, TRO.11 (B), X1632 (G), CH119 (CRF07_BC), CNE55 (CRF01_AE), 25710 (C), CD0217(C) but not of the control virus SVA-MLV at a concentration is from $10^2$-$10^0$ ug/ml, or between $10^0$-$10^1$ ug/ml, to at least about 50%, and/or the ability to the neutralize a majority of the 118 HIV-1 pseudoviruses listed in FIG. 4 at an $IC_{50}$ of less than 25). In some embodiments, nucleic acids encoding such binding agents are also provided as in Table 4.

In some embodiments, the binding agent is derived from or related to (e.g., by sequence or derivation) a human antibody, human IgG, human IgG1, human IgG2, human IgG2a, human IgG2b, human IgG3, human IgG4, human IgM, human IgA, human IgA1, human IgA2, human IgD, human IgE, canine antibody, canine IgGA, canine IgGB, canine IgGC, canine IgGD, chicken antibody, chicken IgA, chicken IgD, chicken IgE, chicken IgG, chicken IgM, chicken IgY, goat antibody, goat IgG, mouse antibody, mouse IgG, pig antibody, and/or rat antibody, and/or a derivative thereof. In some embodiments, the derivative may be selected from the group consisting of an $F_{ab}$, $F_{ab2}$, Fab' single chain antibody, $F_v$, single chain, mono-specific antibody, bispecific antibody, trimeric antibody, multi-specific antibody, multivalent antibody, chimeric antibody, canine-human chimeric antibody, canine-mouse chimeric antibody, antibody comprising a canine Fc, humanized antibody, human antibody, caninized antibody, CDR-grafted antibody, shark antibody, nanobody, and/or canelid antibody. In some embodiments, the binding agent comprises at least a least a first and second specificity, the first being against HIV gp41 and the second being against a different antigen (e.g., an antigen of an infectious agent such as HIV (e.g., env) and/or a tumor antigen). In some embodiments, the binding agent and/or derivative thereof may comprise a detectable label fixably attached thereto. In some embodiments, the binding agent of any one and/or derivative thereof comprises an effector moiety (e.g., a cytotoxic drug, toxin, diphtheria A chain, exotoxin A chain, ricin A chain, abrin A chain, curcin, crotin, phenomycin, enomycin, and radiochemical) fixably attached thereto. In some embodiments, polynucleotides encoding one or more binding agents are also provided (e.g., as an expression vector). Host cells comprising and/or expressing the polypeptide products of such polynucleotides are also provided. In some embodiments, compositions comprising at least one binding agent or derivative; at least one isolated polynucleotide; at least one expression vector; and/or, at least one host cell; or a combination thereof; and, a pharmaceutically acceptable carrier are also provided.

This disclosure also provides methods for detecting HIV on a cell, the method comprising contacting a test biological sample with a binding agent or derivative described herein and detecting the binding agent bound to the biological sample or components thereof. Such methods may be an in vivo method or an in vitro method. In some embodiments, the method may comprise comparing the amount of binding to the test biological sample or components thereof to the amount of binding to a control biological sample or components thereof, wherein increased binding to the test biological sample or components thereof relative to the control biological sample or components thereof indicates the presence of a cell expressing HIV polypeptides in the test biological sample (e.g., mammalian blood). In some embodiments, a kit for detecting the expression of HIV in or on a cell, the kit comprising a binding agent or derivative thereof and instructions for use. In some embodiments, the binding agent and/or derivative thereof is in lyophilized form. In some embodiments, this disclosure provides methods for treating, preventing and/or ameliorating an infectious disease, cancer and/or autoimmunity in a mammal comprising administering to the mammal at least one effective dose of a pharmaceutical composition comprising a binding agent or derivative thereof. In some embodiments, the infectious disease is human immunodeficiency virus (HIV). In some embodiments, multiple doses are administered to the animal. In some embodiments, the binding agent and/or derivative thereof may be administered in a dosage amount of about 1 to 50 mg/kg.

The terms "about", "approximately", and the like, when preceding a list of numerical values or range, refer to each individual value in the list or range independently as if each individual value in the list or range was immediately preceded by that term. The terms mean that the values to which the same refer are exactly, close to, or similar thereto.

As used herein, a subject or a host is meant to be an individual. The subject can include domesticated animals, such as cats and dogs, livestock (e.g., cattle, horses, pigs, sheep, and goats), laboratory animals (e.g., mice, rabbits, rats, guinea pigs) and birds. In one aspect, the subject is a mammal such as a primate or a human.

Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination).

Ranges may be expressed herein as from about one particular value, and/or to about another particular value. When such a range is expressed, another aspect includes from the one particular value and/or to the other particular value. Similarly, when values are expressed as approximations, by use of the antecedent about or approximately, it will be understood that the particular value forms another aspect. It will be further understood that the endpoints of each of the ranges are significant both in relation to the other endpoint, and independently of the other endpoint. Ranges (e.g., 90-100%) are meant to include the range per se as well as each independent value within the range as if each value was individually listed.

The term "combined" or "in combination" or "in conjunction" may refer to a physical combination of agents that are administered together or the use of two or more agents in a regimen (e.g., administered separately, physically and/or in time) for treating, preventing and/or ameliorating a particular disease.

When the terms treat, prevent, and/or ameliorate or derivatives thereof are used herein in connection with a given treatment for a given condition (e.g., preventing cancer infection by HIV), it is meant to convey that the treated patient either does not develop a clinically observable level of the condition at all, or develops it more slowly and/or to a lesser degree than he/she would have absent the treatment. These terms are not limited solely to a situation in which the patient experiences no aspect of the condition whatsoever. For example, a treatment will be said to have prevented the condition if it is given during exposure of a patient to a stimulus that would have been expected to produce a given manifestation of the condition, and results in the patient's experiencing fewer and/or milder symptoms of the condition than otherwise expected. For instance, a treatment can "prevent" infection by resulting in the patient's displaying only mild overt symptoms of the infection; it does not imply that there must have been no penetration of any cell by the infecting microorganism.

Similarly, reduce, reducing, and reduction as used herein in connection with prevention, treatment and/or amelioration of a given condition by a particular treatment typically refers to a subject developing an infection more slowly or to a lesser degree as compared to a control or basal level of developing an infection in the absence of a treatment (e.g., administration of one or more HIV binding agents). A reduction in the risk of infection may result in the patient's displaying only mild overt symptoms of the infection or delayed symptoms of infection; it does not imply that there must have been no penetration of any cell by the infecting microorganism.

All references cited within this disclosure are hereby incorporated by reference in their entirety. Certain embodiments are further described in the following examples. These embodiments are provided as examples only and are not intended to limit the scope of the claims in any way.

EXAMPLES

Example 1

Lymph Node Donors

Selection of HIV-1 lymph node donors for the Isolation of broadly neutralizing antibodies. In order to isolate broadly neutralizing antibodies capable to broadly neutralize multi-clade HIV-1 isolates 70 plasma samples from chronically infected patients naïve to antiretroviral therapy were screened for the presence of high titers of antibodies able to neutralize a panel of nine (9) HIV-1 pseudoviruses from the Global Panel of HIV-1 reference strains (DeCamp, A. et al. Global panel of HIV-1 Env reference strains for standardized assessments of vaccine-elicited neutralizing antibodies. J Virol 88, 2489-2507 (2014)). This analysis resulted in the identificiation of seven (7) patients (FIG. 1) as lymph node donors for the subsequent isolation and characterization of potent broadly neutralizing antibodies. In particular, donor SA003 was selected for the presence high level of antibodies found to neutralize eight (8) out of nine (9) isolates tested (and for the lack of background activity against the negative control MLV pseudovirus). Of note, SA003 donor is an Elite Controller with viremia <50 HIV RNA copies per ml of plasma (infected with clade B HIV-1).

Example 2

Isolation and Characterization of a Potent HIV-1 Broadly Neutralizing Antibody

Germinal center and Memory IgG B cells from donor SA003 were sorted separately according to IgG (i.e. IgA and IgM negative cells), CD19 and CD38 expression (germinal center B cells are CD38 positive) (FIG. 2) and interrogated for the production of HIV-1 neutralizing antibodies. In particular, highly pure IgG memory B cells and IgG germinal cells were seeded in separate plates as single cell micro-cultures on human feeder cells in the presence of Epstein-Barr Virus (EBV) (which also stimulate polyclonally memory B cells) and a cocktail composed TLR9 agonist CpG-2006, IL-2 (1000 IU/ml), IL-6 (10 ng/ml), IL-21 (10 ng/ml), and anti-BCR goat antibodies (BCR triggerring). Supernatants from day 14 cultures were then tested in a primary screening using a 384-well based HIV-1 pseudoviruses neutralization assay (using in parallel two strains, CE1176 and BJOX2000, representative of clade C and CRF07). Neutralization assays were undertaken on TZM-bl cells. In a 384-well plate, HIV-1 pseudoviruses that resulted in an output of $50\text{-}100 \times 10^4$ relative light units (RLU) were incubated with B cell culture supernatants for 1 h at 37% (5% $CO_2$) before the addition of 3000 TZM-bl cells. These were incubated for a further 72 h, after which supernatant was removed and 15 µl Steadylite reagent (Perkin Elmer) was added. Luciferase activity was detected 5 min later by reading the plates on a Synergy microplate luminometer (BioTek). The supernatants derived from two cultures of germinal center B cells were found able to cross-neutralize both CE1176 and BJOX2000 strains. The supernatants from these two cultures were further harvested and tested for their ability to neutralize four (4) pseudoviruses (CE1176, BJOX2000, X1632 and 25710). Of note, one of the two supernatants neutralized all four pseudoviruses. The antibody derived from the neutralizing culture was characterized by determining the amino acid and nucleotide sequences of its variable regions (Tables 1 and 5) and the complementarity determining regions (CDRs) therein and termed "LN01". Accordingly, the binding agent termed "LN01" is an IgG3-type fully human monoclonal antibody having the CDR, VH and VL sequences as shown above in Tables 1 and 2. This antibody was derived from IGHV4-39*07 and IGKV1-39*01 germline genes, and was highly somatically mutated in variable genes of both heavy chain (28%) and kappa light chain (27%) compared to germ line. The LN01 antibody also possessed a long heavy-chain complementarity-determining 3 region (CDR H3) loop composed of 20 amino acids. The LN01 VH and VL genes were cloned into IgG1 expression vectors, and the recombinant IgG1 LN01 antibody was produced by transfecting Expi293F cells. The full-length IgG1 LN01 antibody was then purified using a recombinant protein-A column (GE-Healthcare).

Figure 5:
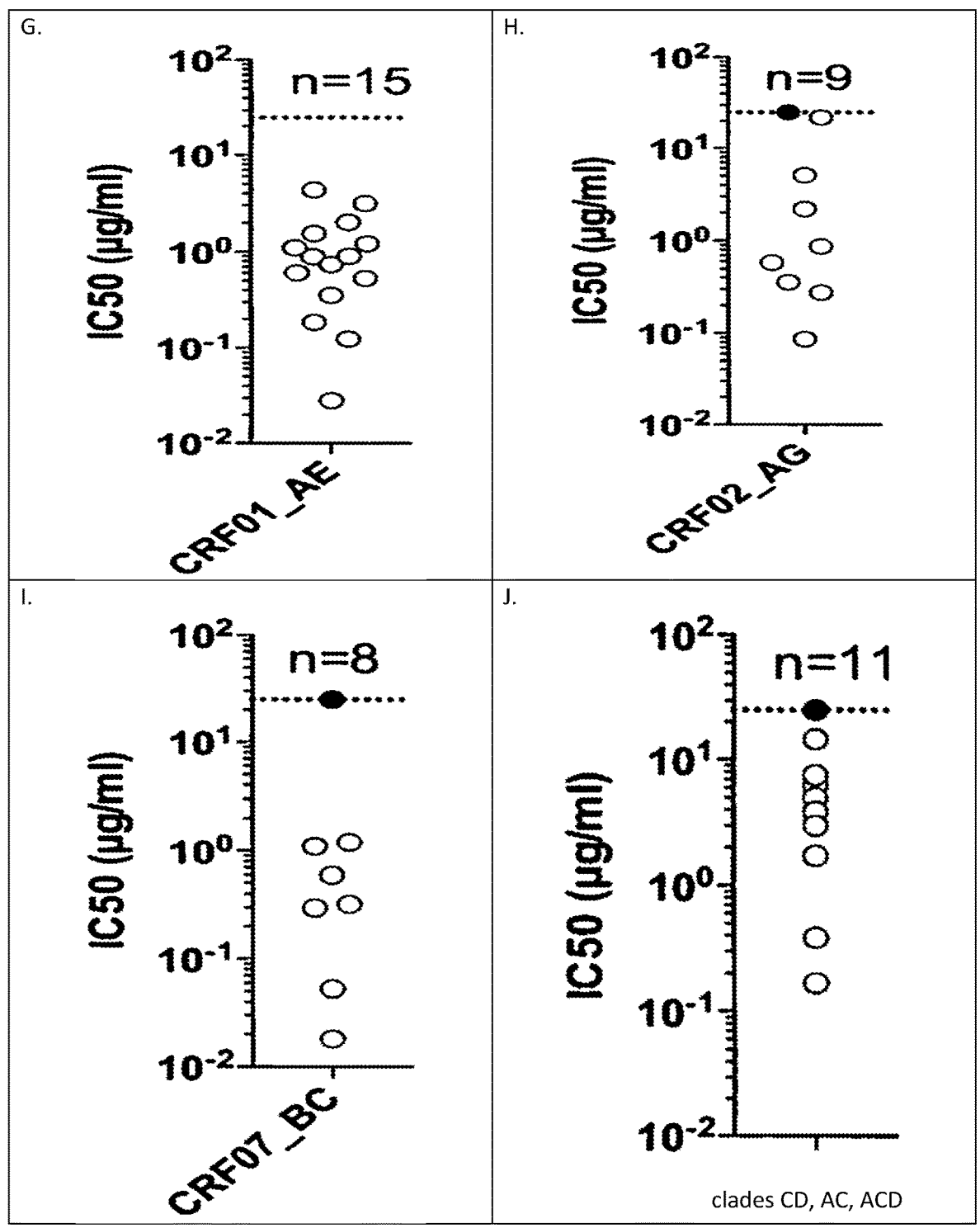
FIGS. 5A-J show the distribution of IC50 values on the whole panel of 118 viruses described in FIG. 4 and on individual clades or circulating recombinant forms.

The recombinantly produced IgG1 LN01 antibody was then tested against the Global Panel of nine (9) HIV-1 reference pseudoviruses on TZM-bl cells. Strikingly, IgG1 LN01 antibody neutralized eight (8) out of nine (9) HIV-1 pseudoviruses with $IC_{50}$ values ranging from 0.03 to 1.6 µg/ml (FIG. 3) and did not neutralize the negative control MLV pseudovirus. IgG1 LN01 antibody was subsequently tested on an extended panel of 118 HIV-1 pseudoviruses including clade A, clade B, clade C, clade D, clade G, circulating recombinant forms CRF10_CD, CRF01_AE, CRF02_AG and CRF07_BC and non-circulating recombinants AC and ACD strains. IgG1 LN01 antibody broadly neutralized 109 viruses out of 118 with IC50 below 25 µg/ml, i.e. the 92% of the tested viruses, with a median IC50 of 1.1 µg/ml (FIGS. 4 and 5). The analysis of the viruses neutralized indicated that LN01 neutralizing activity is not clade-dependent.

Example 3

Effect of Fc Receptors on LN01 Neutralizing Activity

Figure 6:
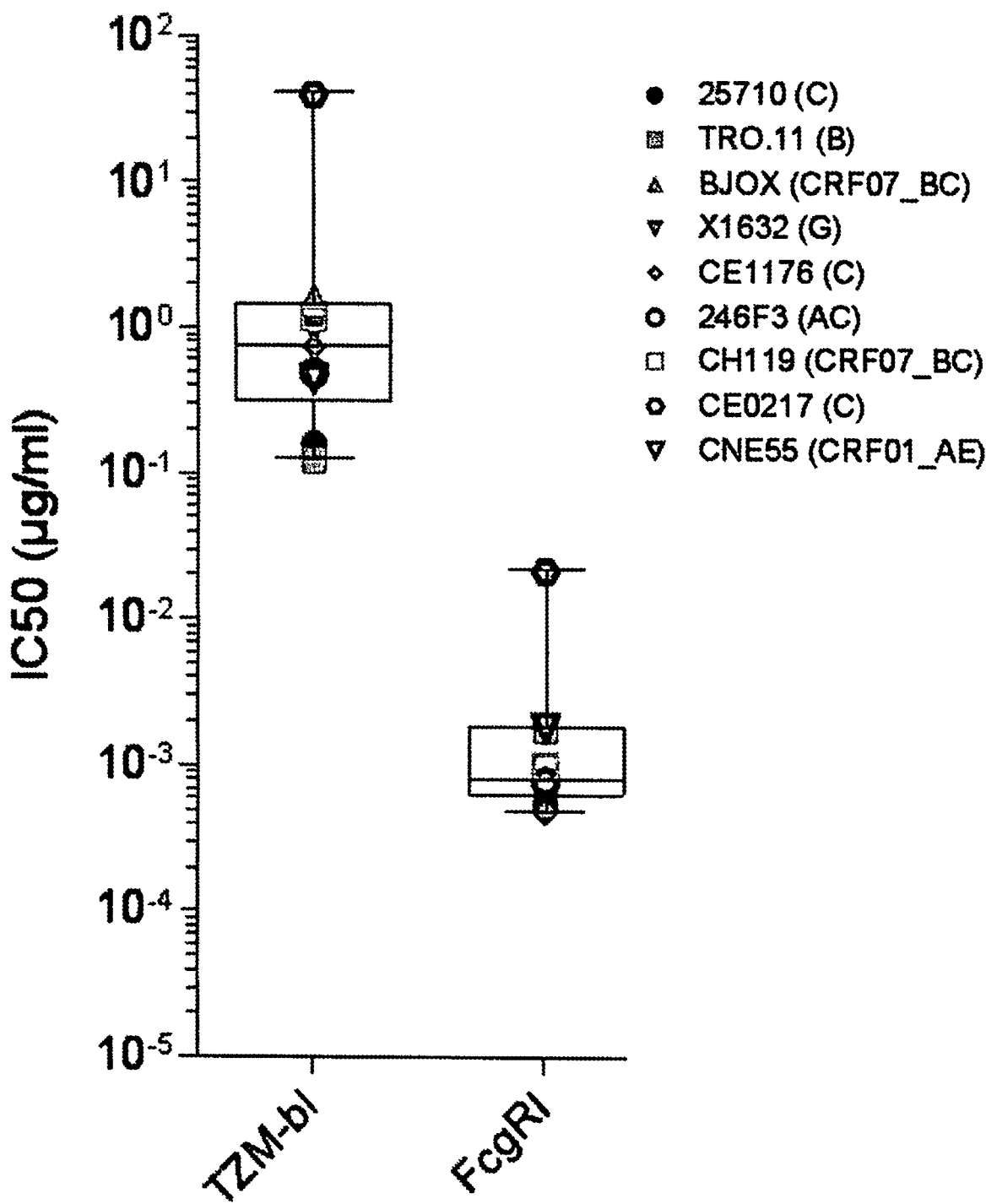
FIG. 6 shows the results of neutralization of a panel of nine (9) HIV-1 pseudoviruses from the Global Panel of HIV-1 reference strains by the monoclonal antibody LN01 when using TZM-bl or TZM-bl expressing Fc gamma Receptor I as target cells.

IgG1 LN01 antibody was tested against the Global Panel of nine (9) HIV-1 reference pseudoviruses on parental TZM-bl cells and TZM-bl cells expressing Fc-gamma receptor I (CD64) (Perez, L. G., Costa, M. R., Todd, C. A., Haynes, B. F. & Montefiori, D. C. Utilization of immunoglobulin G Fc receptors by human immunodeficiency virus type 1: a specific role for antibodies against the membrane-proximal external region of gp41. J Virol 83, 7397-7410 (2009)). Of note, the neutralizing activity of IgG1 LN01 antibody was enhanced 100-fold in TZM-bl cells expressing Fc-gamma receptor I (FIG. 6). In addition, IgG1 LN01 antibody showed potent neutralization against the strain CE0217 using TZM-bl cells expressing Fc-gamma receptor I that was not neutralized by IgG1 LN01 antibody on TZM-bl cells ($IC_{50}$>25 µg/ml)). These results suggest that by prepositioning of IgG1 LN01 antibody at the cell surface, Fc-gamma receptors might give Abs a kinetic advantage for virus inhibition. This kinetic advantage could be unique to antibodies, whose epitopes are thought to be difficult to access or exposed for only a short time on intermediate conformations of the Env protein during an early stage of fusion. Another mechanism by which Fc-gamma receptors could potentially facilitate HIV-1 neutralization is phagocytosis. HeLa cells, from which the TZM-bl cell line was constructed, are known to exhibit properties of nonprofessional phagocytes. Thus, it is possible that TZM-bl cells were converted to professional phagocytic cells by introducing Fc-gamma receptor on their surface. Any Fc-gamma-receptor-mediated antiviral effects on HIV-1 neutralizing antibodies, whether by entry inhibition or phagocytosis, might be beneficial to several cell types in vaccine setting. Fc-gamma receptors are rarely expressed on CD4+ lymphocytes, several additional HIV-1-susceptible cell types express multiple Fc-gamma receptors and are involved in sexual transmission and the early establishment of long-lived viral reservoirs. In particular, macrophages are among the first infection-susceptible cells that the virus encounters after mucosal exposure, and they are thought to serve as a long-lived virus reservoir in chronic infection. Macrophages are well known to express multiple Fc-gamma receptors as well as certain subsets of monocytes and dendritic cells. It is also important to mention that Fc-gamma receptors play a role in regulating adaptive immunity and peripheral tolerance, by facilitating antigen uptake, antigen presentation, cell activation and B cell tolerance.

Example 4

LN01 Specificity

In order to better define the specificity of IgG1 LN01 antibody we used a panel of HIV-2/HIV-1 chimeric pseudoviruses containing various segments of the HIV-1 MPER into the parental HIV-2/7312A. IgG1 LN01 antibody did not neutralize the parental HIV-2 7312A strain. Of note, IgG1 LN01 antibody was found to potently neutralize the chimeric virus 7312A.C4 in which only 6 residues from HIV-1 were replaced in the HIV-2 MPER region (LASWVKYIQ (SEQ ID NO. 65) was replaced into ITKWLWYIK (SEQ ID NO. 66)), but not the chimeric virus 7312A.C6 in which only 3 residues in the same region were replaced (LASWVKYIQ (SEQ ID NO. 65) was replaced into ITKWIKYIQ (SEQ ID NO. 67)) (FIG. 7). A similar finding was obtained with the chimeric virus 7312A.C1C where the same 6 mutations of 7312A.C4 were combined with additional 7 mutations in the N-terminal region. These results indicate that residues in the C terminal region of the gp41 MPER (L679, W680 and K683) are involved in IgG1 LN01 antibody binding.

In order to better define the specificity of LN01 we used a peptide microarray formed by 1423 15-mer peptides, overlapping by 12 amino acids, that cover the full length of the consensus HIV-1 Env gp160 sequences for clades A, B, C, D, group M, CRF01_AE and CRF02_AG. The peptides were printed onto 3D-Epoxy glass slides and were analyzed with a GenePix 4000B scanner (Tomaras, G. D. et al. Polyclonal B cell responses to conserved neutralization epitopes in a subset of HIV-1-infected individuals. J Virol 85, 11502-11519 (2011)). LN01 was tested at 20 μg/ml in parallel with a control antibody called 7B2 (that is specific for the immunodominant region of gp41) for binding to the peptide microarray. The binding of LN01 and 7B2 was detected by incubation with DyLight 649-labeled goat anti-human IgG. Fluorescence intensity was measured using a GenePix 4000B scanner and was analyzed with GenePix software (FIG. 8). Of note, IgG1 LN01 antibody did not clearly react with any of the peptides in this library, while 7B2 strongly reacted with 190-195 peptides that spanned the gp41 immunodominant region. These results indicate that IgG1 LN01 antibody does not recognize a linear epitope in HIV-1 Env.

IgG1 LN01 antibody was also tested for binding to soluble, cleaved SOSIP.664 gp140 trimers based on the subtype A transmitted/founder strain, BG505. These trimers are highly stable, homogenous and closely resemble native virus spikes when visualized by negative stain electron microscopy (EM) (Sanders, R. W. et al. A next-generation cleaved, soluble HIV-1 Env trimer, BG505 SOSIP.664 gp140, expresses multiple epitopes for broadly neutralizing but not non-neutralizing antibodies. PLoS Pathog. 9, e1003618 (2013)). All broadly neutralizing antibodies against multiple neutralizing epitopes on HIV-1 Env were highly reactive with the BG505 SOSIP.664 gp140 trimers, including quaternary epitopes antibodies (CH01, PG9, PG16 and PGT145). Conversely, non-NAbs to the CD4-binding site, CD4-induced epitopes or gp41 ectodomain did not react with the trimers, even when their epitopes were present on simpler forms of Env (e.g. gp120 monomers or dissociated gp41 subunits). The MPER was also deleted to improve trimer solubility and reduce aggregate formation. IgG1 LN01 antibody, PGT145 (V1-V2 glycan specific), PGT151 (binding to a site at the interface between gp120 and gp41) and 17b (binding to a CD4 binding induced site) antibodies were tested for binding to BG505 SOSIP.664 gp140 trimers in the presence or absence of soluble CD4 (sCD4) by surface plasmon resonance (SPR). PGT145 and PGT151 antibodies reacted strongly to BG505 SOSIP.664 gp140 trimers in the presence and absence of sCD4; 17b reacted to BG505 SOSIP.664 gp140 trimers only in the presence of sCD4. LN01 did not react with BG505 SOSIP.664 gp140 trimers neither in the presence nor in the absence of sCD4 (FIG. 9).

IgG1 LN01 antibody, in parallel with MPER-specific 10E8 antibody (Huang, J. et al. Broad and potent neutralization of HIV-1 by a gp41-specific human antibody. Nature 491, 406-412 (2012)), was also tested by ELISA against a panel of HIV-1 antigens (ConsB, consensus clade B gp140, 426c, clade C gp140, 426c-NLGS, 426c gp140 where the N-linked glycosylation sites were removed, 426c core, gp140 where the V loops were removed, UG37 gp140, clade A and gp41, recombinant ecto-domain of gp41, amino acids 541-682 from HxB2 strain, Vybion). None of the tested antigens was recognized by IgG1 LN01 antibody by ELISA (FIG. 10). Conversely, 10E8 antibody reacted to the recombinant ecto-domain of gp41. These results indicate that IgG1 LN01 antibody may recognize an epitope in the MPER of gp41 different from 10E8.

Finally, IgG1 LN01 antibody was tested against a fusion intermediate gp41 and uncoated plates (PBS), called gp41int (Lai, R. P. J. et al. A fusion intermediate gp41 immunogen elicits neutralizing antibodies to HIV-1. J Biol Chem 289, 29912-29926 (2014)). The gp41int antigen is recognized with high affinity by MPER antibodies 4E10, 2F5 and 10E8. While 10E8 reacted to gp41int by ELISA, IgG1 LN01 antibody did not react (FIG. 11). These results indicate that IgG1 LN01 antibody recognizes a conserved epitope, possibly in the MPER region, that is not readily displayed in any of the antigens tested. We can hypothesize that IgG1 LN01 antibody recognizes its cognate conformational epitope in the C-teminal region of the MPER region when displayed in the prefusion native Env conformation.

Example 5

LN01 Lack of High Affinity Binding to a MPE Peptide

In order to order to better define the specificity of IgG1 LN01 antibody we tested its binding by ELISA to a 28 amino acids long peptide that was used to co-crystallize the MPER-specific antibody 10E8 (Huang et al. Nature 2012). This peptide encompasses the entire 28-residue gp41 MPER (residues 656-683) (sequence RRR-NEQELLELDKWASLWNWFDITNWLWYIRRRR (SEQ ID NO.:81). While 10E8 reacted to this MPER peptide avidly, IgG1 LN01 antibody reacted to it very poorly (FIG. 12). These results indicate that IgG1 LN01 antibody recognizes a conserved epitope, possibly in the MPER region, that is not readily displayed in a linear peptide encompassing the entire MPER gp41 region.

Example 6

LN01 Variants with Improved Neutralizing Activity

In order to improve the potency of LN01 antibody we produced a set of variants where we introduced point mutations in the LN01 VH (25 variants) or in VL (15 variants) (FIG. 13A). These substitutions were selected based on a predicted surface exposure by replacing the original residues by W or A. Forty (40) LN01 variants were produced recombinantly by combining the mutated VH or VL with the parental VL or VH, respectively. These variants were tested against an initial panel of three HIV-1 strains (CH119, X1632; BJOX and a control virus SVA-MLV). Several LN01 variants lost neutralizing activity partially or completely (variants 13, 14, 21, 18, 19, 20, 22, 23, 24, 32 and 33), indicating an important role for the original residues in antigen recognition (in particular residues in the FR3 of the VH, in the CDR3 of the VH and in residues of the CDR1 of the VL). Of note, three variants showed a more than three-fold (3×) increase in neutralizing potency: variant 7 (D32W, mutation in the CDR1 of the VH), variant 8 (N33W in the CDR1 of the VH) and variant 38 (S67W in the FR3 of the VL) (FIGS. 13B and 13C). Remarkably, LN01 variant 7 showed 39-fold increase in potency as compared to the parental LN01 antibody. These results were confirmed when LN01 variants 7, 8 and 38 were tested in parallel with the parental LN01 antibody against a multiclade panel of 8 viruses (FIGS. 14A-K). In this second test the increased potency observed for LN01 variants 7, 8 and 38 was on average 47, 2.3 and 2.7 fold, respectively.

Based on these results additional LN01 variants (variants 41, 42, 43, 44, 48 and 50) were synthesized and tested against a panel of seven HIV-1 strains (FIGS. 15A-B). In variants (v) 41, 42, 43 and 44 the D32 residue of the CDR1 of the VH was mutated to either F (v41), Y (v42), L (v43) or I (v44). Of interest, none of these 4 mutations conferred the same increased in potency observed with the introduction of W in variant 7. In addition, only the introduction of aromatic resides (i.e., F or Y) improved LN01 activity, with Y (V42) conferring the most significant improvement of on average 3.7-fold (FIG. 15B). The introduction of hydrophobic residues in the same position did not confer any benefit in terms of neutralizing activity. Two variants in which the somatic mutations in FR1 and FR4 were reverted to the germline configuration in the presence (variant 48) or absence (variant 50) of the D32W mutation used in variant 7 were also tested. The removal of somatic mutations in framework (FR) 1 and FR4 of the VH did not alter LN01 neutralizing activity significantly. The introduction of the D32W on the backbone of variant 50 conferred a more potent neutralizing activity (on average 4.7 fold better than the parental LN01 antibody). It is worth noting, however, that D32W in the context of germlined FRs in the VH did not achieve the same level of potency improvement observed with the same mutation on the backbone of the fully mutated parental LN01 antibody (i.e., variant 7).

The combination of the mutations introduced in variants 7 and 8 (D32W and N33W) was also tested in a new variant called 49 that showed an average 81-fold higher potency as compared to the parental LN01 antibody (FIGS. 16A-B) on a panel of 7 viruses. This result indicate that LN01 variant 49 is comparable or superior to the highly potent LN01 variant 7 antibody.

Figure 17:
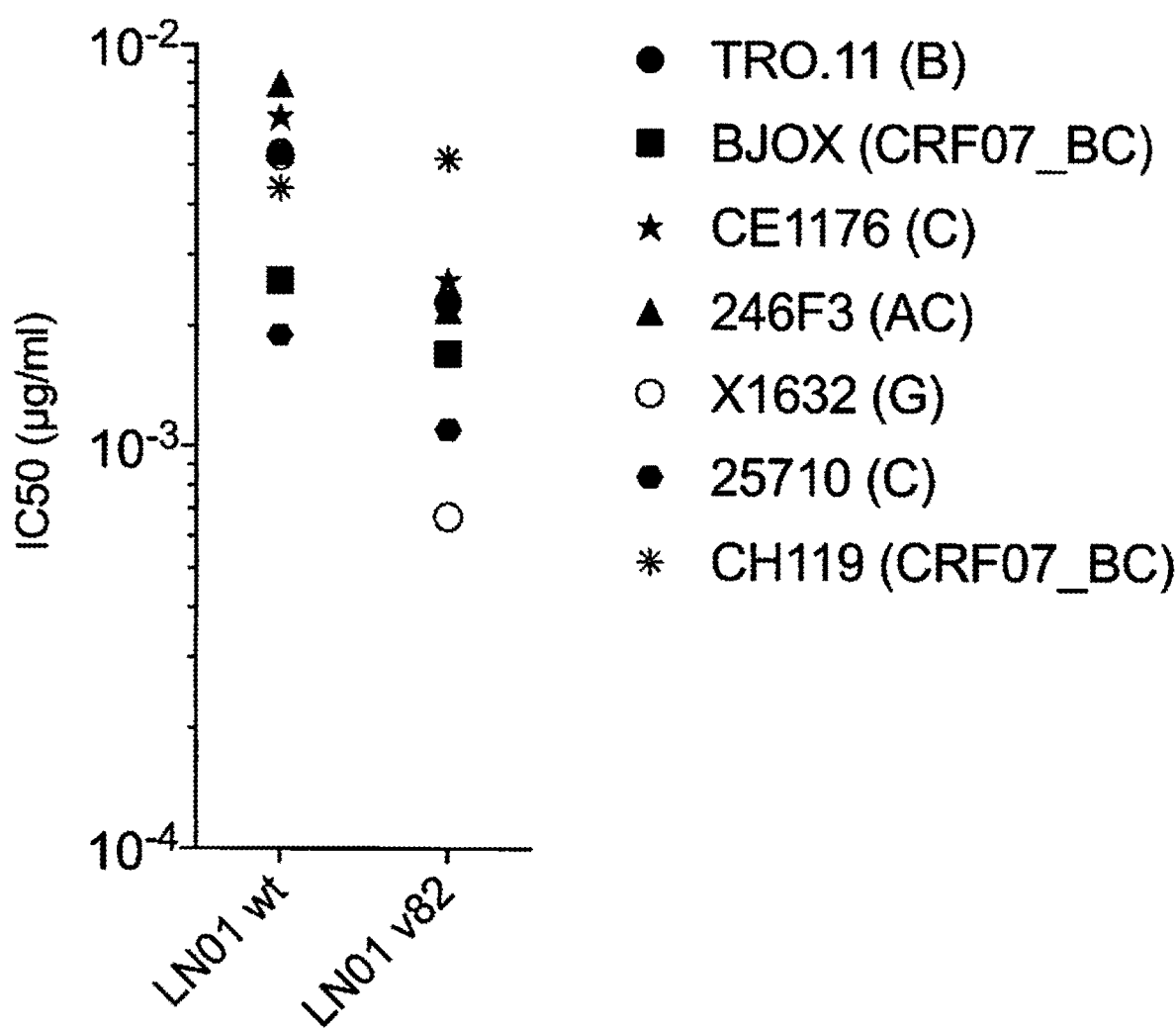
FIG. 17 shows testing of LN01 variant 82 ($IC_{50}$ (μg/ml)).

Finally, we tested another LN01 variant in which the five CDR1 somatic mutations were reverted back to the germline configuration. The mutated CDR1 sequence DSVSNDNYY (SEQ ID NO.:82; including the underlined five CDR1 somatic mutations) was reverted to GSISSSSYY (SEQ ID NO.:32; germline CDR1) to generate the LN01 variant 82. Surprisingly, LN01 variant 82 showed a potency 2.9-fold higher than that of the parental LN01 antibody (FIG. 17). This result indicates that VH CDR1 plays an important role in LN01 neutralizing activity.

While certain embodiments have been described in terms of the preferred embodiments, it is understood that variations and modifications will occur to those skilled in the art. Therefore, it is intended that the appended claims cover all such equivalent variations that come within the scope of the following claims.

What is claimed is:

1. A binding agent that neutralizes HIV in an in vitro HIV neutralization assay and/or in vivo, the binding agent comprising a combination of a heavy chain variable region (VH) and a light chain variable region (VL) selected from the group consisting of:
   a) a VH comprising complementarity determining regions (CDRs) 1, 2, and 3 as set forth in SEQ ID NOS: 1, 2, and 3, respectively; and a VL comprising CDRs 1, 2 and 3 as set forth in SEQ ID NO: 4, the amino acid sequence GTY, and SEQ ID NO: 6, respectively;
   b) a VH comprising complementarity determining regions (CDRs) 1, 2, and 3 as set forth in SEQ ID NOS: 1, 2, and 3, respectively; and a VL comprising CDRs 1, 2 and 3 as set forth in SEQ ID NOS: 4, 5, and 6, respectively;
   c) a VH comprising SEQ ID NO: 7 and a VL comprising SEQ ID NO: 8; or,
   d) a VH comprising SEQ ID NO: 13 and a VL comprising SEQ ID NO: 14.

2. The binding agent of claim 1 that is an isolated monoclonal antibody; optionally wherein the monoclonal antibody is a human monoclonal antibody, and/or the antibody isotype is IgG1 or IgG3; and/or optionally wherein the monoclonal antibody comprises comprising a constant region from a human antibody, human IgG, human IgG1, human IgG2, human IgG2a, human IgG2b, human IgG3, human IgG4, human IgM, human IgA, human IgA1, human IgA2, human IgD, human IgE, canine antibody, canine IgGA, canine IgGB, canine IgGC, canine IgGD, chicken antibody, chicken IgA, chicken IgD, chicken IgE, chicken IgG, chicken IgM, chicken IgY, goat antibody, goat IgG, mouse antibody, mouse IgG, pig antibody, and rat antibody; or a derivative thereof.

3. The binding agent of claim 1 selected from the group consisting of an $F_{ab}$, $F_{ab2}$, Fab' single chain antibody, $F_v$, single chain, mono-specific antibody, bispecific antibody, trimeric antibody, multi-specific antibody, multivalent antibody, chimeric antibody, canine-human chimeric antibody, canine-mouse chimeric antibody, antibody comprising a canine Fc, humanized antibody, human antibody, caninized antibody, CDR-grafted antibody, shark antibody, nanobody, and canelid antibody.

4. The binding agent of claim 1 comprising at least a least a first and second binding specificity, the first being against gp41 and the second being against a different antigen.

5. The binding agent of claim 1, or derivative thereof, comprising a detectable label fixably attached thereto, optionally wherein the detectable label is selected from the group consisting of fluorescein, DyLight, Cy3, Cy5, FITC, HiLyte Fluor 555, HiLyte Fluor 647, 5-carboxy-2,7-dichlorofluorescein, 5-carboxyfluorescein, 5-FAM, hydroxy tryptamine, 5-hydroxy tryptamine (5-HAT), 6-carboxyfluorescein (6-FAM), FITC, 6-carboxy-1,4-dichloro-2',7'-dichlorofluorescein (TET), 6-carboxy-1,4-dichloro-2',4',5',7'-tetrachlorofluorescein (HEX), 6-carboxy-4',5'-dichloro-2',7'-dimethoxyfluorescein (6-JOE), an Alexa fluor, Alexa fluor 350, Alexa fluor 405, Alexa fluor 430, Alexa fluor 488, Alexa fluor 500, Alexa fluor 514, Alexa fluor 532, Alexa fluor 546, Alexa fluor 555, Alexa fluor 568, Alexa fluor 594, Alexa fluor 610, Alexa fluor 633, Alexa fluor 635, Alexa fluor 647, Alexa fluor 660, Alexa fluor 680, Alexa fluor 700, Alexa fluor 750, a BODIPY fluorophores, BODIPY 492/515, BODIPY 493/503, BODIPY 500/510, BODIPY 505/515, BODIPY 530/550, BODIPY 542/563, BODIPY 558/568, BODIPY 564/570, BODIPY 576/589, BODIPY 581/591, BODIPY 630/650-X, BODIPY 650/665-X, BODIPY 665/676, FL, FL ATP, Fl-Ceramide, R6G SE, TMR, TMR-X conjugate, TMR-X, SE, TR, TR ATP, TR-X SE, a rhodamine, rhodamine 110, rhodamine 123, rhodamine B, rhodamine B 200, rhodamine BB, rhodamine BG, rhodamine B extra, 5-carboxytetramethylrhodamine (5-TAMRA), 5 GLD, 6-carboxyrhodamine 6G, Lissamine, Lissamine Rhodamine B, Phallicidine, Phalloidine, rhodamine red, Rhod-2, 6-carboxy-X-rhodamine (ROX), carboxy-X-rhodamine (5-ROX), Sulphorhodamine B can C, Sulphorhodamine G Extra, 6-carboxytetramethylrhodamine (TAMRA), tetramethylrhodamine (TRITC), rhodamine WT, Texas Red, and Texas Red-X.

6. The binding agent of claim 1 comprising an effector moiety fixably attached thereto, optionally wherein the effector moiety is selected from the group consisting of a cytotoxic drug, toxin, diphtheria A chain, exotoxin A chain, ricin A chain, abrin A chain, curcin, crotin, phenomycin, enomycin, and radiochemical.

7. An isolated polynucleotide encoding a binding agent of claim 1.

8. The isolated polynucleotide of claim 7 comprising SEQ ID NOS. 33, 34, 35, 36, 37, and 38; SEQ ID NOS. 39 and 40; or SEQ ID NOS. 45 and 46.

9. An expression vector comprising one or more polynucleotides of claim 7.

10. A host cell comprising the isolated polynucleotide of claim 7.

11. A composition comprising at least one binding agent of claim 1; and, a pharmaceutically acceptable carrier.

12. A method for detecting HIV on a cell, the method comprising contacting a test biological sample with a binding agent of claim 1; and detecting the binding agent bound to the biological sample or components thereof.

13. The method of claim 12, further comprising comparing the amount of binding to the test biological sample or components thereof to the amount of binding to a control biological sample or components thereof, wherein increased binding to the test biological sample or components thereof relative to the control biological sample or components thereof indicates the presence of a cell expressing HIV in the test biological sample.

14. The method of claim 12 wherein the test biological sample is mammalian blood.

15. The method of claim 12 wherein the method is an in vivo method; or the method is an in vitro method.

16. A method for treating and/or ameliorating HIV infection and/or AIDS in a mammal comprising administering to the mammal at least one effective dose of a pharmaceutical composition comprising a binding agent of claim 1; optionally wherein multiple doses are administered to the animal; and/or, optionally wherein the binding agent is administered in a dosage amount of about 1 to 50 mg/kg.

17. A kit for detecting the expression of HIV in or on a cell, the kit comprising a binding agent of claim 1; and instructions for use; optionally wherein the binding agent, antibody, is in lyophilized form.

18. A host cell comprising the expression vector of claim 9; and, a pharmaceutically acceptable carrier.

19. A composition comprising at least one isolated polynucleotide of claim 7; and, a pharmaceutically acceptable carrier.

20. A composition comprising at least one host cell of claim 18; and, a pharmaceutically acceptable carrier.

* * * * *